United States Patent
Evans et al.

(10) Patent No.: US 7,314,747 B1
(45) Date of Patent: Jan. 1, 2008

(54) SMRT CO-REPRESSORS, TRANSCRIPTIONAL CO-REPRESSORS THAT INTERACT WITH NUCLEAR HORMONE RECEPTORS

(75) Inventors: Ronald M. Evans, La Jolla, CA (US); J. Don Chen, New Brunswick, NJ (US); Peter Ordentlich, Solana Beach, CA (US); Michael R. Downes, San Diego, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 198 days.

(21) Appl. No.: 09/522,753

(22) Filed: Mar. 10, 2000

Related U.S. Application Data

(63) Continuation-in-part of application No. 08/522,726, filed on Sep. 1, 1995, now Pat. No. 6,489,441.

(51) Int. Cl.
C12N 1/15 (2006.01)
C12N 5/10 (2006.01)
C12N 15/00 (2006.01)
C07H 21/04 (2006.01)

(52) U.S. Cl. ............ 435/254.11; 435/325; 435/320.1; 536/23.4; 536/23.5; 536/23.1

(58) Field of Classification Search ............ 536/23.5, 536/24.31; 435/320.1, 325, 252.3
See application file for complete search history.

(56) References Cited

U.S. PATENT DOCUMENTS

| | | | |
|---|---|---|---|
| 4,981,784 A | 1/1991 | Evans et al. | |
| 5,071,773 A | 12/1991 | Evans et al. | |
| 5,091,518 A | 2/1992 | Sucov et al. | |
| 5,260,432 A | 11/1993 | Takaku et al. | |
| 6,248,559 B1 * | 6/2001 | Takashima et al. ........ | 435/69.1 |

OTHER PUBLICATIONS

Chen, et al. Nature, Oct. 1995, vol. 377, No. 6548, pp. 454-457.*
Ordentlich, et al. PNAS USA, vol. 96, No. 6, pp. 2639-2644.*
Park, et al. PNAS USA, vol. 96, No. 7, pp. 3519-3524.*
GenBank Accession No. NM_002900.1, GI: 4506452, Mar. 19, 1999.*
GenBank Accession No. O75376, GI: 47117817, Feb. 7, 2006.*
http://algoart.com/aatable.htm, printed on Feb. 28, 2007.*
Ordentlich, et al. PNAS USA, vol. 96, No. 6, pp. 2639-2644, Mar. 1999.*
Park, et al. PNAS USA, vol. 96, No. 7, pp. 3519-3524, Mar. 1999.*
Ayer et al., "Mad-Max Transcriptional Repression is Mediated by Ternary Complex Formation with Mammalian Homologs of Yeast Repressor Sin3" Cell 80:767-776 (1995).
Bahouth et al. "Immunological Approaches for Probing Receptor Structure and Function" TIPS Reviews 12:338-343 (1991).
Baniahmad et al., "Modular Srurcture of a Chicken Lysozyme Silencer: Involvement of an Unusual Thyroid Hormone Receptor Binging Site" Cell 61:505-514 (1990).
Baniahmad et al., "Kindred S Thyroid Hormone Receptor is an Active and Constitutive Silencer and a Repressor for Thyroid Hormone and Retinoic Acid Responses" Proc. Natl. Acad. Sci. USA 89:10633-10637 (1992).
Baniahmad et al., "A Transferable Silencing Domain is Present in the Thyroid Hormone Receptor, in the v-erbA Oncogene Product and in the Retinoic Acid Receptor" EMBO J. 11(3) :1015-1023 (1992).
Baniahmad et al., "Interaction of Human Thyroid Hormone Receptor β with Transcription Factor TFIIB May Mediate Target Gene Derepression and Activation by Thryoid Hormone" Proc. Natl. Acad. Sci. USA 90:8832-8836 (1993).
Baniahmad et al., "The τ4 Activation Domain of the Thyroid Hormone Receptor is Required for Release of a Putative Corepressor(s) Necessary for Transcriptional Silencing" Mol. Cell. Biol. 15 (1):76-86 (1995).
Barlow et al., "Thyroid Abnormalities and Hepatocellular Carcinoma in Mice Transgenic for v-erbA" EMBO J. 13:4241-4250 (1994).
Berger et al., "Interaction of Glucocorticoid Analogues with the Human Glucocorticoid Receptor" J. Steroid Biochem. Molec. Biol. 41(3-8) : 733-738 (1992).
Bourguet et al., "Crystal Structure of the Ligand-Binding Domain of the Human Nuclear Receptor RXR-α" Nature 375:377-382 (1995).
Brent et al., "Thyroid Hormone Aporeceptor Represses T3-Inducible Promoters and Blocks Activity of the Retinoic Acid Receptor" New Biol. 1(3) :329-336 (1989).
Bugge et al., "RXRα, a Promiscuous Partner of Retinoic Acid and Thyroid Hormone Receptors" EMBO J. 11(4) :1409-1418 (1992).
Casanova et al., "Functional Evidence for Ligand-Dependent Dissociation of Thyroid Hormone and Retinoic Acid Receptors from an Inhibitory Cellular Factor" Mol. Cell. Biol. 14(9) :5756-5765 (1994).

(Continued)

Primary Examiner—Celine Qian
Assistant Examiner—Jennifer Dunston
(74) Attorney, Agent, or Firm—Foley & Lardner LLP; Stephen E. Reiter

(57) ABSTRACT

The present invention relates to isolated polynucleotides encoding a family of silencing mediators of retinoic acid and thyroid hormone receptor (SMRT) isoforms, including vertebrate and invertebrate isoforms thereof. The invention also relates to polypeptide SMRT co-repressors encoded by invention SMRT polynucleotides, and to peptide portions thereof that can modulate transcriptional potential of a nuclear receptor. In addition, the invention relates to chimeric molecules and to complexes containing a SMRT co-repressor or peptide portion thereof, to antibodies that specifically bind such compositions, and to methods for identifying an agent that modulates the repressor potential of a SMRT co-repressor. The invention also provides methods for identifying an agent that modulates a function of a SMRT co-repressor; for modulating the transcriptional potential of a nuclear receptor in a cell using the compositions of the invention; and for identifying a molecule that interacts specifically with a SMRT co-repressor.

9 Claims, 13 Drawing Sheets

OTHER PUBLICATIONS

Cavaillès et al., "Interaction of Proteins with Transcriptionally Active Estrogen Receptors" *Proc. Natl. Acad. Sci. USA* 91:10009-10013 (1994).

Damm et al., "Protein Encoded by v-*erbA* Functions as a Thyroid-Hormone Receptor Antagonist" *Nature* 339 (6226):593-597 (1989).

Damm et al., "Functional Inhibition of Retinoic Acid Response by Dominant Negative Retinoic Acid Receptor Mutants" *Proc. Natl. Acad. Sci. USA* 90:2989-2993 (1993).

Damm and Evans, "Identification of a Domain Required for Oncogenic Activity and Transcriptional Suppression by v-erbA and Thyroid-Hormone Receptor α" *Proc. Natl. Acad. Sci. USA* 90:10668-10672 (1993).

Durfee et al. "The Retinoblastoma Protein Associates with the Protein Phosphatase Type 1 Catalytic Subunit" *Genes & Dev.* 7:555-569 (1993).

Fondell et al., "Unliganded Thyroid Hormone Receptor Inhibits Formation of a Functional Preinitiation Complex: Implications for Active Repression" *Genes & Dev.* 7:1400-1410 (1993).

Gandrillon et al., "Expression of the v-*erbA* Oncogene in Chicken Embryo Fibroblasts Stimulates Their Proliferation In Vitro and Enhances Tumor Growth In Vivo" *Cell* 49:687-697 (1987).

Halachmi et al., "Estrogen Receptor-Associated Proteins: Possible Mediators of Hormone-Induced Transcription" *Science* 264:1455-1458 (1994).

Hollenberg and Evans, "Multiple and Cooperative Trans-Activation Domains of the Human Glucocorticoid Receptor" *Cell* 55:899-906 (1988).

Kliewer et al., "Retinoid X Receptor Interacts with Nuclear Receptors in Retinoic Acid, Thyroid Hormone and Vitamin $D_3$ Signalling" *Nature* 355:446-449 (1992).

Le Douarin et al., "The N-terminal Part of TIF1, a Putative Mediator of the Ligand-Dependant Activation Function (AF-2) of Nuclear Receptors, is Fused to B-raf in the Oncogenic Protein T18" *EMBO J.* 14(9):2020-2033 (1995).

Lee et al., "Interaction of the Thyroid-Hormone Receptor with a Conserved Transcriptional Mediator" *Nature* 374:91-94 (1995).

Levine and Manley, "Transcriptional Repression of Eukaryotic Promoters" *Cell* 59:405-408 (1989).

Mangelsdorf et al., "Nuclear Receptor that Identifies a Novel Retinoic Acid Response Pathway" *Nature* 345 (6272):224-229 (1990).

Mangelsdorf et al., "A Direct Repeat in the Cellular Retinol-Binding Protein Type II Gene Confers Differential Regulation by RXR and RAR" *Cell* 66:555-561 (1991).

Muñoz et al. "Characterization of the Hormone-binding Domain of the Chicken c-*erbA*/Thyroid Hormone Receptor Protein" *EMBO J.* 7:155-159 (1988).

Saitou et al., "Inhibition of Skin Development by Targeted Expression of a Dominant-Negative Retinoic Acid Receptor" *Nature* 374:159-162 (1995).

Sap et al., "The c-*erb*-A Protein is a High-Affinity Receptor for Thyroid Hormone" *Nature* 324:635-640 (1986).

Sap et al., "Repression of Transcription Mediated at a Thyroid Hormone Response Element by the v-*erb*-A Oncogene Product" *Nature* 340:242-244 (1989).

Schreiber-Agus et al., "An Amino-Terminal Domain of Mxi1 Mediates Anti-Myc Oncogenic Activity and Interacts with a Homolog of the Yeast Transcriptional Repressor SIN3" *Cell* 80:777-786 (1995).

Seol et al., "Isolation of Proteins That Interact Specifically with the Retinoid X Receptor: Two Novel Orphan Receptors" *Molecular Endocrinology* 9(1):72-85 (1995).

Thompson et al., "Identification of a Novel Thyroid Hormone Receptor Expressed in the Mammalian Central Nervous System" *Science* 237:1610-1614 (1987).

Tsai et al., "A Mutated Retinoic Acid Receptor-α Exhibiting Dominant-Negative Activity Alters the Lineage Development of a Multipotent Hematopoietic Cell Line" *Genes & Dev.* 6:2258-2269 (1992).

Tsai and Collins, "A Dominant Negative Retinoic Acid Receptor Blocks Neutrophil Differentiation at the Promyelocyte Stage" *Proc. Natl. Acad. Sci. USA* 90:7153-7157 (1993).

Webster et al., "The Yeast $UAS_G$ is a Transcriptional Enhancer in Human HeLa Cells in the Presence of the GAL4 *Trans*-Activator" *Cell* 52:169-178 (1988).

Webster et al. "The Hormone-Binding Domains of the Estrogen and Glucocorticoid Receptors Contain an Inducible Transcription Activation Function" *Cell* 54:199-207 (1988).

Weinberger et al., "Domain Structure of Human Glucocorticoid Receptor and its Relationship to the v-*erb-A* Oncogene Product" *Nature* 318:670-672 (1985).

Weinberger et al., "The c-*erb-A* Gene Encodes a Thyroid Hormone Receptor" *Nature* 324:641-646 (1986).

Yang et al., "Characterization of DNA Binding and Retinoic Acid Binding Properties of Retinoic Acid Receptor" *Proc. Natl. Acad. Sci. USA* 88:3559-3563 (1991).

Yu et al., "RXRβ: A Coregulator That Enhances Binding of Retinoic Acid, Thyroid Hormone, and Vitamin D Receptors to Their Cognate Response Elements" *Cell* 67:1251-1266 (1991).

Zenke et al., "v-*erbA* Oncogene Activation Entails the Loss of Hormone-Dependent Regulator Activity of c-*erbA*" *Cell* 61:1035-1049 (1990).

Kao et al., "A histone deacetylase corepressor complex regulates the Notch signal transduction pathway," *Genes & Develpoment*, 12:2269-2277, 1998.

Laherty et al., "SAP30, a Component of the mSin3 Corepressor Complex Involved in N-CoR-Mediated Repression by Specific Transcription Factors," *Molecular Cell*, 2:33-42, 1998.

Lin et al., "Role of the histone deacetylase complex in acute promyelocytic leukaemia," *Nature*, 391:811-814, 1998.

Muscat et al., "The corepressor N-CoR and its variants RIP13a and RIP13Δ1 directly interact with the basal transcription factors TF∥B, TAF∥32 and TAF∥70," *Nucleic Acids Research*, 26/12:2899-2907, 1998.

Ordentlich et al., "Unique forms of human and mouse nuclear receptor corepressor SMRT," *Proc. Natl. Acad. Sci. USA*, 96:2639-2644, 1999.

Song et al., "Ubiquitous receptor: A receptor that modulates gene activation by retinoic acid and thyroid hormone receptors," *Proc. Natl. Acad. Sci. USA*, 91:10809-10813, 1994.

Torchia et al., "Co-activators and co-repressors in the integration of transcriptional responses," *Current Opinion in Cell Biology*, 10:373-383, 1998.

Tsai et al., "SMRTER, a *Drosophila* Nuclear Receptor Coregulator, Reveals that EcR-Mediated Repression Is Critical for Development," *Molecular Cell*, 4:175-186, 1999.

* cited by examiner

```
   1  MEAWDAHEDKEAFAAEAQKLGGDEECWTSGLPFEVEEREVIKASEHAECE
  51  SAFSYAEEGHELELGLHDTAREVLEREETISNEEELISSAKHESVLERQI
 101  GAISQGMSVQLHVEYSEHAKAEVGEVTMGLELEMDEKKLAEFSGVKQEQL
 151  SPRGQAGPPESLGVPTAQEASVLRGTALGSVPGGSITKGIPSTRVPSDSA
 201  ITYRGSITHGTPADVLYKGTITRIIGEDSPSRLDRGREDSLPKGHVIYEG
 251  KKGHVLSYEGGMSVTQCSKEDGRSSSGPPHETAAPKRTYDMMEGRVGRAI
 301  SSASIEGLMGRAIPPERHSPHHLKEQHHIRGSITQGIPRSYVEAQEDYLR
 351  REAKLLKREGTPPPPPPSRDLTEAYKTQALGPLKLKPAHEGLVATVKEAG
 401  RSIHEIPREELRHTPELPLAPRPLKEGSITQGTPLKYDTGASTTGSKKHD
 451  VRSLIGSPGRTFPPVHPLDVMADARALERACYEESLKSRPGTASSSGGSI
 501  ARGAPVIVPELGKPRQSPLTYEDHGAPFAGHLPRGSPVTMREPTPRLQEG
 551  SLSSSKASQDRKLTSTPREIAKSPHSTVPEHHPHPISPYEHLLRGVSGVD
 601  LYRSHIPLAFDPTSIPRGIPLDAAAAYYLPRHLAPNPTYPHLYPPYLIRG
 651  YPDTAALENRQTIINDYITSQQMHHNTATAMAQRADMLRGLSPRESSLAL
 701  NYAAGPRGIIDLSQVPHLPVLVPPTPGTPATAMDRLAYLPTAPQPFSSRH
 751  SSSPLSPGGPTHLTKPTTTSSSERERDRDRERDRDREREKSILTSTTTVE
 801  HAPIWRPGTEQSSGSSGSSGGGGGSSSRPASHSHAHQHSPISPRTQDALQ
 851  QRPSVLHNTGMKGIITAVEPSKPTVLRSTSTSSPVRPAATFPPATHCPLG
 901  GTLDGVYPTLMEPVLLPKEAPRVARPERPRADTGHAFLAKPPARSGLEPA
                                        ┌─→C-SMRT
 951  SSPSKGSEPRPLVPPVSGHATIARTPAKNLAPHHASPDPPAPPASASDPH
1001  REKTQSKPFSIQELELRSLGYHGSSYSPEGVEPVSPVSSPSLTHDKGLPK
1051  HLEELDKSHLEGELRPKQPGPVKLGGEAAHLPHLRPLPESQPSSSPLLQT
1101  APGVKGHQRVVTLAQHISEVITQDYTRHHFQQLSAPLPAPLYSFPGASCP
1151  VLDLRRPPSDLYLPPPDHGAPARGSPHSEGGKRSPEPNKTSVLGGGEDGI
1201  EPVSPPEGMTEPGHSRSAVYPLLYRDGEQTEPSRMGSKSPGNTSQPPAFF

1251  SKETESNSAMVKSKKQEINKKLNTENRNEPEYNISQPGTEIFNMPAITGT

1301  GLMTYRSQAVQEHASTNMGLEAIIRKALMGKYDQW.EESPPLSANAFNPL

1350  NASASLPAAMPITAADGRSDHTLTSP.GGGGKAKVSGRPSSRKAKSPAPG

1399  LA..SGDRPPSVSSVHSEGDCNRRTPLTNRVWEDRPSSAGSTPFPYNPLI

1447  MRLQAGVMASPPPPGLPAGSGFL..AGPHHA...WDEEPKPLLCSQYETL
```

FIGURE 2

```
  1  MSGSTQLVAQTWRAATEPRYPPRSLSYPVQLARTHTDVGLLEYQHHSRDYASHLSPGSIIQPQRRRPSLLSEPQPGMERSQELHLRPESHSYLPELGKSEM
  1  MSGSTQPVAQTWRAAEPRYPPRGISYPVQIARSHTDVGLLEYQHHPRDYTSHLSPGSIIQPQRRRPSLLSEPQPGSERSQELHLRPESRTFLPELGKPDI

101  EPIESKRPRLELLPDPLLRPSPLLATGOPAGSEDLTKDRSLTGKLEPVSPPSPPHTDPELELVPPRLSKEELIQNMDRVDREITMVEQQISKLKKKQOOL
101  EPIESKRPRLELLPDTLLRPSPLLATGQPSGSEDLTKDRSLAGKLEPVSPPSPPHADPELELAPSRLSKEELIQNMDRVDREITMVEQQISKLKKKQQQL

201  EEEAAKPPEPEKPVSPPPIESKORSLVQIIYDENRKKAEAAHRILEGLGPQVELPLYNQPSDTRQYHENIKINQAMRKKLILYFKRRNHARKQWKQRPCQ
201  EEEAAKPPEPEKPVSPPPIESKHRSLVQIIYDENRKKAEAAHRILEGLGPQVELPLYNQPSDTRQYHENIKINQAMRKKLILYFKRRNHARKQWEQRFCQ

301  RYDQLMEALEKKVERIENNPRRRAKESKVREYYEKQPPEIRKQRELQERMQSRVGQRGSGLSMSAARSEHEVSEIIDGLSEQENLEKQMRQLAVIPPMLY
301  RYDQLMEAWEKKVERIENNPRRRAKESKVREYYEKQPPEIRKQRELQERMQSRVGQRGSGLSMSAARSEHEVSEIIDGLSEQENLEKQMRQLAVIPPMLY

401  DADQQRIKFINQNGLMADPMKVYKDRQVKNMMSEQERETPREKFMQHPKNFGLIASFLERKTVAECVLYYYLTKKQMENYKSLVRRSYRRRGKSQQQQQQ
401  DADQQRIKFINQNGLMDDPMKVYKDRQVTNMMSEQERDTFREKFMQHPKNFGLIASPLERKTVAECVLYYYLTKKQMENYKSLVRRSYRRRGKSQQQQQQ

501  QQQQQQQQQQPKPRSSQKEKDEKEKEKEAEKEEKPEVENDKEDLLKEKTDDTSGEDNDEKEAVASKGRKTANSQGRRKGRITRSMANEANSEKAITPQQ
501  QQQQQQQ----KARSSQEEKEKEKEKEADKEEEKQDAENEKEELSKEKTDDTSGEDNHEKEAVASKGRKTANSQGRRKGRITRSMANEANHEETATPQQ

601  SAELASMELNESSRWTEEEMETAKKGLLEHGRNWSAIARMVGSKTVSQCKNFYFNYKKRQNLDEILQQHKLDMEKERNARRKKKAPAAASEEAAFPPVV
597  SSELASMEDNESSRWTEEEMETAKKGLLEHGRNWSAIARMVGSKTVSQCKNFYFNYKKRQNLDEILQQHKLDMEKERNARRKKKTPAAASEETAFPPAA

701  EDEEMEASGVSGNEEEMVEEAEALHASGNEVPR-GECSGPATVNNSSDTESIPSPHTEAAKDTGQNGPKPPATLGADGPPPOPPTPPRRTSRAPIEPTPA
697  EDEEMEASGASANEEELAEEAEASQASGNEVPRVGECSGPAAVNNSSDTESVPSPRSEAMKDTG---PKPTGTEALPAATQPPVPPPEEPAVAPAEPSPV

800  SEATGAPTPPPAPPSPSAPPPVVPKEEKEESETAAAPP--VEEGEHQKPPAAEE-LAVDTGKAEEP---VKSECTEEAEEGPA-KGKDAEAAEATAEGALK
794  PDASGPPSPEPSHGLPH-PRLLWTRMQNKKPRLLQLPRQRMPRSRSLRPRRSMWEKPEKPEASEEPPESVKSDHKEETEEEPEDKAKGTEAIETVSEAPLK

893  AEKKEGQSGRATTAKSSGAPQDSDSSATCSADEVDEAEGGDKNRLLSPRPSLLTPTGDPRANASPQKPLDLKQLKQRAAAIPPIQVTKVHEPPREDAAPT
893  VEE-AGSKAAVTKGSSGATQDSDFSATCSADEVDEPEGGDKGRLLSPRPSLLTPAGDPRASTSPQKPLDLKQLKQRAAAIPPIQVTKVHEPPREDTVPP

993  KPAPPAPPPPQNLQPESDAPQQPGSSFRGKSRSPAFPADKEA-------FAAEAQKLPGDPPCWTSGLPFFVPPREVIKASPHAPDPSAFSYAPPGMPL
992  KPVPPVPPPTQHLQPEGDVSQQSGGSPRGKSRSPVPPAEKEAEKPAFFPAFPTEGPKLPTEPPRWSSGLPFFPIPPREVIKTSPHAADPSAFSYTPPGMPL

1095 PLGLHDTARPVLPRPPTISNPPPLISSAKHPSVLERQIGAISQ-GMSVQLHVPYSEHAKAPVGPVTMGLPLPMDPKKLAPFSGVKQEQLSPRGQAGPPES
1092 PLGLHDSARPVLPRPPISNPPPLISSAKHPGVLERQLGAISQQGMSVQLRVPHSEHAKAPMGPLTMGLPLAVDPKKL---------------------

1184 LGVPTAQEASVLRGTALGSVPGGSITKGIPSTRVPSDSAITYRGSITHGTPADVLYKGTITRIIGEDSPSRLDRGREDSLPRGHVIYEGKKGHVLSYEGG
1169 ------------GTALGSATSGSITKGLPSTRAADGPS--YRGSITHGTPADVLYKGTISRIVGEDSPSRLDRAREDTLPKGHVIYEGKKGHVLSYEGG

1284 MSVTQCSKEDGRSSSGPPHETAAPKRTYDMOEGRVGRAISSASIEGLMGRAIPPERHSPHELKEQHHIRGSITQGIPRSYVEAQEDYLRREAKLLKREGT  h-SMRT
1254 MSVSQCSKEDGRSSSGPPHETAAPKRTYDMOEGRVGRTVTSASIEGLMGRAIP-EQHSPH-LKEQHHIRGSITQGIPRSYVEAQEDYLRREAKLLKREGT  m-SMRT

1384 PPPPPPSRDLTEAYKT---QALGPLKLKPAHEGLVATVKEAGRSIHEIPREELRHTPELPLAPRPLKEGSITQGTPLKYDTGASTTGSKKHDVRSLIGSP  h-SMRT
1352 PPPPPPPRDLTETYKPRPLDPLGPLKLKPTHEGVVATVKEAGRSIHEIPREELRRTPELPLAPRPLKEGSITQGTPLKYDSGAPSTGTKKHDVRSIIGSP  m-SMRT

1481 GRTPPPVHPLDVMADASALERACYEESLKSRPGTASSSGGSIARGAPVIVPELGKPRQSPLTYEDHGAPFAGHLPRGSPVTHQREPTPRLQEGSLSSSKAS  h-SMRT
1452 GRPPPALHPLDDMADASALERACYEESLKSRSGTSSGAGGSITRGAPVVVVPELGKPRQSPLTYEDHGAPFTSHLPRGSPVTTRREPTPRLQEGSLLSSKAS  m-SMRT

1561 QDRKLTSTPREIAKSPHSTVPEHGHPHPISPYEHLLRGVSGVDLYRSHIPLAFDPTSIPRGIPLDAAAAA-YYLPRHLAPNPTYPHLYPPYLIRGYPDTAAL  h-SMRT
1552 QDRKLTSTPREIAKSPHSTVPEHGHPHPISPYEHLLRGVTGVDLYRGHIPLAFDPTSIPRGIPLEAAAAAYYLFRHLAPSPTYPHLYPPYLIRGYPDTAAL  m-SMRT

1690 ENRQTIINDYITSQQMHHNTATAMAQRADMLRGLSPRESSLALNYAAGPRGIIDLSQVPHLFVLVPPTGTPATAMDRLAYLPTAPQPFSSRHSSSPLSP  h-SMRT
1652 ENRQTIINDYITSQQMHHNAASAMAQRADMLRGLSPRESSLALNYAAGPRGIIDLSQVPHLFVLVPPTPGTPATAIDRLAYLPTAPPPFSSRHSSSPLSP  m-SMRT

1780 GGPTHLTKPTTTSSSEREKDRDREKDRDREREKSILTSTTTVEHAPIWRPGTEQSSGSSQSSGGGGGSSSRPASHSHAMQHSPISPRTQDALQQRPSVLH  h-SMRT
1752 GGPTHLAKPTATSSSERERERERERD------KSILTSTTTVEHAPIWRPGTEQSSGAGQSS--------RPASHTHQH--SPISPRTQDALQQRPSVLH  m-SMRT

1880 NTGMKGIITAVEPSKPTVLR---STSTSSPVRPAATFPPATHCPLGGTLDGVYPTLMEFVLLPKEAPRVARPERPRADTGHAFLAKPPARSGLEPASSPS  h-SMRT
1836 NTSMKGVVTSVEPGTPTVLRMARSTSTSSPVRPAATPPPATHCPLGGTLEGVYPTLMEPVLLPKETSRVARPERARVDAGHAFLTKPPGR---EPASSPS  m-SMRT

1977 KGSEPRPLVPPVSGHATIARTPAKNLAPHHASPDPPAPPASASDPHREKTQSKPPSIQELELRSLGYH-GSSYSPEGVEPVSPVSSPSLTHDKGLPKHLE  h-SMRT
1933 KSSSPRSLAPPSSSHTAIARTPAKNLAPHHASPDPPAPT-SASDLHREKTQSKPFSIQELELRSLGYHSGAGYSPDGVEPISPVSSPSLTHDKGLSRPLE  m-SMRT

2076 ELDKSHLEGELRPKQPGPVKLGGEAAHLPHLRPLFESQPSSSPLLQTAPGVKGHQRVVTLAQHISEVITQDYTRHGPQQLSAPLPAPLYSPPGASCPVLD  h-SMRT
2032 ELEKSKLEGELRHKQPGPMKLSAEAAHLPHLRPLPESQPSSSPLLQTAPGIRGHQRVVTLAQHISEVITQDYTRHGPQQLSGPLPAPLYSPPGASCPVLD  m-SMRT

2176 LRRPPSDLYLPPPDHGAPARGSPHSSGGKRSPEPNKTSVLGGGEDGIEPVSPPEGMTEPGKSRSAVYPLLYRDGEQTEPSRMGSKSPGMTSQPPAFFSKL  h-SMRT
2132 LRRPPSDLYLPPPDHGTPARGSPHSEGGKRSPEPSKTSVLGSSEDAIEPVSPPEGMTEPGRARSTAYPLLYRDGEQGEPR-MGLESPGMTSQPPYTFFSKL  m-SMRT

2276 TESNSAMVKSKKQEINKKLNTHNRNEPSYNISQPGTEIFNMPAITGTGLMTYRSQAVQEHASTMNGLEAIIRKALMGKYDQWEESPPLSAHAFNFLNASA  h-SMRT
2231 TESNSAMVKSKKQEINKKLNTHNRNEPSYNIGQPGTEIFNMPAITGAGLMTCRSQAVQEHASTMNGLEAIIRKALMGKYDQWEEPPPLGANAFNPLNASA  m-SMRT

2376 SLPAA-KPITAADQRSDHTLTSPGGGGKAKVSGRPSSRKAKSPAPGLASGDRPPSVSSVHSEGDCNRRTPLTNRVWEDRPSSAGSTPFPYNPLIMRLQAG  h-SMRT
2331 SLPAAAMPITTADGRSDKALTSPGGGGKAKVSGRPSSRKAKSPAPGLASGDRPPSVSSVHSEGDCNRRTPLTNRVWEDRPSSAGSTPFPYNPLIMRLQAG  m-SMRT

2475 VMASPPPPGLPAGSGPLAGPHHAWDEEPKPLLCSQYETLSDSE  h-SMRT
2431 VMASPPPPGLAAGSGPLAGPHHAWDEEPKPLLCSQYETLSDSE  m-SMRT
```

LBD-signature Motif (protein sequence, residues 1–3446, illegible at this resolution)

SNOR motif

```
              10         20         30         40         50
SMRTER:  573  KEDLMQIQKVDNEIKSAETTMETLRKKEKSLMEEAALAKEQRAAKELND
mN-CoR:  177  KEELIQSMDRVDREIAKVEQQILKLKKKQQQLEEEA--AKPPEPEKPVSP
hSMRT :  169  KEELIQNMDRVDREITMVEQQISKLKKKQQQLEEEA--AKPPEPEKPVSP 60         70         80         90        100
SMRTER:  623  NNNDQEPMVELSWRSQMLAEKTYAANRKTAQAQHSMLQNAAADESSPGSV
mN-CoR:  226  ------PPVEQKHRS--IVQIIYDENRKKAEEAHKIFEGLGPKVE----
hSMRT :  217  ------PPIESKHRS--LVQIIYDENRKKAEAAHRILEGLGPQVE----

110        120        130        140        150
SMRTER:  673  AGRPWLPLYNQPLDVEALAMLIRQHQSQIRAPLLLHIRKLKAERWAHNQG
mN-CoR:  263  -----LPLYNQPSDTKMYHENIKTNQV-MRKKLILFKRRNHARKQREQK
hSMRT :  254  -----LPLYNQPSDTRDYHENIKINQA-MRKKLILYFKRRNHARKQWKQK 160        170        180        190        200
SMRTER:  723  LVEKYTKDQADWQRRCERMEASAKRKARPAKNREFFEKVFTELRKQREDK
mN-CoR:  307  ICQRYDQLMEAWEKKVDRIENNPRRKAKESKTREYYEKQFPEIRKQREQQ
hSMRT :  298  FCQRYDQLMEALEKKVERIENNPRRRAKESKVREYYEKQFPEIRKQRELQ 210        220        230        240        250
SMRTER:  773  ERFN-RVGSR-------IKSEADLEEIMDGLQEQALEDKKMRSYAVIPP
mN-CoR:  357  ERFQ-RVGQRGAGLSATIARSEHEISEIIDGLSEQENNEKQMRQLSVIPP
hSMRT :  348  ERMQSRVGQRGSGLSMSAARSEHEVSEIIDGLSEQENLEKQMRQLAVIPP 260        270        280
SMRTER:  814  LMHDARQRRCAYHNENGLIEDMVAVHQQRKALNM
mN-CoR:  406  MMFDAEQRRVKFINMNGLMEDPMKVYKDRQFMNV
hSMRT :  398  MLYDADQQRIKFINMNGLMADPMKVYKDRQVMNM
```

SANT domain

```
                         10         20         30         40
SMRTER    : 848  WTAGEKETFKEKYLQHPKNFGAIAASLDR-KSPQDCVRYYYLSKKTENY  100%
mN-CoR(1) : 440  WTDHEKEIFKDKPIQHPKNFGLIASYLER-KSVPDCVLYYYLTKKNENY  68/80%
hSMRT(1)  : 432  WSEQEKETFREKFMQHPKNFGLIASFLER-KTVAECVLYYYLTKKNENY  64/82%
c14B9.6   : 615  WSPEERSLFKSRQADHVKIFHGLTEFFVD-KTASDIVLFYYMNKKTEDV  35/53%
cF53H10   : 218  WTPDETYQFQDAIYQSEKDFKVAMELPG-KSVKECVQFYYTWKKDCPD  38/56%
xER1      : 277  WTEEECRNFEQGLKAIGKDFHLIQANKVRTRSVGECVAFYYMWKKSERV  36/56%
mN-CoR(2) : 627  WTEEEMEVAKKGLVEHGRNWSAIAK-MVGTKSEAQCKNFYFNYKRRHNL  34/53%
hSMRT(2)  : 615  WTEEEMETAKKGLLEHGRNWSAIAR-MVGSKTVSQCKNFYFNYKKRQNL  38/57%
hKIAA0071 : 106  WTVKDKVLFEQAFSFHSKIFHRIDQMLPD-KSIASLVKFYYSWKKIRTK  37/50%
cMTA-I    : 198  WTDQEITLFENCYQIPGKNFSQIRSALCH-RSLQSIVQFYYESKKRVKV  39/51%
YCR592    : 673  FIDHEHSLFLEGYLIHEKKFGKISHYMGGLRSPEECVLHYYRTKKTVNY  46/62%
                     α-helix              α-helix
```

ITS motif

```
SMRTER:2424  TRQIVMHDYITSQQMQ
  SMRT:1681  NRQTIINDYITSQQMH
 N-CoR:1615  TRQTILNDYITSQQMQ
```

GSI motif

```
SMRTER: 2274  VKSGSIHGTPANS
        2236  GKHGSITQGTPLHM
  SMRT: 1203  VPGGSITKGIPSTR
        1224  TYRGSITHGTPADV
        1350  HIRGSITQGIPRSY
        1446  LKEGSITQGTPLKY
        1517  SSGGSIARGAPVIV
 N-CoR:  921  TPPGSILISSPIKP
        1064  IMGGSISQGTPGTY
        1092  PSVGSISLGLPRQQ
        1149  VQEGSITRGTPASK
        1171  SLRGSITQGTPALP
        1302  VLSGSIMQGTPRAT
        1388  IIEGSISQGTPIKP
C14B9.6: 920  QTQGSLTSGTPFQA
```

LSD motif

```
SMRTER:3430  ESKPLLLSKYDALSD-ED
  SMRT:2501  EPKPLLCSQYETLSDSE
 N-CoR:2436  EPAPLLSAQYETLSDSDD
```

FIGURE 9

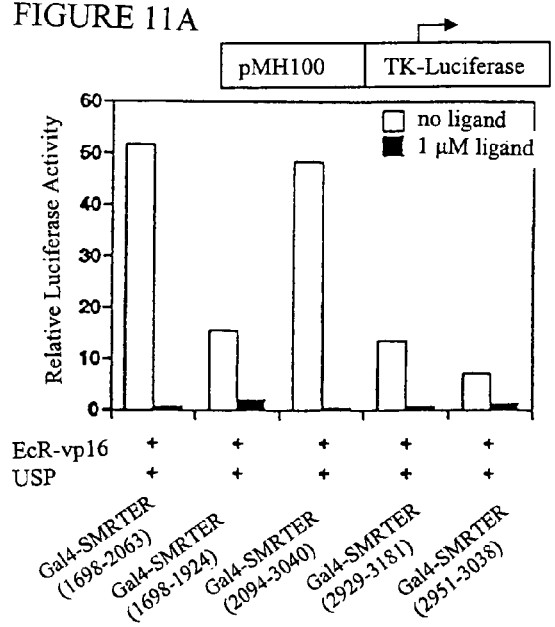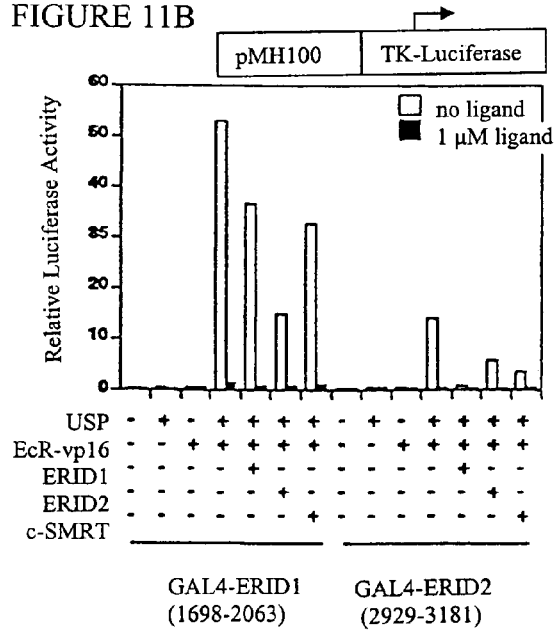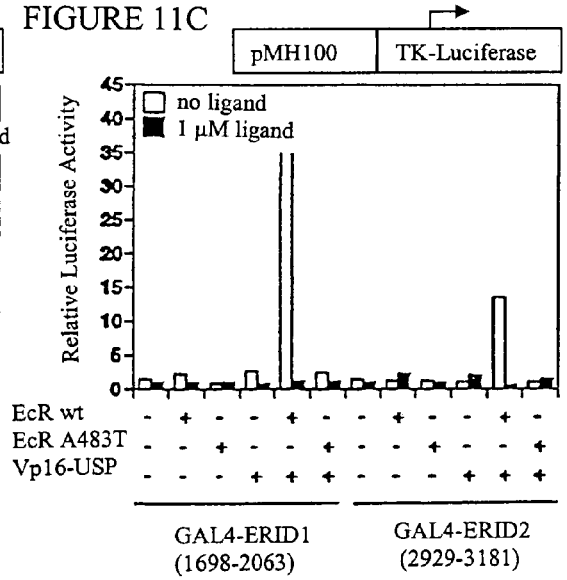

US 7,314,747 B1

SMRT CO-REPRESSORS, TRANSCRIPTIONAL CO-REPRESSORS THAT INTERACT WITH NUCLEAR HORMONE RECEPTORS

RELATED APPLICATIONS

This application is a continuation-in-part of U.S. application Ser. No. 08/522,726, filed Sep. 1, 1995, now U.S. Pat. No. 6,489,441, and is related to U.S. application Ser. No. 09/523,068, filed on even date herewith, now abandoned, each of which is incorporated by reference herein in its entirety.

FIELD OF THE INVENTION

The present invention relates to intracellular receptors, methods for the modulation thereof, and methods for the identification of novel ligands therefor. In a particular aspect, the present invention relates to methods for the identification of compounds which function as ligands (or ligand precursors) for intracellular receptors. In another aspect, the present invention relates to novel chimeric constructs and uses therefor.

BACKGROUND OF THE INVENTION

A central problem in eukaryotic molecular biology continues to be the elucidation of molecules and mechanisms that mediate specific gene regulation. As part of the scientific attack on this problem, a great deal of work has been done in efforts to identify ligands (i.e., exogenous inducers) which are capable of mediating specific gene regulation. Additional work has been done in efforts to identify other molecules involved in specific gene regulation.

Although much remains to be learned about the specifics of gene regulation, it is known that ligands modulate gene transcription by acting in concert with intracellular components, including intracellular receptors and discrete DNA sequences known as hormone response elements (HREs).

The identification of compounds that directly or indirectly interact with intracellular receptors, and thereby affect transcription of hormone-responsive genes, would be of significant value, e.g., for therapeutic applications.

Transcriptional silencing mediated by nuclear receptors plays an important role in development, cell differentiation, and is directly linked to the oncogenic activity of v-erbA. The mechanism underlying this effect is unknown but is one key to understanding the molecular basis of hormone action. Accordingly, the identification of components involved in transcriptional silencing would represent a great advance in current understanding of mechanisms that mediate specific gene regulation.

Other information helpful in the understanding and practice of the present invention can be found in commonly assigned U.S. Pat. Nos. 5,071,773, 4,981,784, 5,260,432, and 5,091,513, all of which are hereby incorporated herein by reference in their entirety.

BRIEF DESCRIPTION OF THE INVENTION

The present invention overcomes many problems in the art by providing a family of receptor interacting co-repressors, referred to herein as "SMRT co-repressor", i.e., a silencing mediator (co-repressor) for retinoic acid receptor (RAR) and thyroid hormone receptor (TR). In vivo, members of the SMRT family of co-repressors function as potent co-repressors. A GAL4 DNA binding domain (DBD) fusion with a SMRT co-repressor behaves as a frank repressor of a GAL4-dependent reporter. Together, these observations identify a novel family of cofactors that is believed to represent an important mediator of hormone action.

Accordingly, the present invention provides isolated silencing mediators of retinoic acid and thyroid hormone receptors, and isoforms or peptide portions thereof (SMRT co-repressors), that modulate transcriptional potential of members of the nuclear receptor superfamily. Such SMRT co-repressors comprise a repression domain having less than about 83% identity with a Sin3A interaction domain of N-CoR (amino acids 255 to 312 of SEQ ID NO: 11); less than about 57% identity with repression domain 1 of N-CoR (amino acids 1 to 312 of SEQ ID NO: 11); less than about 66% identity with a SANT domain of N-CoR (amino acids 312 to 668 of SEQ ID NO: 11) and/or; less than about 30% identity with repression domain 2 of N-CoR (amino acids 736 to 1031 of SEQ ID NO: 11). In accordance with yet another embodiment of the present invention, there are provided isolated peptides comprising at least a portion of the invention SMRT co-repressor six contiguous amino acids of an amino acid sequence selected from the group consisting of:

amino acids 1 to 1030 of SEQ ID NO: 5;
amino acids 1 to 1029 of SEQ ID NO: 7;
amino acids 1 to 809 of SEQ ID NO: 9;
and conservative variations thereof,
provided the peptide is not identical to a sequence of SEQ ID NO: 11.

In addition, there are provided isolated antibodies that bind specifically to invention isolated peptides. There are also provided chimeric molecules comprising invention isolated peptides and at least a second molecule. Also provided are complexes comprising an invention SMRT co-repressor and a member of the superfamily of nuclear receptors and isolated antibodies that bind to such complexes.

Accordingly, the present invention provides isolated polynucleotides encoding members of the newly described family of silencing mediators of retinoic acid and thyroid hormone receptor or an isoform or peptide portion thereof (SMRT co-repressor), or an isolated polynucleotide complementary thereto. In addition, there are provided vectors comprising invention polynucleotides, as well as host cells containing invention polynucleotides.

In additional embodiments of the present invention, there are provided methods for identifying agents that modulate the repressor potential of a SMRT co-repressor.

In another embodiment according to the present invention, there are provided methods for identifying an agent that modulates a function of an invention SMRT co-repressor.

In another embodiment according to the present invention, there are provided methods of modulating the transcriptional potential of a member of the nuclear receptor superfamily (nuclear receptor) in a cell.

In another embodiment according to the present invention, there are provided methods of identifying a molecule that interacts specifically with a SMRT co-repressor.

BRIEF DESCRIPTION OF THE FIGURES

FIG. 2 presents amino acid (aa) sequences of the first SMRT clone (Genbank accession number U37146; SEQ ID NO:1). The aa sequence presented in parentheses (i.e., residues 1330-1376) is an alternatively spliced insert which is not present in the original two-hybrid clone (C-SMRT, aa 981 to C-terminal end). The proline-rich N-terminal domain (aa 1-160) and the glutamine-rich region (aa 1061-1132), as well as the ERDR and SG regions, are also indicated. The C-terminal region of SMRT (aa 1201 to C-terminal end) shows 48% aa identity to RIP13 (Seol et al., *Molecular Endocrinology* 9:72-85 (1995)). The rest of the sequence of RIP13 shows 22% aa identity to SMRT (aa 819-1200).

FIG. 3(A) illustrates that v-erbA reverses the silencing effect of GAL-RAR (GAL4 DBD-hRARα 156-462) while SMRT restores the silencing effect.

FIG. 3(B) illustrates that the RAR403 truncation mutant reverses the silencing effect of GAL-TR (GAL4 DBD-hTRβ 173-456) while SMRT restores the silencing effect.

FIG. 3(C) illustrates that v-erbA and full length SMRT or C-SMRT have no effect on GAL-VP16 activity.

FIG. 3(D) illustrates that a GAL4 DBD fusion of full length SMRT represses the thymidine kinase basal promoter activity containing four GAL4 binding sites. The fold of repression was calculated by dividing the normalized luciferase activity transfected with the GAL4 DBD alone by those transfected with indicated amount of GAL DBD fusion constructs.

FIG. 4 provides an alignment of the human SMRT (SEQ ID NO: 5) and mouse SMRTα (SEQ ID NO: 7) amino acid sequences. Proteins were aligned using the CLUSTAL alignment program. Underlined sequence of mouse SMRTα corresponds to the amino acid sequences that are deleted in mouse SMRTβ. The arrow indicates the start point of the previously described human SMRT co-repressor (sSMRT).

FIGS. 5A and 5B provide alignments of the human SMRT (SEQ ID NO:5) and human N-CoR (SEQ ID NO: 11) co-repressors.

FIG. 9 shows sequence comparisons of SMRTER (SEQ ID NOs:18, 21, 32, 35, 38 and 39), SMRT (SEQ ID NOs:20, 23, 28, 33, 36 and 40-44), N-CoR (SEQ ID NOs:19, 22, 27, 34, 37 and 45-51), and other related proteins (SEQ ID NOs:24-26, 29-31 and 52). The SANT domains of various proteins are listed (SEQ ID NOs:21-31). Percentages of identity/similarity compared to SMRTER are shown on the right. Two potential helices are predicted in the N-terminal half of the SANT domain. Black boxes indicate identical sequences; gray boxes indicate similar or partially identical sequences.

FIG. 11A is a graph showing the interaction of ERID1 AND ERID2 with the EcR complex. FIG. 11B is a graph showing the results of competition between ERID1, ERID2 and c-SMRT for binding to EcR. FIG. 11C is a graph showing that EcR A483T disrupts the interaction with ERID1 and ERID2.

DETAILED DESCRIPTION OF THE INVENTION

Figure 1:
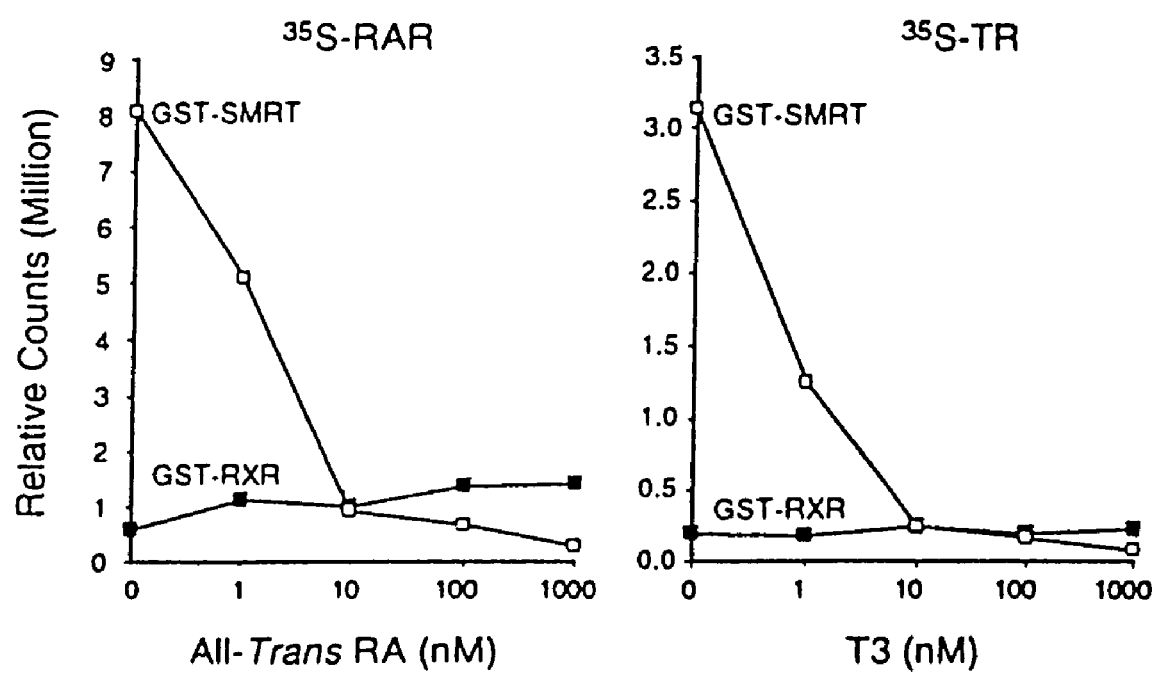
FIG. 1 shows the quantitation by phosphoimager of a dose-dependent dissociation of SMRT from RAR or TR by all-trans retinoic acid (atRA) or thyroid hormone (triiodothyronine or T3).

In accordance with the present invention, there is provided a family of isolated SMRT co-repressors, and isoforms and peptide portions thereof, that modulate transcriptional potential of members of the nuclear receptor superfamily. Exemplary members of this family are co-repressors having substantially the same sequence as residues 1-1329 plus 1376-1495, as set forth in SEQ ID NO: 1, optionally further comprising the amino acid residues set forth in SEQ ID NO:2 (i.e., residues 1330-1375 of SEQ ID NO:1).

In another embodiment according to the present invention, the invention SMRT co-repressor comprises a repression domain having less than about 83% identity with a Sin3A interaction domain of N-CoR (as amino acids 255 to 312 of SEQ ID NO: 11); less than about 57% identity with repression domain 1 of N-CoR (amino acids 1 to 312 of SEQ ID NO: 11); less than about 66% identity with a SANT domain of N-CoR (amino acids 312 to 668 of SEQ ID NO: 11 and/or; less than about 30% identity with repression domain 2 of N-CoR (amino acids 736 to 1031 of SEQ ID NO: 11). Such an encoded SMRT co-repressor or peptide portion thereof is further characterized in that it can modulate transcriptional potential of a member of the nuclear receptor superfamily (nuclear receptor).

The invention SMRT co-repressors are additionally exemplified by a full length human SMRT co-repressor, (amino acids 1 to 2517 of SEQ ID NO: 5); and by two mouse SMRT isoforms, including a longer SMRT isoform designated mouse SMRTA, which has an amino acid sequence set forth as amino acids 1 to 2473 of SEQ ID NO: 7; and a shorter SMRT isoform designated mouse SMRTβ (amino acids 1 to 2253 of SEQ ID NO: 9). As compared to the mouse SMRTα isoform (SEQ ID NO: 7), the mouse SMRTβ isoform (SEQ ID NO: 9) has a deletion corresponding to amino acids 36 to 254 of SEQ ID NO: 7.

A peptide portion of a SMRT co-repressor is exemplified herein by amino acids 1 to 1031 of SEQ ID NO: 5; amino acids 1 to 1031 of SEQ ID NO: 7; and amino acids 1 to 813 of SEQ ID NO: 9, which includes the entire amino terminal domain of a SMRT co-repressor. Additional peptide portions of a SMRT co-repressor are exemplified by amino acids 1 to 303 of SEQ ID NO: 7; amino acids 845 to 986 of SEQ ID NO: 7; amino acids 427 to 663 of SEQ ID NO: 7; amino acids 845 to 1055 of SEQ ID NO: 7; amino acids 736 to 1031 of SEQ ID NO: 7; and amino acids 1 to 85 of SEQ ID NO: 9, which are sub-domains of the amino terminal domain of mouse SMRTα that have nuclear receptor repressor potential, as well as by the corresponding peptide portions of human SMRT and corresponding peptide portions of mouse SMRTβ, which can modulate the transcriptional potential of a nuclear receptor, particularly a nuclear receptor that is in the form of a dimer, for example, a thyroid hormone receptor homodimer, a retinoic acid receptor homodimer, a retinoid X receptor homodimer, a thyroid hormone receptor-retinoid X receptor heterodimer, or a retinoic acid receptor-retinoid X receptor heterodimer. In addition, the invention relates to isolated peptides that contain at least six contiguous amino acids of an amino acid sequence set forth as amino acids 1 to 1030 of SEQ ID NO: 5; amino acids 1 to 1029 of SEQ ID NO: 5; or amino acids 1 to 809 of SEQ ID NO: 9, provided the SMRT peptide is not identical to a sequence of N-CoR (SEQ ID NO: 11).

Invention co-repressor can be an invertebrate SMRT co-repressor, such as the *Drosophilia* SMRTER co-repressor having an amino acid sequence as set forth in SEQ ID NO: 12, or conservative variations thereof.

Additional exemplary co-repressors are those containing one or both of the receptor interacting domains (ERID1 and ERID2) identified in the *Drosophilia* co-repressor. For example, co-repressors containing such receptor interacting domains can be selected from the following segments of the *Drosophilia* SMRTER co-repressor (SEQ. ID 12):
  amino acids 1698-1924 of SEQ. ID NO:12,
  amino acids 2951-3038 of SEQ. ID NO:12,
  amino acids 1698-2063 of SEQ. ID NO: 12,
  amino acids 2094-3040 of SEQ. ID NO: 12,
  amino acids 2929-3181 of SEQ. ID NO: 12,
  amino acids 542-950 of SEQ. ID NO:12,
  amino acids 2094-3181 of SEQ ID NO:12,
  amino acids 2929-3040 of SEQ ID NO:12, and
  amino acids 2951-3038 of SEQ ID NO: 12,
  and conservative variations thereof.

Additional exemplary co-repressors are those containing one or more of three autonomous repressor domains termed SMRD1, SMRD2, and SMRD3 identified in the SMRTER co-repressor. For example, invention co-repressors can contain the following autonomous repressor domains derived from *Drosophilia* SMRTER co-repressor (SEQ. ID 12):
  amino acids 542-950 of SEQ. ID NO: 12
  amino acids 1698-1924 of SEQ. ID NO:12,
  amino acids 2951-3038 of SEQ. ID NO: 12, and conservative variations thereof.

Conservative variations of the above-described SMRT co-repressors are also contemplated to be within the scope of the present invention. Moreover, proteins, polypeptides and peptides having at least 80% sequence identity with any of the SMRT co-repressors described herein are also contemplated to be within the scope of the invention.

In another embodiment according to the present invention, there are provided chimeric molecules comprising invention isolated peptides and at least a second molecule. For example, the second molecule in invention chimeric molecule can be a polynucleotide or a polypeptide. In one embodiment, the chimeric molecule is a fusion polypeptide comprising a SMRT co-repressor operably linked to a DNA binding domain of a transcription factor.

In another embodiment according to the present invention, there are provided isolated antibodies that bind specifically to invention isolated peptides. In one embodiment, an antibody of the invention binds specifically to an epitope of a SMRT co-repressor. Such an antibody is characterized, in part, in that it does not substantially crossreact with an N-CoR polypeptide. In another embodiment, an antibody of the invention binds specifically to a complex, which includes a SMRT co-repressor or peptide portion thereof of the invention, a nuclear receptor and, optionally, a DNA regulatory element that is specifically bound by the nuclear receptor. Such an antibody is characterized, in part, in that it does not substantially crossreact with the nuclear receptor, either alone or bound to the DNA regulatory element. An antibody of the invention can be a monoclonal antibody, or can be one of a plurality of polyclonal antibodies, which essentially is a mixed population of monoclonal antibodies. The invention also relates to a cell line, which produces the monoclonal antibody of the invention.

Such antibodies can be employed for a variety of purposes, e.g., for studying tissue localization of invention SMRT co-repressor, the structure of functional domains, the purification of receptors, as well as in diagnostic applications, therapeutic applications, and the like. Preferably, for therapeutic applications, the antibodies employed will be monoclonal antibodies.

The above-described antibodies can be prepared employing standard techniques, as are well known to those of skill in the art, using the invention SMRT co-repressor or portions thereof as antigens for antibody production. Both anti-peptide and anti-fusion protein antibodies can be used [see, for example, Bahouth et al. (1991) *Trends Pharmacol Sci.* vol. 12:338-343; *Current Protocols in Molecular Biology* (Ausubel et al., eds.) John Wiley and Sons, New York (1989). Factors to consider in selecting portions of invention SMRT co-repressor for use as immunogen (as either a synthetic peptide or a recombinantly produced bacterial fusion protein) include antigenicity, accessibility (i.e., where the selected portion is derived from, e.g., the ligand binding domain, DNA binding domain, dimerization domain, and the like), uniqueness of the particular portion selected (relative to known receptors and co-repressors therefor), and the like.

In another embodiment according to the present invention, there are provided complexes comprising an invention SMRT co-repressor and a member of the nuclear receptor superfamily and isolated antibodies that bind to such complexes. The nuclear receptor can be in the form of a monomer or dimer, for example, a thyroid hormone receptor homodimer, a retinoic acid receptor homodimer, a retinoid X receptor homodimer, a thyroid hormone receptor-retinoid X receptor heterodimer, a retinoic acid receptor-retinoid X receptor heterodimer, a ecdysone receptor-Ultraspiracle receptor heterodimer, and the like. Optionally or alternatively, the complex can include a DNA regulatory element, bound specifically by a DNA binding domain of the nuclear receptor.

The above-described complexes optionally further comprise a response element for the member of the nuclear receptor superfamily. Such response elements are well known in the art. Thus, for example, RAR response elements are composed of at least one direct repeat of two or more half sites separated by a spacer of five nucleotides. The spacer nucleotides can independently be selected from any one of A, C, G or T. Each half site of response elements contemplated for use in the practice of the invention comprises the sequence

-RGBNNM-, wherein
R is selected from A or G;
B is selected from G, C, or T;
each N is independently selected from A, T, C, or G; and
M is selected from A or C;

with the proviso that at least 4 nucleotides of said -RGBNNM- sequence are identical with the nucleotides at corresponding positions of the sequence -AGGTCA-. Response elements employed in the practice of the present invention can optionally be preceded by $N_x$, wherein x falls in the range of 0 up to 5.

Similarly, TR response elements can be composed of the same half site repeats, with a spacer of four nucleotides. Alternatively, palindromic constructs as have been described in the art are also functional as TR response elements.

The above-described SMRT co-repressor/dimeric receptor complexes can be dissociated by contacting the complex with a ligand for the member of the nuclear receptor superfamily.

As employed herein, the term "ligand (or ligand precursor) for a member of the nuclear receptor superfamily" (i.e., intracellular receptor) refers to a substance or compound which, in its unmodified form (or after conversion to its "active" form), inside a cell, binds to receptor protein, thereby creating a ligand/receptor complex, which in turn can activate an appropriate hormone response element. A ligand therefore is a compound which acts to modulate gene transcription for a gene maintained under the control of a hormone response element, and includes compounds such as hormones, growth substances, non-hormone compounds that modulate growth, and the like. Ligands include steroid or steroid-like hormone, retinoids, thyroid hormones, pharmaceutically active compounds, and the like. Individual ligands may have the ability to bind to multiple receptors.

Accordingly, as employed herein, "putative ligand" (also referred to as "test compound") refers to compounds such as steroid or steroid-like hormones, pharmaceutically active compounds, and the like, that are suspected to have the ability to bind to the receptor of interest, and to modulate transcription of genes maintained under the control of response elements recognized by such receptor.

In another embodiment according to the present invention, there are provided polynucleotides encoding members of the above-described family of silencing mediators of retinoic acid and thyroid hormone receptor, or an isoform or peptide portion thereof (SMRT co-repressors), or an isolated polynucleotide complementary thereto.

Invention polynucleotides include those encoding a SMRT co-repressor comprises a repression domain having
a) less than about 83% identity with a Sin3A interaction domain of N-CoR set forth as amino acids 255 to 312 of SEQ ID NO: 11;
b) less than about 57% identity with repression domain 1 of N-CoR set forth as amino acids 1 to 312 of SEQ ID NO: 11;
c) less than about 66% identity with a SANT domain of N-CoR set forth as amino acids 312 to 668 of SEQ ID NO: 11; or
d) less than about 30% identity with repression domain 2 of N-CoR set forth as amino acids 736 to 1031 of SEQ ID NO: 11.

In addition, an invention polynucleotide can encode a mouse SMRTβ isoform having an amino acid sequence as set forth in SEQ ID NO: 9 or conservative variations thereof, or a polynucleotide having a nucleotide sequence as set forth in SEQ ID NO: 8.

Further examples of invention polynucleotides are those comprising a nucleotide sequence selected from the group consisting of:
nucleotides 1 to 3094 of SEQ ID NO: 4;
nucleotides 1 to 3718 of SEQ ID NO: 6;
nucleotides 1 to 2801 of SEQ ID NO: 8;
nucleotides 1 to 8388 of SEQ ID NO: 6;
nucleotides 1 to 7465 of SEQ ID NO: 8; and
nucleotides 1 to 8561 of SEQ ID NO: 4.

The invention polynucleotides further comprise those encoding a human SMRT co-repressor having an amino acid sequence as set forth in SEQ ID NO: 5, for example, a nucleotide sequence as set forth in SEQ ID NO: 4; by a polynucleotide encoding a mouse SMRTα isoform having an amino acid sequence as set forth in SEQ ID NO: 7, for example, a nucleotide sequence as set forth in SEQ ID NO:

6; and by a polynucleotide encoding a mouse SMRTβ isoform having an amino acid sequence as set forth in SEQ ID NO: 9, for example, a nucleotide sequence as set forth in SEQ ID NO: 8. A polynucleotide of the invention is further exemplified by polynucleotides encoding peptide portions of a SMRT co-repressor such as a polynucleotide containing nucleotides 1 to 3094 of SEQ ID NO: 4; nucleotides 1 to 3718 of SEQ ID NO: 7; or nucleotides 1 to 2801 of SEQ ID NO: 8, which can repress the transcriptional activity of nuclear receptor, particularly a nuclear receptor that is in the form of dimer.

Additional invention polynucleotides include those encoding a full length insect SMRTER co-repressor having an amino acid sequence as set forth in SEQ ID NO: 12, or conservative variations thereof.

Additional exemplary invention polynucleotides are those encoding one or both of the receptor interacting domains (ERID1 and ERID2) identified in invention co-repressors. For example, polynucleotides encoding such receptor interacting domains can be selected from those encoding the following segments of the Drosophilia SMRTER co-repressor (SEQ. ID 12):
  amino acids 1698-1924 of SEQ. ID NO: 12,
  amino acids 2951-3038 of SEQ. ID NO: 12,
  amino acids 1698-2063 of SEQ. ID NO:12,
  amino acids 2094-3040 of SEQ. ID NO:12,
  amino acids 2929-3181 of SEQ. ID NO:12,
  amino acids 542-950 of SEQ. ID NO:12,
  amino acids 2094-3181 of SEQ ID NO:12,
  amino acids 2929-3040 of SEQ ID NO:12, and
  amino acids 2951-3038 of SEQ ID NO:12,
  and conservative variations thereof.

Additional exemplary invention polynucleotides are those encoding one or more of three autonomous repressor domains termed SMRD1, SMRD2, and SMRD3 identified in the invention co-repressors. For example, polynucleotides encoding such autonomous repressor domains can be selected from those encoding the following segments of the Drosophilia SMRTER co-repressor (SEQ. ID 12):
  amino acids 542-950 of SEQ. ID NO:12
  amino acids 1698-1924 of SEQ ID NO:12,
  amino acids 2951-3038 of SEQ. ID NO:12, and conservative variations thereof.

A polynucleotide that has at least 80% sequence identity or that hybridizes, (preferably under high stringency conditions) with any one of the above-described polynucleotides is also contemplated to be within the scope of this invention.

A polynucleotide of the invention can be operably linked to a second nucleotide sequence and, therefore, can encode a fusion polypeptide, for example, a SMRT co-repressor, or peptide portion thereof, operably linked to a DNA binding domain of a transcription factor.

Additional examples of invention isolated oligonucleotides, are those which generally are at least about 15 nucleotides in length and can hybridize specifically to the polynucleotide of the invention, but not to a polynucleotide encoding an N-CoR polypeptide (SEQ ID NO: 11). An oligonucleotide of the invention can be useful as a probe, or as a primer for a PCR procedure, or can encode a peptide containing at least five contiguous amino acids of a SMRT co-repressor. In one embodiment, an oligonucleotide of the invention encodes at least five contiguous amino acids of a sequence such as that shown as amino acids 720 to 745 of SEQ ID NO: 5; or amino acids 716 to 742 of SEQ ID NO: 7; or amino acids 497 to 523 of SEQ ID NO: 9. In another embodiment, an oligonucleotide of the invention can hybridize specifically to a polynucleotide encoding human SMRT (SEQ ID NO: 5) or mouse SMRTα (SEQ ID NO: 7), and, optionally, to a polynucleotide encoding mouse SMRTβ (SEQ ID NO: 9).

The phrase "substantially the same" as used herein in reference to a nucleotide sequence of DNA, a ribonucleotide sequence of RNA, or an amino acid sequence of protein, means sequences that have slight and non-consequential sequence variations from the actual sequences disclosed herein. Species that are substantially the same are considered to be equivalent to the disclosed sequences and as such are within the scope of the appended claims. In this regard, "slight and non-consequential sequence variations" means that sequences substantially the same as the DNA, RNA, or proteins disclosed and claimed herein are functionally equivalent to the sequences disclosed and claimed herein. Functionally equivalent sequences will function in substantially the same manner to produce substantially the same compositions as the nucleic acid and amino acid compositions disclosed and claimed herein. In particular, functionally equivalent DNAs encode proteins that are the same as those disclosed herein or that have conservative amino acid variations, such as substitution of a non-polar residue for another non-polar residue or a charged residue for a similarly charged residue. These changes include those recognized by those of skill in the art as those that do not substantially alter the tertiary structure of the protein.

In another embodiment according to the present invention, there are provided vectors comprising an invention polynucleotide, and host cells containing invention polynucleotides. The invention vector can be an expression vector, including, for example, a viral vector, and the polynucleotide, or a vector containing the polynucleotide, can be contained in a host cell. In one embodiment, the polynucleotide of the invention is operably linked to a tissue specific DNA regulatory element. In another embodiment, a SMRT co-repressor or peptide portion thereof encoded by the polynucleotide is expressed in a host cell.

In another embodiment according to the present invention, there are provided methods for identifying an agent that modulates the repressor potential of a SMRT co-repressor. In this embodiment, the invention method comprises contacting a host cell with an agent, and detecting a change in the level of expression of a first expressible nucleotide sequence in response to the agent, thereby identifying an agent that modulates the repressor potential of a SMRT co-repressor. In such a method, the host cell is characterized, in part, in that it contains a first expressible nucleotide sequence operably linked to a first DNA regulatory element, and expresses a fusion polypeptide composed of an invention SMRT co-repressor, or peptide portion thereof, and a DNA binding domain of a first transcription factor that can specifically bind the first DNA regulatory element. Binding of the DNA binding domain of the first transcription factor to the first DNA regulatory element results in expression of the first expressible nucleotide sequence in the host cell.

In another embodiment according to the present invention, there are provided methods for identifying an agent that modulates a function of an invention SMRT co-repressor. In this embodiment, the invention method comprises contacting an invention SMRT co-repressor, a member of the nuclear receptor superfamily, and an agent, and detecting an altered activity of the SMRT co-repressor in the presence of the agent as compared to the absence of the agent, thereby identifying an agent that modulates a function of the SMRT co-repressor.

A method of the invention can be performed, for example, by contacting a host cell with an agent, and detecting a change in the level of expression of a first expressible nucleotide sequence in response to the agent, thereby identifying an agent that modulates the repressor potential of a SMRT co-repressor. In such a method, the host cell is characterized, in part, in that it contains a first expressible nucleotide sequence operably linked to a first DNA regulatory element, and expresses a fusion polypeptide composed of a SMRT co-repressor or peptide portion thereof of the invention, and a DNA binding domain of a first transcription factor, which can specifically bind the first DNA regulatory element; binding of the DNA binding domain of the first transcription factor to the first DNA regulatory element results in expression of the first expressible nucleotide sequence in the host cell. The first expressible nucleotide sequence can be an endogenous gene, which is normally present in the host cell, or can be a sequence that has been introduced into the host cell, either transiently or stably, using methods of recombinant DNA technology. In one embodiment, the first DNA binding domain is a GAL4 DNA binding domain and the first DNA regulatory element is a GAL4 DNA regulatory element that is operably linked to an expressible nucleotide sequence, for example, a reporter gene, and is introduced into the host cell.

Thus, the invention method can identify an agent that increases or decreases the repressor potential of the SMRT co-repressor, or of an agent that increases or decreases the function of the SMRT co-repressor. The agent can directly interact with the SMRT co-repressor or peptide portion thereof, thereby modulating the repressor potential or function of the SMRT co-repressor, or can interact with a cellular molecule that, in turn, can alter the repressor potential or function of a SMRT co-repressor, thereby increasing or decreasing the repressor potential of the SMRT co-repressor.

The host cell can optionally contain a second expressible nucleotide sequence operably linked to a second DNA regulatory element, and can express a second fusion polypeptide, which is composed of an N-CoR polypeptide, or a repressor domain thereof, and a DNA binding domain of a second transcription factor, which can specifically bind the second DNA regulatory element. By comparing the level of expression of the first expressible nucleotide sequence and the second expressible nucleotide sequence in the host cell upon contacting the host cell with the agent, an agent that independently or coordinately modulates SMRT and N-CoR repressor activity. For example, detecting a change in the level of expression of the first expressible nucleotide sequence, but not in the level of expression of the second expressible nucleotide sequence, due to contacting the host cell with the agent identifies an agent that modulates the repressor potential of a SMRT co-repressor, but not of an N-CoR polypeptide can be identified.

In practicing a method of the invention, the SMRT co-repressor, or peptide portion thereof, can be, for example, an amino acid sequence such as amino acids 1 to 1031 of SEQ ID NO: 5; amino acids 1 to 1031 of SEQ ID NO: 7; or amino acids 1 to 813 of SEQ ID NO: 9. The agent can be, for example, an antibody or antigen binding fragment thereof, a peptide, or a small organic molecule.

In another embodiment according to the present invention, there are provided methods of modulating the transcriptional potential of a member of the nuclear receptor superfamily (nuclear receptor) in a cell, the method comprising introducing an invention isolated polynucleotide into the cell, whereby the polynucleotide or an expression product of the polynucleotide alters the level of a SMRT co-repressor in the cell, thereby modulating the transcriptional potential of the nuclear receptor.

In another embodiment according to the present invention, there are provided methods of modulating the transcriptional potential of a member of the nuclear receptor superfamily (nuclear receptor) in a cell, the method comprising introducing an invention isolated polynucleotide into the cell, whereby the polynucleotide or an expression product of the polynucleotide alters the level of a SMRT co-repressor in the cell, thereby modulating the transcriptional potential of the nuclear receptor.

In performing a method of the invention, an agent that alters an interaction of the SMRT co-repressor, or peptide portion thereof, with the nuclear receptor can be identified using a binding assay, such as an electrophoretic mobility shift assay wherein the level of expression of an expressible nucleotide sequence. Such a method can also identify an agent that alters the ability of the invention SMRT co-repressor, or peptide portion thereof, to interact specifically with the nuclear receptor, but does not alter the level of expression of the expressible nucleotide sequence; or an agent that alters the level of expression of the expressible nucleotide sequence, but does not alter interaction of the SMRT co-repressor or peptide portion thereof with the nuclear receptor; or an agent that alters an interaction of the SMRT co-repressor, or peptide portion thereof, with the nuclear receptor and alters the level of expression of the expressible nucleotide sequence. The agent can, but need not be, a ligand for the nuclear receptor, and the method can be performed in a cell or in a reaction mixture in vitro.

Alternatively, an invention polynucleotide can be introduced into the cell, whereby the polynucleotide, or an expression product of the polynucleotide, alters the level of a SMRT co-repressor in the cell, thereby modulating the transcriptional potential of the nuclear receptor. The polynucleotide can encode an invention SMRT co-repressor or peptide, portion thereof, which can be expressed in the cell, thereby increasing the level of a SMRT co-repressor, or peptide portion thereof, in the cell. The polynucleotide also can be an antisense polynucleotide, that decreases the level of a SMRT co-repressor in the cell.

In another embodiment according to the present invention, there are provided methods of identifying a molecule that interacts specifically with a SMRT co-repressor. In this embodiment, invention methods comprise contacting the molecule with an invention SMRT co-repressor and detecting specific binding of the molecule to the SMRT co-repressor, thereby identifying a molecule that interacts specifically with a SMRT co-repressor.

The molecule can be any molecule that interacts specifically with a SMRT co-repressor, including, for example, a small organic molecule such as a drug, a peptide, a nucleic acid molecule, and the like. In one embodiment, the molecule is a cellular factor, for example, a cellular protein that modulates the ability of a SMRT co-repressor to repress transcriptional activity of a nuclear receptor. In another embodiment, the method further involves isolating the molecule that interacts specifically with the SMRT co-repressor or peptide portion thereof.

In accordance with yet another aspect of the present invention, there are provided methods to block the repressing effect of invention SMRT co-repressors, said method comprising administering an effective amount of an antibody as described herein. Alternatively, a silencing domain of a nuclear receptor can be employed. Those of skill in the art can readily determine suitable methods for administering said antibodies, and suitable quantities for administration, which will vary depending on numerous factors, such as the indication being treated, the condition of the subject, and the like.

In accordance with another aspect of the present invention, there is provided a method to repress (or silence) the activity of a member of the nuclear receptor superfamily containing a silencing domain that represses basal level promoter activity of target genes, said method comprising contacting said member of the nuclear receptor superfamily with a sufficient quantity of an invention SMRT co-repressor so as to repress the activity of said member. Members of the nuclear receptor superfamily contemplated for repression in accordance with this aspect of the present invention include, for example, thyroid hormone receptor, retinoic acid receptor, vitamin D receptor, peroxisome proliferator activated receptor, and the like.

In accordance with yet another aspect of the present invention, there is provided a method to identify compounds which relieve the repression of nuclear receptor activity caused by an invention SMRT co-repressor, said method comprising comparing the size of the SMRT co-repressor/dimeric receptor complex (i.e., complexes comprising the invention SMRT co-repressor and a homodimeric or heterodimeric member of the nuclear receptor superfamily) upon exposure to test compound, relative to the size of said complex in the absence of test compound. An observed size corresponding to intact complex is indicative of an inactive compound, while an observed size that reflects dissociation of the complex is indicative of a compound that disrupts the complex, thereby relieving the repression caused thereby. Optionally, the complex employed in this assay further comprises a response element for said member of the nuclear receptor superfamily.

The size of the above-described complex can readily be determined employing various techniques available in the art. For example, electrophoretic mobility shift assays (EMSA) can be employed (wherein receptor alone or receptor-SMRT co-repressor complex is bound to target DNA and the relative mobility thereof determined). Those of skill in the art can readily identify other methodology which can be employed to determine the size of the complex as a result of exposure to putative ligand.

In accordance with a still further aspect of the present invention, there is provided a method to identify compounds which relieve the repression of nuclear receptor activity caused by an invention SMRT co-repressor, without substantially activating said receptor, said method comprising:

comparing the reporter signal produced by two different expression systems in the absence and presence of test compound, wherein said first expression system comprises a complex comprising:

a homodimeric or heterodimeric member of the nuclear receptor superfamily selected from thyroid hormone receptor homodimer, thyroid hormone receptor-retinoid X receptor heterodimer, retinoic acid receptor homodimer, or retinoic acid receptor-retinoid X receptor heterodimer, a response element for said member of the nuclear receptor superfamily, wherein said response element is operatively linked to a reporter gene, and optionally, invention SMRT co-repressor, and wherein said second expression system comprises a complex comprising:

a homodimeric or heterodimeric form of the same member of the nuclear receptor superfamily as employed in said first expression system, wherein said member is mutated such that it retains hormone dependent activation activity but has lost its ability to repress basal level promoter activity of target genes, the same response element-reporter combination as employed in said first expression system, and optionally, invention SMRT co-repressor, and thereafter selecting those compounds which provide:

a higher reporter signal upon exposure of said compound to said first expression system, relative to reporter signal in the absence of said compound, and substantially the same reporter signal upon exposure of said compound to said second expression system, relative to reporter signal in the absence of said compound, wherein said selected compounds are capable of relieving the repression of nuclear receptor activity caused by a SMRT co-repressor having a structure and function characteristic of an invention SMRT co-suppressor but substantially lacking the ability to activate nuclear receptor activity.

The addition of invention SMRT co-repressor is optional in the above-described assay because it is present endogenously in most host cells employed for such assays. It is preferred, to ensure the presence of a fairly constant amount of SMRT co-repressor, and to ensure that SMRT co-repressor is not a limiting reagent, that SMRT co-repressor be supplied exogenously to the above-described assays.

Mutant receptors contemplated for use in the practice of the present invention are conveniently produced by expression plasmids, introduced into the host cell by transfection. Mutant receptors contemplated for use herein include RAR403 homodimers, RAR403-containing heterodimers, TR160 homodimers, TR160-containing heterodimers, and the like.

Reporter constructs contemplated for use in the practice of the present invention comprise:

(a) a promoter that is operable in the host cell,
(b) a hormone response element, and
(c) a DNA segment encoding a reporter protein,
   wherein the reporter protein-encoding DNA segment is operatively linked to the promoter for transcription of the DNA segment, and
   wherein the hormone response element is operatively linked to the promoter for activation thereof.

Hormone response elements contemplated for use in the practice of the present invention are well known in the art, as has been noted previously.

Exemplary reporter genes include chloramphenicol transferase (CAT), luciferase (LUC), beta-galactosidase (β-gal), and the like. Exemplary promoters include the simian virus (SV) promoter or modified form thereof (e.g., SV), the thymidine kinase (TK) promoter, the mammary tumor virus (MTV) promoter or modified form thereof (e.g., ΔMTV), and the like [see, for example, Mangelsdorf et al., in Nature 345:224-229 (1990), Mangelsdorf et al., in Cell 66:555-561 (1991), and Berger et al., in J. Steroid Biochem. Molec. Biol. 41:733-738 (1992).

As used herein in the phrase "operative response element" or "operatively linked" the word "operative" means that the respective DNA sequences (represented by the terms "GAL4 response element" and "reporter gene") are operational, i.e., work for their intended purposes; such that after the two segments are linked, upon appropriate activation by a ligand-receptor complex, the reporter gene will be expressed as the result of the fact that the "GAL4 response element" was "turned on" or otherwise activated.

In practicing the above-described functional bioassay, the expression plasmid and the reporter plasmid are co-transfected into suitable host cells. The transfected host cells are then cultured in the presence and absence of a test compound to determine if the test compound is able to produce activation of the promoter operatively linked to the response element of the reporter plasmid. Thereafter, the transfected and cultured host cells are monitored for induction (i.e., the presence) of the product of the reporter gene sequence.

Any cell line can be used as a suitable "host" for the functional bioassay contemplated for use in the practice of the present invention. Thus, cells contemplated for use in the practice of the present invention include transformed cells, non-transformed cells, neoplastic cells, primary cultures of different cell types, and the like. Exemplary cells which can be employed in the practice of the present invention include Schneider cells, CV-1 cells, HuTu80 cells, F9 cells, NTERA2 cells, NB4 cells, HL-60 cells, 293 cells, Hela cells, yeast cells, and the like. Preferred host cells for use in the functional bioassay system are COS cells and CV-1 cells. COS-1 (referred to as COS) cells are monkey kidney cells that express SV40 T antigen (Tag); while CV-1 cells do not express SV40 Tag. The presence of Tag in the COS-1 derivative lines allows the introduced expression plasmid to replicate and provides a relative increase in the amount of receptor produced during the assay period. CV-1 cells are presently preferred because they are particularly convenient for gene transfer studies and provide a sensitive and well-described host cell system.

The above-described cells (or fractions thereof) are maintained under physiological conditions when contacted with physiologically active compound. "Physiological conditions" are readily understood by those of skill in the art to comprise an isotonic, aqueous nutrient medium at a temperature of about 37° C.

In accordance with yet another aspect of the present invention, there is provided a method to identify compounds which activate nuclear receptor activity, but substantially lack the ability to relieve the repression caused by an invention SMRT co-repressor, said method comprising:

comparing the reporter signal produced by two different expression systems in the absence and presence of test compound,
wherein said first expression system comprises a complex comprising:
a homodimeric or heterodimeric member of the nuclear receptor superfamily selected from thyroid hormone receptor homodimer, thyroid hormone receptor-retinoid X receptor heterodimer, retinoic acid receptor homodimer, or retinoic acid receptor-retinoid X receptor heterodimer,
a response element for said member of the nuclear receptor superfamily, wherein said response element is operatively linked to a reporter, and
optionally, invention SMRT co-repressor, and
wherein said second expression system comprises a complex comprising:
a homodimeric or heterodimeric form of the same member of the nuclear receptor superfamily as employed in said first expression system, wherein said member is mutated such that it retains hormone dependent activation activity but has lost its ability to repress basal level promoter activity of target genes,
the same response element-reporter combination as employed in said first expression system, and
optionally, invention SMRT co-repressor, and thereafter selecting those compounds which provide:
a higher reporter signal upon exposure of said compound to said second expression system, relative to reporter signal in the absence of compound, and
substantially the same reporter signal upon exposure of said compound to said first expression system, relative to reporter signal in the absence of said compound,
wherein said selected compounds are capable of activating nuclear receptor activity, but substantially lacking the ability to relieve the repression caused by a SMRT co-repressor having a structure and function characteristic of, an invention SMRT co-repressor for retinoic acid and thyroid receptors.

In accordance with a still further aspect of the present invention, there is provided a method to identify compounds which relieve the repression of nuclear receptor activity caused by an invention SMRT co-repressor, and activate said receptor, said method comprising:

comparing the reporter signal produced by two different expression systems in the absence and presence of test compound,
wherein said first expression system comprises a complex comprising:
a homodimeric or heterodimeric member of the nuclear receptor superfamily selected from thyroid hormone receptor homodimer, thyroid hormone receptor-retinoid X receptor heterodimer, retinoic acid receptor homodimer, or retinoic acid receptor-retinoid X receptor heterodimer,
a response element for said member of the nuclear receptor superfamily, wherein said response element is operatively linked to a reporter, and
optionally, invention SMRT co-repressor, and
wherein said second expression system comprises a complex comprising:
a homodimeric or heterodimeric form of the same member of the nuclear receptor superfamily as employed in said first expression system, wherein said member is mutated such that it retains hormone dependent activation activity but has lost its ability to repress basal level promoter activity of target genes,
the same response element-reporter combination as employed in said first expression system, and
optionally, invention SMRT co-repressor, and thereafter
selecting those compounds which provide:
increased reporter signal upon exposure of said compound to said second expression system, relative to reporter signal in the absence of said compound, and
substantially increased reporter signal upon exposure of said compound to said first expression system, relative to reporter signal in the absence of said compound,
wherein said selected compounds are capable of relieving the repression of nuclear receptor activity caused by a SMRT co-repressor having a structure and function characteristic of the silencing mediator for retinoic acid and thyroid receptors, and activating said receptor.

In accordance with still another embodiment of the present invention, there are provided modified forms of the above-described SMRT co-repressor, including:
full length silencing mediator for retinoic acid and thyroid receptors plus GAL4 DNA binding domain,
full length silencing mediator for retinoic acid and thyroid receptors plus GAL4 activation domain,
full length silencing mediator for retinoic acid and thyroid receptors plus glutathione S-transferase (GST) tag,
and the like.

The above-described modified forms of invention SMRT co-repressor can be used in a variety of ways, e.g., in the assays described herein.

An especially preferred modified SMRT co-repressor of the invention comprises full length silencing mediator for retinoic acid and thyroid receptors plus GAL4 activation domain.

In accordance with a still further embodiment of the present invention, there is provided a method to identify compounds which disrupt the ability of an invention SMRT co-repressor to complex with nuclear receptors, without substantially activating said receptor, said method comprising:

comparing the reporter signal produced by two different expression systems in the absence and presence of test compound,
wherein said first expression system comprises a complex comprising:
a modified SMRT co-repressor as described above,
a homodimeric or heterodimeric member of the nuclear receptor superfamily selected from thyroid hormone receptor homodimer, thyroid hormone receptor-retinoid X receptor heterodimer, retinoic acid receptor homodimer or retinoic acid receptor-retinoid X receptor heterodimer, and
a response element for said member of the nuclear receptor superfamily, wherein said response element is operatively linked to a reporter, and
wherein said second expression system comprises a complex comprising:
said modified SMRT co-repressor,
a homodimeric or heterodimeric form of the same member of the nuclear receptor superfamily as employed in said first expression system, wherein said member is mutated such that it retains hormone dependent activation activity but has lost its ability to repress basal level promoter activity of target genes, and
the same response element-reporter combination as employed in said first expression system, and thereafter
selecting those compounds which provide:
a lower reporter signal upon exposure of said compound to said first expression system, relative to reporter signal in the absence of said compound, and
substantially the same reporter signal upon exposure of said compound to said second expression system, relative to reporter signal in the absence of said compound,
wherein said selected compounds are capable of disrupting the ability of a SMRT co-repressor having a structure and function characteristic of the silencing mediator for retinoic acid and thyroid receptors to complex with nuclear receptors, without substantially activating said receptor.

Mutant receptors contemplated for use in this embodiment of the present invention include RAR403 homodimers, RAR403-containing heterodimers, TR160 homodimers, TR160-containing heterodimers, and the like.

Suitable host cells for use in this embodiment of the present invention include mammalian cells as well as yeast cells. Yeast cells are presently preferred because they introduce no background since SMRT (i.e., silencing mediator (SMRT co-repressor) for retinoic acid receptor (RAR) and thyroid hormone receptor (TR)) is not endogenous to yeast.

In accordance with yet another embodiment of the present invention, there is provided a method to identify compounds which activate nuclear receptor activity, but substantially lack the ability to disrupt a complex comprising a nuclear receptor and an invention SMRT co-repressor, said method comprising:

comparing the reporter signal produced by two different expression systems in the absence and presence of test compound,
wherein said first expression system comprises a complex comprising:
a modified SMRT co-repressor as described above,
a homodimeric or heterodimeric member of the nuclear receptor superfamily selected from thyroid hormone receptor homodimer, thyroid hormone receptor-retinoid X receptor heterodimer, retinoic acid receptor homodimer or retinoic acid receptor-retinoid X receptor heterodimer, and
a response element for said member of the nuclear receptor superfamily, wherein said response element is operatively linked to a reporter, and
wherein said second expression system comprises:
said modified SMRT co-repressor,
a homodimeric or heterodimeric form of the same member of the nuclear receptor superfamily as employed in said first expression system, wherein said member is mutated such that it retains hormone dependent activation activity but has lost its ability to repress basal level promoter activity of target genes, and
the same response element-reporter combination as employed in said first expression system, and thereafter
selecting those compounds which provide:
a higher reporter signal upon exposure of said compound to said second expression system, relative to reporter signal in the absence of compound, and
substantially the same reporter signal upon exposure of said compound to said first expression system, relative to reporter signal in the absence of compound,
wherein said selected compounds are capable of activating nuclear receptor activity, but substantially lack the ability to disrupt the complex of an invention SMRT co-repressor.

Suitable host cells for use in this embodiment of the present invention include mammalian cells as well as yeast cells. Yeast cells are presently preferred because they introduce no background since SMRT is not endogenous to yeast.

In accordance with a still further embodiment of the present invention, there is provided a method to identify compounds which activate a nuclear receptor, and disrupt the ability of an invention SMRT co-repressor to complex with said receptor, said method comprising:

comparing the reporter signal produced by two different expression systems in the absence and presence of test compound,
wherein said first expression system comprises a complex comprising:
a modified SMRT co-repressor as described above,
a homodimeric or heterodimeric member of the nuclear receptor superfamily selected from thyroid hormone receptor homodimer, thyroid hormone receptor-retinoid X receptor heterodimer, retinoic acid receptor homodimer or retinoic acid receptor-retinoid X receptor heterodimer, and
a response element for said member of the nuclear receptor superfamily, wherein said response element is operatively linked to a reporter, and
wherein said second expression system comprises a complex comprising:

said modified SMRT co-repressor,
the same homodimeric or heterodimeric member of the nuclear receptor superfamily as employed in said first expression system, wherein said member is mutated such that it retains hormone dependent activation activity but has lost its ability to repress basal level promoter activity of target genes, and
the same response element-reporter combination as employed in said first expression system, and thereafter
selecting those compounds which provide:
a reduction in reporter signal upon exposure of compound to said first expression system, relative to reporter signal in the absence of said compound, and
increased reporter signal upon exposure of compound to said second expression system, relative to reporter signal in the absence of said compound,
wherein said selected compounds are capable of activating a nuclear receptor and disrupting a complex comprising nuclear receptor and a SMRT co-repressor having a structure and function characteristic of the silencing mediator for retinoic acid and thyroid receptors.

Suitable host cells for use in this embodiment of the present invention include mammalian cells as well as yeast cells. Yeast cells are presently preferred because they introduce no background since SMRT is not endogenous to yeast.

In accordance with yet another aspect of the present invention, there is provided a method to identify compounds which activate a nuclear receptor and/or disrupt the ability of an invention SMRT co-repressor to complex with said receptor, said method comprising:
comparing the reporter signals produced by a combination expression system in the absence and presence of test compound,
wherein said combination expression system comprises:
a first homodimeric or heterodimeric member of the nuclear receptor superfamily selected from thyroid hormone receptor homodimer, thyroid hormone receptor-retinoid X receptor heterodimer, retinoic acid receptor homodimer, or retinoic acid receptor-retinoid X receptor heterodimer,
a second homodimeric or heterodimeric form of the same member of the nuclear receptor superfamily as employed in said first homodimer or heterodimer, wherein said member is mutated such that it retains hormone dependent activation activity but has lost its ability to repress basal level promoter activity of target genes (i.e., provides basal level expression), wherein either said first homodimer (or heterodimer) or said second homodimer (or heterodimer) is operatively linked to a GAL4 DNA binding domain,
a response element for said member of the nuclear receptor superfamily, wherein said response element is operatively linked to a first reporter,
a GAL4 response element, wherein said response element is operatively linked to a second reporter, and
optionally a SMRT co-repressor of nuclear receptor activity, said SMRT co-repressor having a structure and function characteristic of the silencing mediator for retinoic acid and thyroid receptors, and thereafter
identifying as capable of relieving the repression of nuclear receptor activity caused by a SMRT co-repressor having a structure and function characteristic of the silencing mediator for retinoic acid and thyroid receptors, but substantially lacking the ability to activate nuclear receptor activity those compounds which provide:
a higher reporter signal from the reporter responsive to the first member upon exposure of said compound to said first member, relative to reporter signal in the absence of said compound, and
substantially the same reporter signal from the reporter responsive to the second member upon exposure of said compound to said second member, relative to reporter signal in the absence of said compound, or
identifying as capable of activating nuclear receptor activity, but substantially lacking the ability to relieve the repression caused by a SMRT co-repressor having a structure and function characteristic of the silencing mediator for retinoic acid and thyroid receptors those compounds which provide:
a higher reporter signal from the reporter responsive to the second member upon exposure of said compound to said second member, relative to reporter signal in the absence of compound, and
substantially the same reporter signal from the reporter responsive to the first member upon exposure of said compound to said first member, relative to reporter signal in the absence of said compound, or
identifying as capable of relieving the repression of nuclear receptor activity caused by a SMRT co-repressor having a structure and function characteristic of the silencing mediator for retinoic acid and thyroid receptors, and activating said receptor those compounds which provide:
a higher reporter signal from the reporter responsive to the second member upon exposure of said compound to said second member, relative to reporter signal in the absence of said compound, and
a greater increase in reporter signal from the reporter responsive to the first member upon exposure of said compound to said first member, relative to reporter signal in the absence of said compound.

Thus, the change in expression level of the two different reporters introduced in a single transfection can be monitored simultaneously. Based on the results of this single transfection, one can readily identify the mode of interaction of test compound with the receptor/SMRT complex.

Exemplary GAL4 response elements are those containing the palindromic 17-mer:

5'-CGGAGGACTGTCCTCCG-3' (SEQ ID NO:3), such as, for example, 17MX, as described by Webster et al., in *Cell* 52:169-178 (1988), as well as derivatives thereof. Additional examples of suitable response elements include those described by Hollenberg and Evans in *Cell* 55:899-906 (1988); or Webster et al. in *Cell* 54:199-207 (1988).

In accordance with still another embodiment of the present invention, there is provided a method to identify compounds which activate a nuclear receptor and/or disrupt the ability of an invention SMRT co-repressor to complex with said receptor, said method comprising:
comparing the reporter signals produced by a combination expression system in the absence and presence of test compound,
wherein said combination expression system comprises:
a modified SMRT co-repressor as described above,
a first homodimeric or heterodimeric member of the nuclear receptor superfamily selected from thyroid hormone receptor homodimer, thyroid hormone receptor-retinoid X receptor heterodimer, retinoic acid receptor homodimer, or retinoic acid receptor-retinoid X receptor heterodimer,
a second homodimeric or heterodimeric form of the same member of the nuclear receptor superfamily as employed in said first homodimer or heterodimer, wherein said member is mutated such that it retains hormone dependent activation activity but has lost its ability to repress basal level promoter activity of target genes, wherein either said first homodimer (or heterodimer) or said second homodimer (or heterodimer) is operatively linked to a GAL4 DNA binding domain, a response element for said member of the nuclear receptor superfamily, wherein said response element is operatively linked to a first reporter, a GAL4 response element, wherein said response element is operatively linked to a second reporter, and thereafter identifying as capable of disrupting the ability of a SMRT co-repressor having a structure and function characteristic of the silencing mediator for retinoic acid and thyroid receptors to complex with a nuclear receptor, without substantially activating nuclear receptor, those compounds which provide:

a lower reporter signal from the reporter responsive to the first member upon exposure of said compound to said first member, relative to reporter signal in the absence of said compound, and substantially the same reporter signal from the reporter responsive to the second member upon exposure of said compound to said second member, relative to reporter signal in the absence of said compound, or identifying as capable of activating nuclear receptor activity, but substantially lacking the ability to disrupt a complex comprising a nuclear receptor and a SNMRT co-repressor having a structure and function characteristic of the silencing mediator for retinoic acid and thyroid receptors, those compounds which provide:

a higher reporter signal from the reporter responsive to the second member upon exposure of said compound to said second member, relative to reporter signal in the absence of compound, and substantially the same reporter signal from the reporter responsive to the first member upon exposure of said compound to said first member, relative to reporter signal in the absence of said compound, or identifying as capable of disrupting a complex comprising a nuclear receptor and a SMRT co-repressor having a structure and function characteristic of the silencing mediator for retinoic acid and thyroid receptors, and activating said receptor those compounds which provide:

a reduction in reporter signal from the reporter responsive to the first member upon exposure of said compound to said first member, relative to reporter signal in the absence of said compound, and increased reporter signal from the reporter responsive to the second member upon exposure of said compound to said second member, relative to reporter signal in the absence of said compound.

In accordance with a still further aspect of the present invention, there is provided a method to identify compounds which relieve the repression of nuclear receptor activity caused by an invention SMRT co-repressor, said method comprising determining the effect of adding test compound to an expression system comprising:

a modified member of the nuclear receptor superfamily, wherein said modified member contains an activation domain which renders said receptor constitutively active, a fusion protein comprising the receptor interaction domain of SMRT operatively linked to the GAL4 DNA binding domain, and a GAL4 response element operatively linked to a reporter.

Prior to addition of an effective ligand for the member of the nuclear receptor superfamily employed herein, the association of the modified member and the fusion protein will be effective to bind the GAL4 response element and activate transcription of the reporter. The presence of an effective ligand is indicated by a reduction of reporter signal upon exposure to ligand, which disrupts the interaction of the modified member and fusion protein.

Activation domains contemplated for use in the practice of the present invention are well known in the art and can readily be identified by the artisan. Examples include the GAL4 activation domain, BP64, and the like.

To summarize, a novel family of nuclear receptor SMRT co-repressor which mediates the transcriptional silencing of RAR and TR has been identified. This discovery is of great interest because transcriptional silencing has been shown to play an important role in development, cell differentiation and the oncogenic activity of v-erbA (Baniahmad et al., *EMBO J.* 11:1015-1023 (1992)); Gandrillon et al., *Cell* 49:687-697 (1989)); Zenke et al., *Cell* 61:1035-1049 (1990); Barlow et al., *EMBO J.* 13:4241-4250 (1994); Levine and Manley, *Cell* 59:405-408 (1989); Baniahmad et al., *Proc. Natl. Acad. Sci. USA* 89:10633-10637 (1992b); and Saitou et al., *Nature* 374:159-162 (1995)). In fact, v-erbA mutants that harbor the Pro160→Arg change in the TR neither repress basal transcription nor are capable of oncogenic transformation (Damm and Evans, (1993), supra).

The function of SMRT as a silencing mediator (co-repressor) of RAR and TR is analogous to mSin3 in the Mad-Max-Sin3 ternary complex (Schxeiber-Agus et al., *Cell* 80:777-786 (1995); and Ayer et al., *Cell* 80:767-776 (1995)). Because GAL-SMRT functions as a potent repressor when bound to DNA, it is reasonable to speculate that the function of the unliganded receptors is to bring with them SMRT to the template via protein-protein interaction. Thus, the repressor function is intrinsic to SMRT as opposed to the TR or RAR itself (Baniahmad et al., *Proc. Natl. Acad. Sci. USA* 90:8832-8836 (1993); and Fondell et al., *Genes Dev* 7:1400-1410 (1993)). It is demonstrated herein that the ligand triggers a dissociation of SMRT from the receptor, which would lead to an initial step in the activation process. This would be followed (or be coincident) with an induced conformational change in the carboxy-terminal transactivation domain (known as AF-2), allowing association with co-activators on the transcription machinery (Douarin et al., *EMBO J.* 14:2020-2033 (1995); Halachmi et al., *Science* 264:1455-1458 (1994); Lee et al., *Nature* 374:91-94 (1995); and Cavailles et al., *Proc. Natl. Acad. Sci. USA* 91:10009-10013 (1994)). Thus, as has previously been suggested (Damm and Evans, (1993), supra), the ligand dependent activation of TR would represent two separable processes including relief of repression and net activation. The isolation of SMRT now provides a basis for dissecting the molecular basis of trans-repression.

The invention will now be described in greater detail by reference to the following non-limiting examples.

EXAMPLE 1

Isolation of SMRT

Using a GAL4 DBD-RXR fusion protein (see, for example, U.S. Ser. No. 08/177,740, incorporated by reference herein in its entirety) as a bait in a yeast two-hybrid screening system (Durfee et al., (1993), supra), several cDNA clones encoding receptor interacting proteins were isolated. One of these proteins, SMRT, interacts strongly with unliganded RAR and TR but only weakly with RXR or other receptors in yeast. This protein was selected for further characterization.

EXAMPLE 2

Far-Western Blotting Procedure

Total bacteria extracts expressing GST fusions of hRARα (aa 156-462) or hRXRα LBD (aa 228-462) and control extracts expressing GST alone or GST-PML (romyelocytic leukemia) fusion protein were subjected to SDS/PAGE and electroblotted onto nitrocellulose in transfer buffer (25 mM Tris, pH 8.3/192 mM glycine/0.01% SDS). After denaturation/renaturation from 6 M to 0.187 M guanidine hydrochloride in HB buffer (25 mM HEPES, pH 7.7/25 mM NaCY5 mM $MgCl_2$/1 mM DTT) filters were saturated at 4° C. in blocking buffer (5% milk, then 1% milk in B buffer plus 0.05% NP40). In vitro translated $^{35}$S-labeled proteins were diluted into H buffer (20 mM Hepes, pH 7.7/75 mM KCl/0.1 mM EDTA/2.5 mM $MgCl_2$/0.05% NP40/1% milk/1 mM DTT) and the filters were hybridized overnight at 4° C. with (1 μM) or without ligand. After three washes with H buffer, filters were dried and exposed for autoradiography or quantitated by phosphoimager.

GST-SMRT is a GST fusion of the C-SMRT encoded by the yeast two hybrid clone. GST-SMRT has been purified, but contains several degradation products.

For yeast two-hybrid screening, a construct expressing the GAIA DBD-hRXRα LBD (aa 198462) fusion protein was used to screen a human lymphocyte cDNA library as described (Durfee et al., (1993), supra). The fi SMRT cDNA (SEQ ID NO:1) was isolated from a human HeLa cDNA library (Clontech) using the two-hybrid insert as a probe.

Using the above-described far-western blotting procedure, $^{35}$S-labeled SMRT preferentially complexes with bacterial extracts expressing the RAR, marginally associates with RXR and shows no association with control extracts. In contrast, $^{35}$S—PPAR selectively associates with its heterodimeric partner, RXR, but not with RAR. In a similar assay, $^{35}$S-labeled RAR or TR interacts strongly with SMRT and their heterodimeric partner, RXR, but not with degraded GST products, while $^{35}$S-RXR interacts only weakly with SMRT. Binding of ligand to RAR or TR reduces their interactions with SMRT but not with RXR, while binding of ligand to RXR has only slight effect. FIG. 1 shows the quantitation of a dose-dependent dissociation of SMRT from RAR or TR by all-trans retinoic acid (atRA) or thyroid hormone (triiodothyronine or T3), demonstrating that the amount of ligand required for 50% dissociation in both cases are close to the kds for both ligands (Munoz et al. *EMBO J.* 7:155-159 (1988); Sap et al., *Nature* 340:242-244 (1989); and Yang et al., *Proc. Natl. Acad. Sci. USA* 88:3559-3563 (1991)).

The first SMRT sequence cloned encodes a polypeptide of 1495 amino acids rich in proline and serine residues (see FIG. 2 and SEQ ID NO:1). Genbank database comparison reveals similarity of the C-terminal domain of SMRT to a partial cDNA encoding another receptor interacting protein, RIP13 (Seol et al., (1995), supra), whose role in receptor sing is unknown. Within this region, there can be identified several potential heptad repeats which might mediate protein-protein interaction with the "α-helical sandwich" structure (Bourguet et al., *Nature* 375:377-382 (1995)) of the ligand binding domain (LBD) of receptors.

EXAMPLE 3

Characterization of SMRT

Unlike other nuclear receptors, unliganded RAR and TR possess a strong silencing domain which represses basal level promoter activity of their target genes (Damm et al., *Nature* 339:593-597 (1989); Brent et al., *New Biol.* 1:329-336 (1989); Baniahmad et al., *Cell* 61:505-514 (1990); and Baniahmad et al., *EMBO J.* 11:1015-1023 (1992)). The preferential interaction of SMRT with RAR and TR in the absence of hormone suggests that SMRT may play a role in mediating the transcriptional silencing effect of the receptor.

To further investigate the involvement of SMRT in silencing, the interaction of SMRT with mutant receptors which display distinct silencing and/or transactivation activities was tested as follows. $^{35}$S-methionine labeled receptors were used as probes to hybridize immobilized GST-SMRT in the presence (10 μM) or absence of all-trans retinoic acid (atRA). The total bacteria extract expressing GST-RXR was included as a control.

When quantitated by phosphoimager, RAR403 shows a 4-fold better interaction with SMRT than wild type RAR. Both full length RAR or a deletion mutant expressing only the ligand binding domain (LBD, referred to as ΔΔR) associate with SMRT; this association is blocked by ligand.

These results confirm that the LBD alone is sufficient in the interaction. The carboxy-terminal deletion mutant RAR403 is a potent dominant negative repressor of basal level promoter activity of RAR target genes (Damm et al., *Proc. Natl. Acad. Sci. USA* 90:2989-2993 (1993); Tsai and Collins, *Proc. Natl. Acad. Sci. USA* 90:7153-7157 (1993); and Tsai et al., *Genes Dev* 6:2258-2269 (1992)). As might be predicted from the above studies, RAR403 and its amino terminal deletion derivative, R403, interact strongly with SMRT in either the presence or absence of ligand, consistent with SMRT mediating the repressor activity of this mutant.

EXAMPLE 4

Interaction of SMRT with TR Mutants

The interaction of SMRT with two different classes of TR mutants was analyzed next. The first mutant employed is the naturally occurring oncogene, v-erbA, which has strong silencing ability but no transactivation activity (Sap et al., (1989), supra; Sap et al., *Nature* 324:635-640 (1986); Weinberger et al., *Nature* 318:670-672 (1985); and Weinberger et al., *Nature* 324:641-646 (1986)). The second mutant employed is a single amino acid change (Pro 160->Arg) of the rTRα (TR160) which has previously been shown to lose its capacity in basal level repression but retains hormone dependent transactivation (Thompson et al., *Science* 237: 1610-1614 (1987); and Damm and Evans, Proc. Natl. Acad. Sci. USA 90:10668-10672 (1993)). If SMRT is involved in silencing, it would be expected that SMRT should interact with the v-erbA, but show little or no association with the silencing-defective TR160 mutant.

Interaction of the oncogenic v-erbA and rTRα R160 mutant (TR160) with GST-SMRT was determined in a far-western assay as described above (see Example 2). When quantitated by phosphoimager, the v-erbA shows an 18-fold better interaction with SMRT than hTRβ, and the TR160 mutant shows a 10-fold lower signal than the rTRα.

As one might expect, v-erbA interacts strongly with SMRT both in presence or absence of ligand. In contrast, full length TR160 mutant or LBD of TR160 (ΔΔTR160) does not interact significantly with SMRT when compared to the wild type receptor.

These data demonstrate that SMRT plays an important role in mediating transcriptional silencing effects of both RAR and TR. These data also suggest that the release of SMRT from receptors could be a prerequisite step in ligand-dependent transactivation by nuclear receptors.

EXAMPLE 5

Formation of Ternary Complexes Containing SMRT

RAR and TR form heterodimers with RXR, resulting in a complex with high DNA binding ability (Bugge et al., *EMBO J.* 11: 1409-1418 (1992); Yu et al., *Cell* 67:1251-1266 (1991); and Kliewer et al., *Nature* 355:446-449 (1992)). Since SMRT interacts with RAR and TR, tests were conducted to determine whether SMRT can also interact with the receptor-DNA complex. Thus, the interaction of SMRT with RXR-RAR heterodimer on a DR5 element (i.e., an AGGTCA direct repeat spaced by five nucleotides) was determined in a gel retardation assay, which is carried out as follows: In vitro translated receptor or unprogrammed reticulocyte lysate (URL) was incubated with 1 μg of poly dIdC on ice for 15 minutes in a total volume of 20 μl containing 75 mM KCl, 7.5% glycerol, 20 mM Hepes (pH 7.5), 2 mM DTT and 0.1% NP-40, with or without ligand (in the range of about 10-100 nM employed). A $^{32}$P labeled, double stranded oligonucleotide probe was added into the binding reaction (10,000 cpm per reaction), and the reaction was further incubated for 20 minutes at room temperature. The protein-DNA complex was separated on a 5% native polyacrylamide gel at 150 volts.

SMRT is seen to form a ternary complex with the RXR-RAR heterodimer on a DNA response element in the gel retardation assay. Addition of ligand releases SMRT from this complex in a dose-dependent manner.

Similarly, SMRT is seen to form a ternary complex with the RXR-TR heterodimer on a TR response element; addition of T3 disrupts the formation of this complex.

These data demonstrate that SMRT can be recruited to DNA response elements via protein-protein interaction with RAR or TR in the absence of hormone. Binding of hormone disrupts receptor-SMRT interaction and releases SMRT from the receptor-DNA complex.

EXAMPLE 6

Transient Transfection Assay

CV-1 cells were plated in 24 well plates at a density of 50,000 cells per well. Expression plasmids were transfected into cells by lipofection using DOTAP. In each transfection, 5 ng of GAL-RAR and 15 ng of v-erbA or SMRT were used together with 150 ng of reporter construct containing 4 copies of GAL4 binding sites in front of a minimal thymidine kinase promoter and a CMX-β-gal construct as an internal control. The relative luciferase activity was calculated by normalizing to the β-gal activity.

EXAMPLE 7

Reversal of Transcriptional Silencing

Figure 3A:
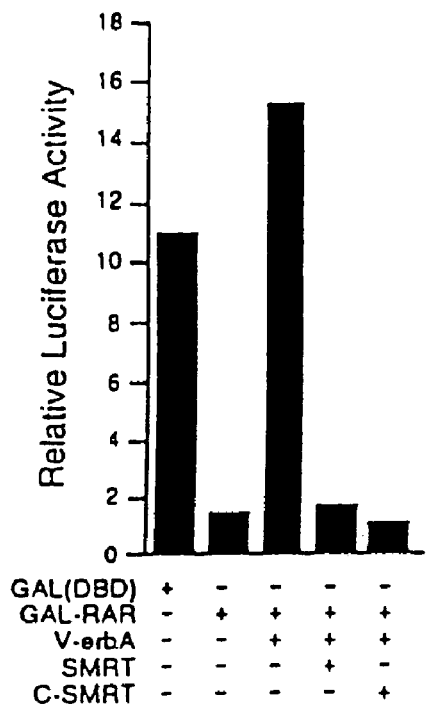
FIGS. 3A-3D illustrate mediation of the silencing effect of hRARα and hTRβ by SMRT in vivo.
Figure 3B:
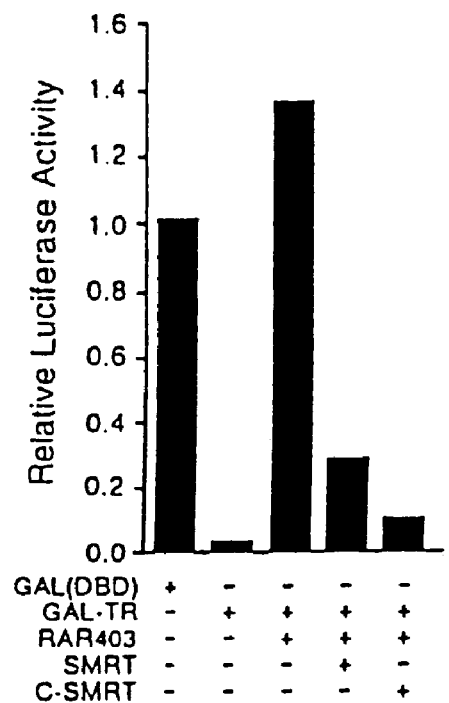

Recently, it has been shown that over expression of RAR or TR could reverse the transcriptional silencing effect of the GAL4 DBD fusion of TR (GAL-TR) or RAR (GAL-RAR) (Baniahmad et al., *Mol Cell Biol* 15:76-86 (1995); and Casanova et al., *Mol Cell Biol* 14:5756-5765 (1994)), presumably by competition for a limiting amount of a SMRT co-repressor. A similar effect is observed herein when over expression of v-erbA or RAR403 mutants are shown to reverse the silencing effect of GAL-RAR and GAL-TR on the basal activity of a luciferase reporter (see FIGS. 3A and 3B).

Figure 3C:
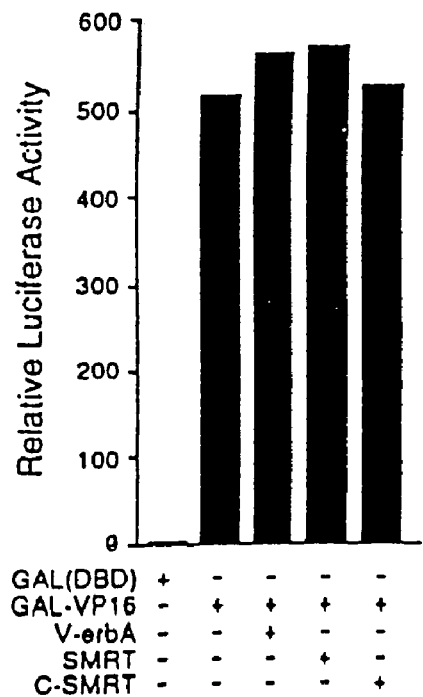

In principle, over expression of SMRT should restore repressor activity when co-expressed with v-erbA or RAR403 competitors. Indeed, results presented in FIG. 3C show that both the whole first SMRT clone (SEQ ID NO: 1) and its C-terminal domain of SMRT (C-SMRT) can titrate out v-erbA or RAR403 competitor activity and re-endow GALRAR and GAL-TR with silencing activity. In contrast neither v-erbA nor SMRT show any effect on the transactivation activity of GAL-VP16 fusion. Thus, SMRT is able to block the titration effect of v-erbA and RAR403 and functionally replaces the putative SMRT co-repressor in this system.

EXAMPLE 8

Direct Recruitment of SMRT to a Heterologous Promoter

Figure 3D:
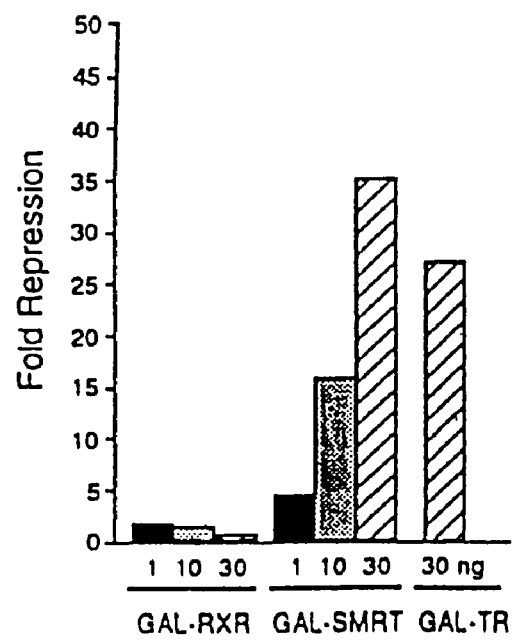

If SMRT is the mediator of transcription silencing of TR and RAR by interaction with template-bound unliganded receptors, then direct recruitment of SMRT to a heterologous promoter should result in repression of basal level activity. This was tested by fusing the whole first SMRT clone (SEQ ID NO:1) to the GAL4 DBD (GASMRT). The effect of the resulting fusion protein on the activity of the thymidine kinase promoter containing four GAL4 binding sites was analyzed. FIG. 3D shows that GAL-SMRT, like GAL-TR, can silence basal promoter activity in a dose-dependent manner. In contrast, GAL-RXR shows no repression.

These data suggest that SMRT, when recruited to a promoter by direct DNA binding or via association with an unliganded receptor, functions as a potent transcriptional repressor.

EXAMPLE 9

Cloning of Human and Mouse SMRT Co-Repressors

This example describes the cloning of a full length human silencing mediator of retinoic acid and thyroid hormone receptor (SMRT co-repressor) and of two mouse SMRT isoforms, m-SMRTα and m-SMRTβ.

An examination of the previously described human SMRT co-repressor revealed that the first eight amino acids and upstream sequences were derived from a portion of ribonucleoprotein K sequence. Accordingly, a mouse spleen cDNA lambda ZAP II library (Stratagene; La Jolla Calif.) was screened at low stringency with a probe corresponding to the approximately 1,000 5' base pairs (bp) of the previously identified human SMRT (s-SMRT; SEQ ID NO: 1). A 3.5 kilobase (kb) cDNA fragment was obtained that contained a unique sequence in addition to known s-SMRT sequence. The 5' end of this cDNA, and subsequently obtained clones, was used in successive rounds of screening of the mouse spleen cDNA library and a mouse brain cDNA library (Stratagene) and the full-length SMRTα isoform cDNA (SEQ ID NO: 6) and SMRTβ isoform cDNA (SEQ ID NO: 8) were obtained. The mouse SMRT (m-SMRT) 5' sequence then was used at low stringency to screen a human pituitary cDNA library (Stratagene) to obtain the full-length human SMRT (h-SMRT) cDNA (SEQ ID NO:4). All cDNA clones were sequenced on both strands using standard methods, and have been deposited with GenBank as Accession No. AF113003 (h-SMRT; SEQ ID NOS: 4 and 5); Accession No, AF113001 (m-SMRTα; SEQ ID NOS: 6 and 7); and Accession No. AF113002 (m-SMRTβ; SEQ ID NOS: 8 and 9).

By sequentially shifting between the mouse spleen and mouse brain cDNA libraries, several clones containing a potential starting methionine and 5' untranslated region sequences were obtained. The complete polypeptide sequences of m-SMRT (SEQ ID NO: 7) and h-SMRT (SEQ ID NO: 5) are provided. In addition, a splice variant isolated from the mouse brain cDNA library (SEQ ID NO:8) encoded an m-SMRT co-repressor (SEQ ID NO:9) containing a deletion of amino acids 36 to 254 of SEQ ID NO: 7. The two m-SMRT co-repressors are designated SMRTα (SEQ ID NO: 7) and SMRTβ (SEQ ID NO: 9). Based on sequence similarity to N-CoR (see below), this deletion in m-SMRTβ removes the majority of the sequence in h-SMRT and m-SMRTα that is homologous to N-CoR repression domain 1 (RD1), including a portion of the Sin3A binding region.

The cloned h-SMRT (SEQ ID NO: 4) encodes a polypeptide that contains an additional 1130 amino acids at the amino terminus as compared to the previously described human SMRT co-repressor. The full length h-SMRT shares 84% identity with m-SMRTα. A comparison of h-SMRT (SEQ ID NO: 5) and N-CoR (SEQ ID NO: 11) revealed that the N-terminal extension of h-SMRT (amino acids 1 to 1030) and N-CoR (amino acids 1 to 1031) share approximately 41% identity, which is somewhat higher that the 36% identity shared between the full length proteins. However, regions within the N-CoR and SMRT N-termini share striking homology (FIGS. 4A and 4B).

Amino acids 1 to 160 of N-CoR are moderately conserved in h-SMRT (and m-SMRTα), sharing about 36% identity. This region of N-CoR has been reported to interact with Siah2 (Zhang et al., (1998), supra) and, similarly, can be involved in an interaction of Siah2 with h-SMRT or m-SMRTα. In particular, highly conserved sequences in this region can be the specific Siah2 interaction sites (see FIG. 4A).

A 52 amino acid segment from N-CoR (amino acids 255 to 312) mediates an interaction with Sin3A (Heinzel et al., Nature 387:43-48 (1997)), and was presumed to represent the core of the larger RD1 region (Horlein et al., (1995), supra). This small interaction domain is highly conserved (about 83% identity) in h-SMRT, and the overall identity shared between SMRT and N-CoR RD1 is about 57%.

Amino acids 312 to 668 of N-CoR also are well conserved (66% identity) in h-SMRT (and m-SMRTα), and two internal blocks of sequences in this region share even greater similarity (see FIG. 1B; shaded regions). These blocks are homologous to each other and to part of the SANT domain, which was identified in the yeast chromatin remodeling factor, SWI3, the yeast adapter protein, ADA2, the basal transcription factor TFIIIB, and other proteins (Aasland et al., Trends Biochem. Sci. 21:87-88 (1996)), suggesting that these domains share a common and important function. The amino acids of N-CoR RD2 (see Horlein et al., (1995) supra) are the least conserved in h-SMRT, sharing about 30% identity.

These results demonstrate that isoforms of SMRT co-repressors are expressed in cells, as exemplified by m-SMRTα and m-SMRTβ. In addition, the results demonstrate that the previously undescribed amino terminus of SMRT co-repressors shares regions of substantial homology with N-CoR, and regions of homology are identified that indicate these sequences can mediate previously uncharacterized functions.

EXAMPLE 10

Expression And Chromosomal Localization of Smrt Co-Repressors

This example describes the tissue distribution of SMRT RNA and the chromosomal localization of human SMRT.

Total RNA was prepared from adult CB6F1 mouse tissues using TRIZOL reagent (GIBCO/BRL), and poly(A) RNA was purified from total RNA using an OLIGOTEX mRNA Kit (Qiagen, Valencia, Calif.). RNA was separated on 1.25% agarose/6% formaldehyde gels and transferred to a NYT-RAN membrane (Scheicher & Schuell). A 720 bp m-SMRT/PstI fragment was used as a probe. Following hybridization with the SMRT probe, the filters were stripped and hybridized with a murine glyceraldehyde-3-phosphate dehydrogenase cDNA probe to allow normalization for RNA loading.

Chromosomal localization of SMRT was determined by fluorescence in situ hybridization using the 5.3 kb h-SMRT cDNA clone. The probe was labeled by nick-translation with biotin-11-dUTP, then hybridized to normal male human metaphase chromosomes. Chromosomes were counterstained with 4',6-diamidino-2-phenylindole (DAPI). Chromosome identification was carried out by computer inversion of the gray scale DAPI image on a PSI Imaging System (Perceptive Scientific Instruments; League City Tex.). Chromosome 12 confirmation was carried out using a chromosome 12-specific alpha satellite probe (Vysis; Downers Grove Ill.).

Previous studies using the short human SMRT co-repressor suggested that SMRT was expressed ubiquitously in various tissues. To confirm this result, expression of the full length m-SMRT was determined by northern blot analysis by using a probe consisting of nucleotides 2760 to 3620 of m-SMRT (SEQ ID NO: 6). The expression pattern was ubiquitous, as previously described, although higher levels were detected in lung, spleen, and brain. Similarly, h-SMRT was expressed ubiquitously as determined using a multiple tissue blot (CLONTECH; Palo Alto Calif.). It is noteworthy that two isoforms of SMRT were present in the majority of the mouse tissues and likely correspond to the m-SMRTα and m-SMRTβ isoforms.

The chromosomal location of the h-SMRT and N-CoR genes was mapped. The h-SMRT clone hybridized to the q arm of one of the C group chromosomes. Computer-mediated banding of the DAPI stained chromosomes identified the labeled chromosome as chromosome 12, band q24. The chromosome 12 localization was confirmed by cohybridization of SMRT and a chromosome 12 alpha satellite probe, D12Z3 (Vysis), which labels the pericentromeric region of chromosome 12. The location for the human N-CoR gene was determined through a mapped human bacterial artificial chromosome clone, hCIT529110, which is 158 kb of genomic N-CoR and resides on chromosome 11p11.2. The SMRT and N-CoR chromosomal locations can be accessed through GENEMAP98 from the Human Genome Project at http://www.ncbi.nln.nih.gov/genemap.

These results demonstrate that the full length SMRT co-repressors and the SMRT co-repressors are expressed in various tissues. The results also demonstrate that the human SMRT gene is located on chromosome 12.

EXAMPLE 11

Functional Characterization of SMRT Amino Terminus Domains

This example demonstrates that various domains of the SMRT amino terminus can repress nuclear receptor transcriptional activity.

Experiments were performed using the plasmids pCMX-GAL4 DBD and pMH100-TK-luc (Nagy et al., (1997), supra). Standard PCR amplifications were used to generate GAL4 fusion constructs. All constructs were verified by double-stranded sequencing to confirm identity and reading frame.

Monkey CV-1 cells were grown in DMEM supplemented with 10% resin-charcoal stripped fetal bovine serum (FBS), 50 units/ml of penicillin G, and 50 μg/ml of streptomycin sulfate at 37° C. in 7% $CO_2$. V-1 cells (60-70% confluence, 48-well plate) were cotransfected with 16 ng of pCMX-GAL4, 100 ng of pMH100-TK-luc, and 100 ng of pCMX-β galactosidase in 200 μl of DMEM containing 10% superstripped fetal calf serum (FCS) by the N-(1-(2,3-dioleoyloxy)propyl)-N,N,N-trimethylammonium methylsulfate (DOTAP)-mediated procedure (Nagy et al., (1997), supra). The amount of DNA in each transfection was kept constant by addition of pCMX. After 24 hr, the medium was replaced; cells were harvested and assayed for luciferase activity 36 to 48 hr after transfection. Luciferase activity was normalized by the level of β-galactosidase activity. Each transfection was performed in triplicate and repeated at least three times.

Figure 5A:
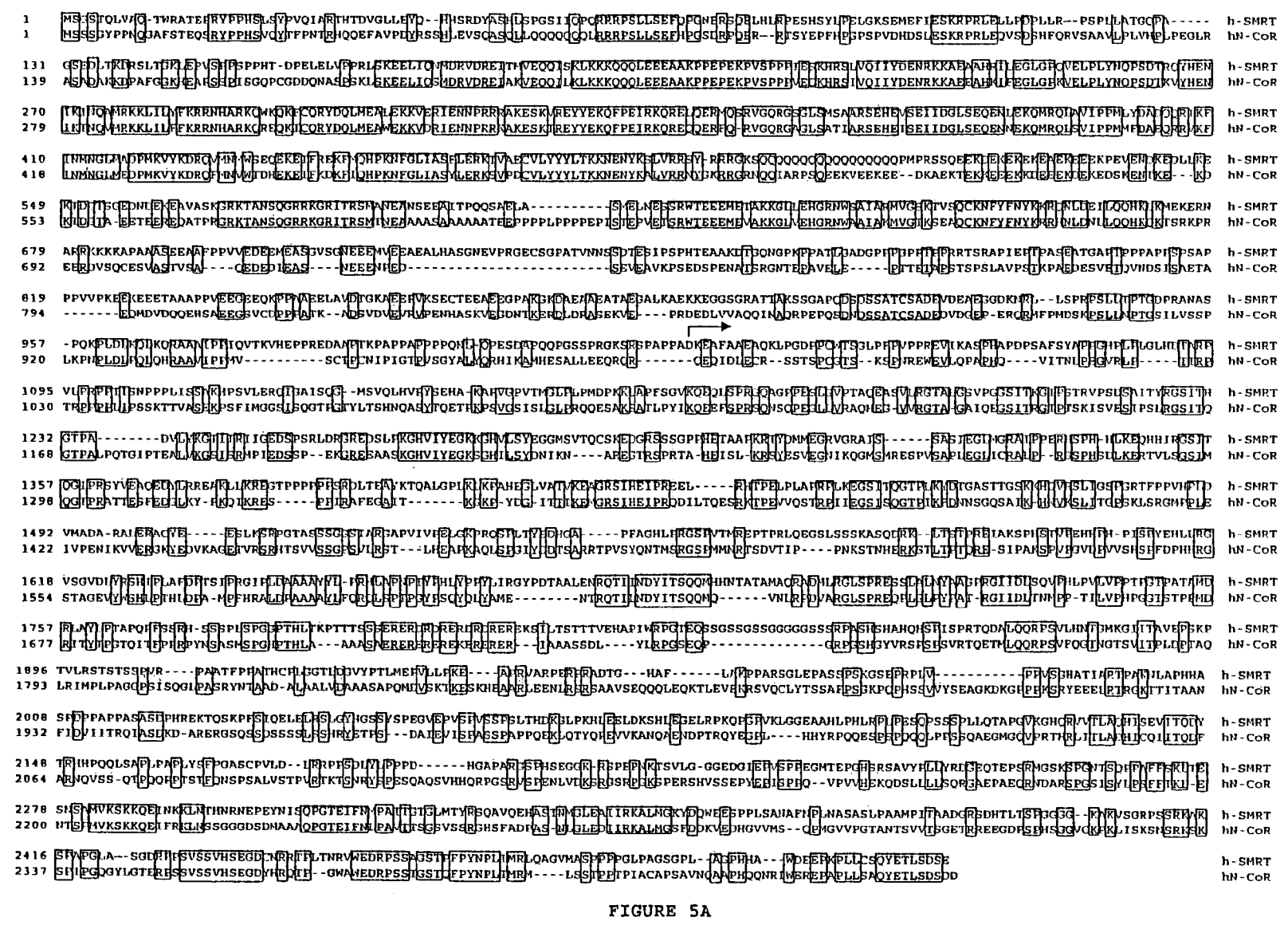
Figure 5B:
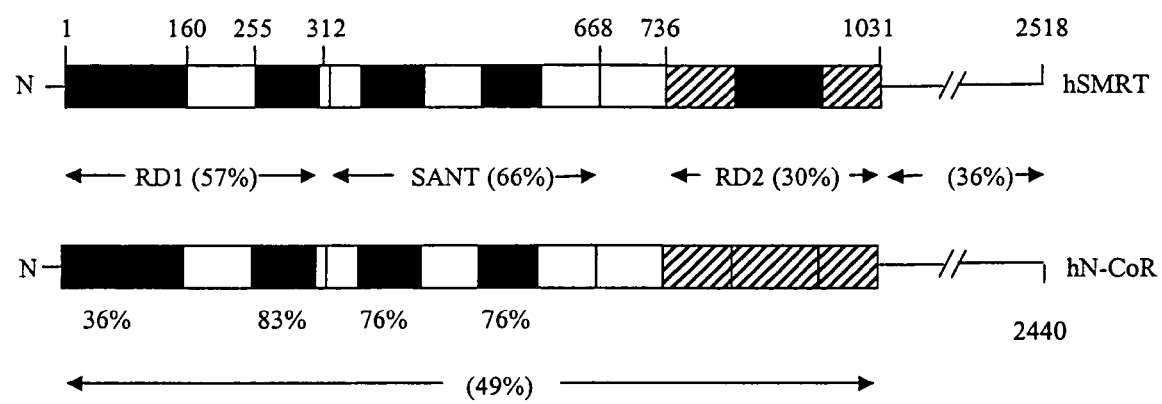

Based on the high degree of identity between regions of the SMRT amino terminus and the corresponding N-CoR region, the ability of regions in the SMRT amino terminus to act in transcriptional repression was examined. A nested series of nucleotide sequences encoding portions of the SMRT amino terminus fused to the GAL4 DNA binding domain (GAL-DBD) was prepared in mammalian expression vectors (FIG. 5A). The constructs were cotransfected with a GAL4-TK-luciferase reporter plasmid to determine the regulatory properties of the GAL4-SMRT fusions. Repression was determined relative to the basal activity of the reporter in the presence of the GAL-DBD alone.

The entire SMRT amino terminus region (GAL4-SMRT (1-1031)) demonstrated the greatest amount of repression (approximately 38-fold), and virtually extinguished reporter activity. In comparison, GAL4-SMRT (1-303), which is equivalent to N-CoR RD1, demonstrated 6-fold repression; and GAL4-SMRT (736-1031), which is equivalent to N-CoR RD2, demonstrated about 2.6-fold repression. Surprisingly, the highly conserved SANT domain conferred a significant amount of repression (about 3.3-fold).

A smaller region (amino acids 845 to 986) within the RD2 homology region shows a higher level of sequence conservation as compared to the entire RD2 region. Deletion constructs were generated to determine whether this minimal region was sufficient for the repression activity of RD2. Deletion of flanking amino acids 736 to 845 or of amino acids 987 to 1055 did not affect the level of repression, demonstrating that the repressor function of RD2 is contained within a 141 amino acid core sequence of RD2.

Based on sequence similarity to N-CoR, the deletion of amino acids 36 to 254 in the m-SMRTβ isoform removes the majority of RD1, including a portion of the Sin3A binding region. The effect of this deletion on SMRT function was examined by cotransfection experiments comparing repression by SMRTα to SMRTβ. These experiments revealed that SMRTβ has substantially less repressor activity than SMRTα. A construct containing the entire amino terminus of m-SMRTβ (amino acids 1 to 813) repressed activity about 2.6 fold, as compared to m-SMRTα amino acids 1 to 1031, which repressed activity about 38.1-fold. In addition, a GAL4 construct containing m-SMRT amino acids 1 to 83 repressed activity only about 1.4-fold. These results indicate that alternative splicing can add further diversity to expand the function of SMRT gene products.

EXAMPLE 12

Yeast Two-Hybrid Screen and Assays

To investigate whether repression by the ecdysone receptor (EcR) in CV-1 cells is mediated by its association with a vertebrate corepressor and whether such an interaction, if it does occur, is impaired by the A483T mutation, a mammalian two-hybrid assay with Gal4-c-SMRT was conducted.

A yeast two-hybrid screen (Fields and Song, Nature, 340:245-246, (1989)) was performed by transforming approximately $2\times10^6$ Y190 yeast cells with a pAS-EcR construct and a *Drosophila* (0-8 hr) embryonic c-DNA two-hybrid library (Yu et al., Nature, 385:552-555, (1997)). Transformants were selected onto DO-Leu-Trp-His plates containing 40 mM 3-aminotriazole (Sigma) for 3-4 days. Surviving yeast colonies were picked as primary positives and restreaked on selection plates to isolate single clones. Activation domain plasmids were rescued from the selected positive transformants for further analysis. Each clone was evaluated by testing its potential interaction with several other nuclear receptors using the yeast two-hybrid assays. E52 was isolated and further pursued based on this selection criterion. Quantitative liquid assay of β-galactosidase was performed on positive clones 16 hr after treating the yeast cells with no ligand, or with 3 μM ligand.

pAS-EcR is a fusion gene with the region corresponding to amino acids 223-878 of EcRB1 fused C-terminally to the Gal4-DBD of the pAS1-CYH2 construct (Durfee et al., (1993), supra); other Gal4-DBD-based nuclear receptor constructs used in this yeast two-hybrid assay include: USP (amino acids 50-508), hRAR (amino acids 186-462) and hTR (amino acids 121-410) (Schulman et al., (1995), supra), and SMRT (Chen and Evans, (1995), supra). β-galactosidase activities were quantified by liquid assay for yeast cells treated either without ligand or with 3 μM of corresponding hormone. All-trans retinoic acid (ATRA) is a ligand of RAR; 3,3',5-triiodothyroacetic acid (T3) is a ligand of TR.

Similar yeast two-hybrid assays were also used to examine the interaction between SMRTER and mSin3A and dSin3A.

EXAMPLE 12

Cloning SMRTER

Figures 8A, 8B:
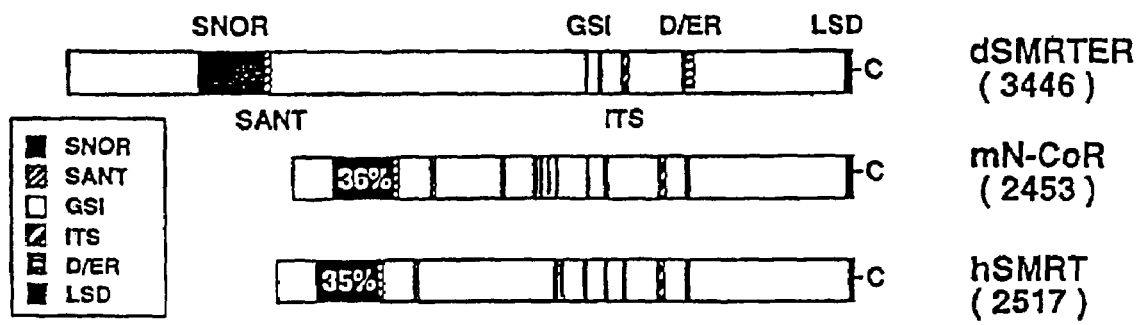
FIG. 8A shows the complete amino acid sequence of the SMRTER protein (SEQ ID NO: 12). The underlined regions represent the residues also conserved in SMRT and N-CoR. The gray box indicates the sequences of the E52 clone.
FIG. 8B is a schematic structural diagram of SMRTER, SMRT, and N-CoR showing the conserved SNOR, SANT, GST, ITS, D/ER repeat, and LSD motifs with their designated patterns positioned in their relative regions in each protein.
Figure 10:
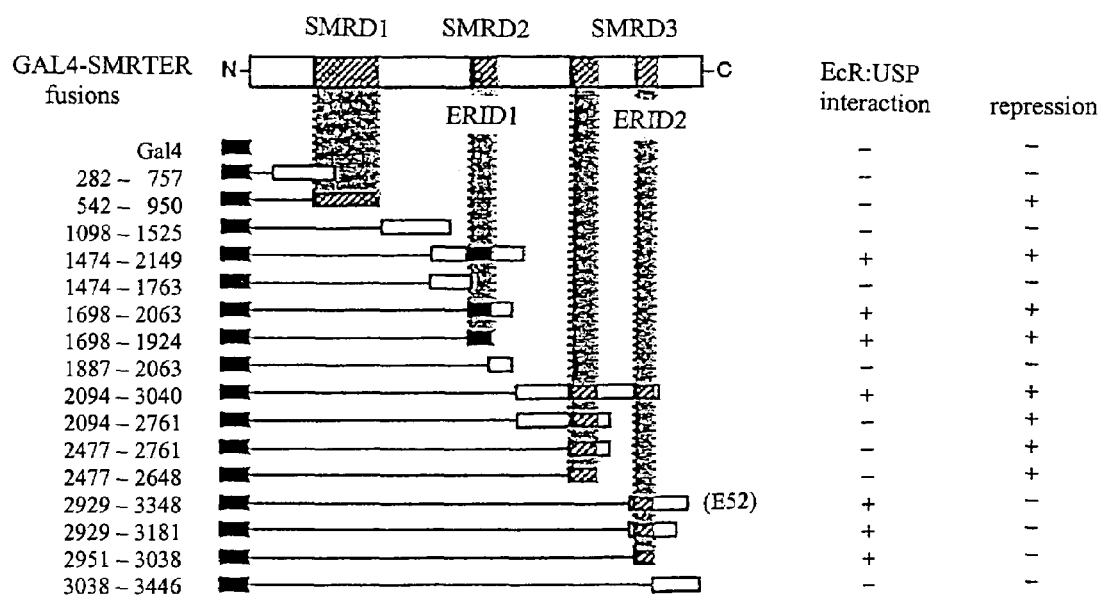
FIG. 10 is a schematic representation showing functional domains in SMRTER. Numbers on the left represent the regions in SMRTER used to generate the Gal4-DBD fusion genes. Black stippled bars indicate the locations of EcR-interacting domains; gray stippled bars indicate repression domains. Plus signs indicate that a positive interaction between SMRTER and the EcR complex and repression of basal activity by Gal4-SMRTER is significant. ERID=ecdysone receptor-interacting domain; SMRD=SMRTER repressor domain.
Figure 12A:
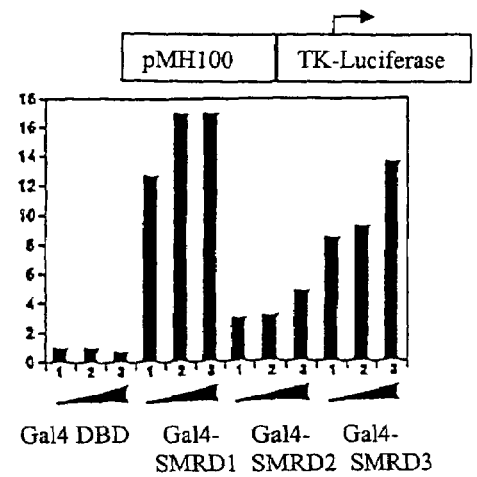
FIG. 12A shows the results of mapping three repression domains. To examine repressive activity, transcriptional activity of each Gal4-SMRTER fusion was compared to the basal activity of Gal4-DBD on reporter. Only repression with value approximately 5-fold or over is considered positive (+).
Figure 12B:
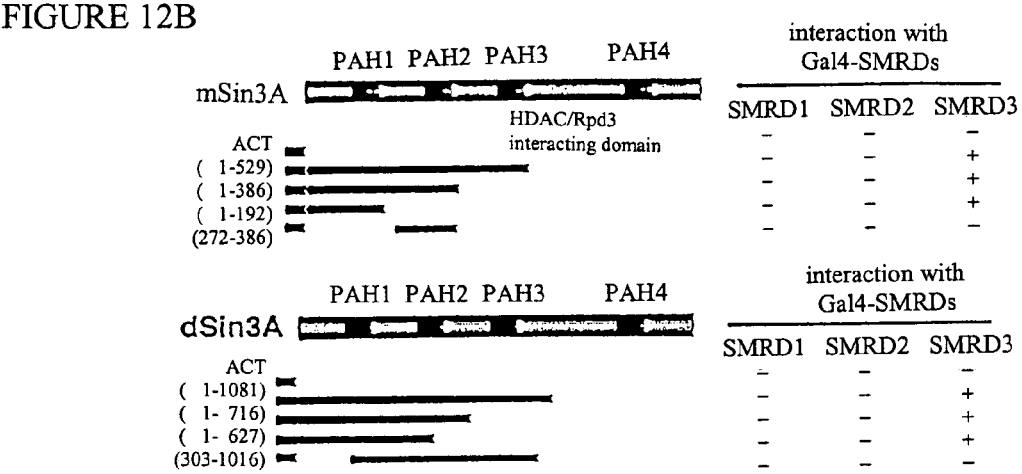
FIG. 12B is a schematic representation of mapping the SMRTER-interacting domain in mSin3A and dSin3A. Yeast two-hybrid assays were used to assess the interaction between each Gal4-DBD-based fusion gene of each SMRD and the ACT-based fusion genes of mSin3A and dSin3A. The numbers indicate the region in either mSin3A or in dSin3A used to generate the ACT fusion genes. Constructs of mSin3A were described previously in Nagy et al., *Cell* 89:373-380, (1997).
Figure 12C:
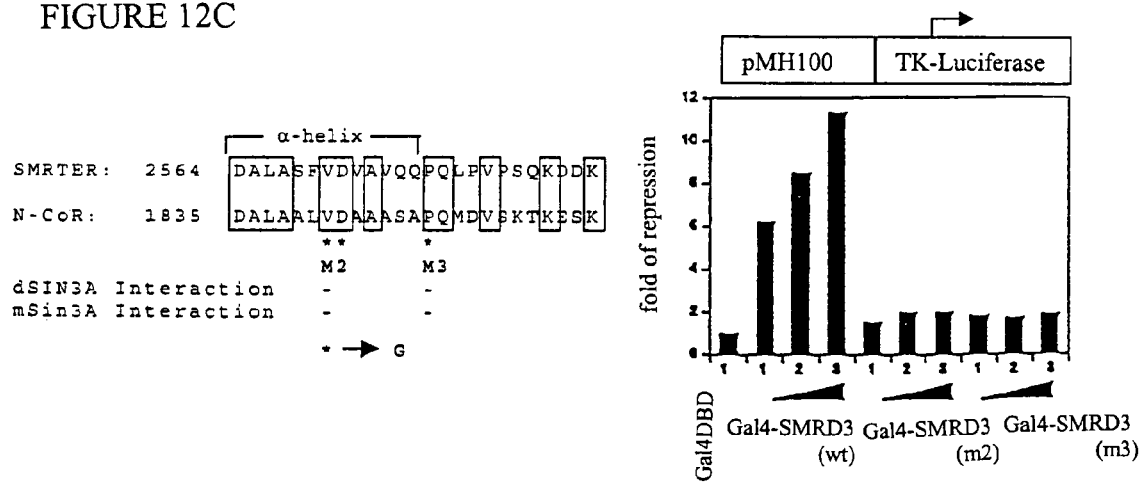
FIG. 12C shows an alignment of SMRD3 of SMRTER (amino acids 2564-2588 of SEQ ID NO: 12) and an mSin3-interacting domain of N-CoR (amino acids 1835-1859 of SEQ ID NO: 11). Conserved residues are boxed. An asterisk indicates the region where the mutation (Gly) was generated. Minus signs indicate that the interaction between SMRD3 and Sin3A was not detectable in the yeast two-hybrid assays. Repression was measured by comparing the transcriptional activity of Gal4-SMRD3 M2 or Gal4-SMRD3 M3 to that of wild-type Gal4-SMRD3 using transfection experiments as described above.

To isolate full-length SMRTER cDNA, a XhoI insert fragment isolated from the E52 clone was used to screen male and female Tudor c-DNA libraries (gift of Tulle Hazelrigg). This initial screen resulted in isolating three overlapping c-DNA clones covering the region of amino acid 2094 to the C terminus of SMRTER Additional regions were obtained from three consecutive library screens using two cosmid clones isolated from the Tamkun genomic library (gift of John Tamkun). Sequences of these overlapping c-DNA and genomic clones were assembled to obtain a conceptual open reading frame of SMRTER 3446 amino acids in length (SEQ ID NO:12; FIG. 8A). The translational initiation codon was designated based on the sequences that match the consensus Kozak codons and is preceded by three in-frame consecutive stop codons in the upstream region. Both strands of the sequences of the c-DNA clones were determined using an ABI prism Big Dye® terminator cycle sequencing ready reaction kit (PE Biosystems) and ABI 377 instrument.

EXAMPLE 14

Plasmids

CMV promoter-driven expression plasmids of EcR, USP, RXR, c-SMRT, β-galactosidase, and pMH100-TK-luc reporter, and yeast plasmids of RAR, TR, and SMRT have been described previously (Yao et al., (1992), supra, Yao et al., (1993), supra; Chen and Evans, (1995), supra; Schulman et al., (1995), supra; Chen et al., *Proc. Natl. Acad. Sci. USA* 93:7567-7571, (1996); Nagy et al., (1997), supra). hsp27EcR-TK-Luc, a reporter with six copies of the hsp27EcRE, is a gift of Barry Forman. CMV vector-driven EcR A483T and Gal4-SMRD3 mutations were generated using the Transformer® site-directed mutagenesis kit (Clontech) with proper selection primers and the mutagenic primers that correspond to the missense mutation (A483T) of EcR and to the designated mutations, M2 and M3, in the SMRD3 domain, respectively. Other plasmids were constructed with standard techniques, including various enzyme digestions or PCR amplification.

EXAMPLE 15

Cell Culture and Transfection

CV-1 cells were grown in Dulbecco's modified Eagles medium at 37° C. in 5% $CO_2$. The media were supplemented with 10% AG1-X8 resin charcoal double-stripped calf bovine serum, 50 U/ml penicillin G, and 50 µg/ml streptomycin sulfate. Approximately 20 hr after CV-1 cells ($10^5$ cells) were plated in 48-well cell culture clusters (Costar), cells were transiently transfected with plasmids using DOTAP according to the instructions of the manufacturer (Boehringer Mannheim). The amount of CMV promoter-driven expression vectors, β-galactosidase gene expression vector, CMX-lacZ, and reporter, pMH100-TK-luc or hsp27EcRE-TK-Luc, were in the range of 100-200 ng, 500 ng, and 400 ng, respectively, for six wells of each 48-well clusters in each transfection experiments. At least 4 hr after transfection, each medium was replaced with medium either without ligand, or with 1 µM of MurA. Cells were harvested and assayed approximately 48 hr after transfection. All experiments were performed in triplicate and repeated with similar results.

Figure 6A:
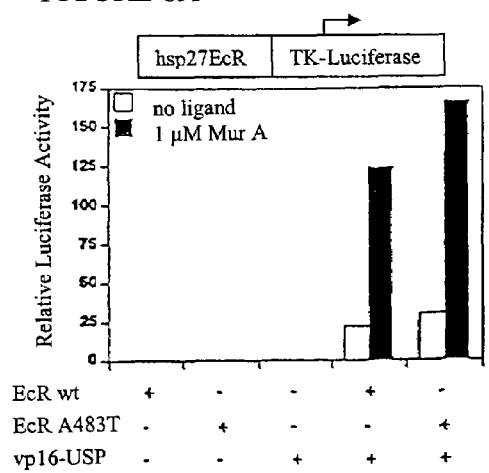
FIG. 6A is a graph showing the results of transactivation experiments using transcripts encoding a detectable reporter and either wild type EcR (Ecr wt), a repression-Defective EcR allele Ecraa$^{483T}$ (EcRA483T) or vp16 activation domain fused to Ultraspiracle (vp16-USP).

CV-1 cells were transfected with wild-type EcR or EcR A483T, along with vp16-USP and a reporter, hsp27EcRE-TK-Luc, which contains six copies of the hsp27EcRE fused to the thymidine kinase (TK) promoter-luciferase reporter. VP16-USP fusion contains the region of USP (amino acids 50-508) fused C-terminally to the VP16 domain. Muristerone A (MurA) is a potent ecdysone agonist (Christopherson et al., *Proc. Natl. Acad. Sci. USA*, 89:6314-6318, (1992)). In all experiments, cells were also cotransfected with CMV-lacZ, which is used to normalize the luciferase activity. As shown in FIG. 6A, the ability to dimerize with USP is reflected in reporter activity without treatment with hormone (open bar), and the ability to respond to hormone is reflected in reporter activity when cells were treated with 1 µM Muristerone A (closed bar).

CMV promoter-driven expression vector including wild-type EcR or EcR A483T was cotransfected with VP16-USP and Gal4-c-SMRT (amino acids 981 to C terminus) (Chen and Evans, (1995), supra) into CV-1 cells to examine its effect on the interaction with vertebrate corepressor. All cells were also cotransfected with a TK-luciferase reporter construct, pMH 100-TK-Luc, containing four copies of the yeast Gal4-responsive element. EcR A483T corresponds to a single amino acid change (alanine→threonine) at the 483 site of EcR (Bender et al., (1997), supra). The results of this experiment (FIG. 6B) show that EcR A483T disrupts the interaction with SMRT.

EXAMPLE 16

In Vitro Interacting Assays

Glutathione S-transferase fusion proteins, including GST-X, GST-ERID1 (amino acids 1698-2063 of SEQ ID NO:1), and GST-ERID2 (amino acids 2951-3038 of SEQ ID NO:1), were expressed in *E. coli* DH5 cells, and extracts were affinity purified by binding to glutathione Sepharose 4B beads. Bound proteins used as affinity matrices in pull-down experiments were first equilibrated with the binding buffer (20 mM HEPES [pH 7.9], 150 mM NaCl, 1 mM EDTA, 4 mM $MgCl_2$, 1 mM DTT, 0.06% NP40, 10% Glycerol, 0.25 mM PMSF, 1 mg BSA). For pull-down assays using GST-ERID1 (amino acids 1698-2063 of SEQ ID NO:1) and GST-ERID2 (amino acids 2951-3038 of SEQ ID NO:1), additional hsp27EcRE (0.05 µg/ml) was added to the binding buffer. In this experiment, 301 of 50% GST-protein beads slurry, containing approximately 1 µg of proteins, were incubated with 10 µl of 35S-methionine-labeled proteins in 300 µl of the binding buffer (with or without 3 µM of MurA as indicated) for 30 min at room temperature. After the incubation, beads were washed three times with the binding buffer (with or without ligand) and resuspended in SDS-PAGE sample buffer before loading. After electrophoresis, bound radio-labeled proteins were visualized by autoradiography. 35S-methionine-labeled EcR, USP were generated in a coupled transcription-translation system, TNT (Promega), using CMX-EcR (T7) and CMX-uspK (T7) constructs as templates, respectively.

EXAMPLE 17

Immunohistochemistry and Immunofluorescence

Antibodies against SMRTER were raised in rabbits immunized with bacterially expressed glutathione S-transferase fusion proteins corresponding to the region (amino acids 2477-2648 of SEQ ID NO:1) of SMRTER. Specific antibodies were purified by affinity chromatography through antigen-linked columns and used at 1:200 dilution for tissue staining. Tissues for whole-mount staining were dissected at the wandering third instar stage of the Canton-S strain larvae and fixed (4% formaldehyde in 1? PBS, 50 mM EGTA) for at least 30 min. Preincubation, secondary antibodies, washes, and peroxidase reactions are described in the protocol of the Elite ABC (Rabbit IgG) kit (Vector). For the pilot experiments, partially purified IgG from preimmunization serum was used. For polytene chromosome staining, salivary glands were dissected according to the method described in Zink et al., *EMBO J.*, 10:153-162, (1991).

Chromosome spreads were costained with affinity-purified anti-SMRTER (1:100) polyclonal antibody and with anti-USP monoclonal antibody (ABIII/AD5; gift of F. Kafatos, 1:100 dilution). SMRTER was detected with Texas red-conjugated donkey anti-rabbit secondary antibody (1:100 dilution), and USP was detected with FITC-conjugated donkey anti-mouse secondary antibody (1:100 dilution) (Jackson ImmunoResearch Labs).

EXAMPLE 18

ER Interacts Genetically with DSinA

In keeping with the evidence that dSin3A is a component in EcR regulatory pathway, an experiment was conducted to examine whether dSin3A interacts genetically with EcR using several previously characterized *Drosophila* EcR and dSin3A mutants (Bender et al., (1997), supra; Neufeld et al., (1998), supra). In the experiment, in which female dSin3AK07401 were crossed with male EcRE261st using techniques known in the art (see Table 1 below), only approximately 14% of the scored EcRE261st/dSin3AK07401 progenies survived, a percent that is significantly lower than the expected 33.3%. This suggests that a large portion of the EcRE261st/dSin3AK07401 flies either die prior to eclosion or fail to eclose. Additionally, surviving EcRE261st/dSin3AK07401 escapers showed delayed development and wing defects, in which wings are held horizontally at 45°-90° angle from the body axis. These results suggest that dSin3A shares an overlapping regulatory pathway with EcR.

In a reverse genetic cross, in which female EcRE261st were crossed with male dSin3AK07401, none of the EcRE261st/dSin3AK07401 flies survived to adulthood. These results suggest that EcRE261st/dSin3AK07401 results in a genetically sensitized background. When the maternally deposited EcR in embryos descended from female EcRE261st/SM6b was cut in half, the lethality for EcRE261st/dSin3AK07401 was further increased. These results reveal that, in addition to its previously known zygotic function, EcR also contributes maternally to *Drosophila* development.

TABLE 1

EcR Interacts Genetically with DSin3A

| Cross | | $EcR^{E261st}/DSin3A^{KO7401}$ Surviving Rate (%) |
|---|---|---|
| $DSin3A^{KO7401}/CyO \times$ $EcR^{261st}/SM6b$ | ♀ ♂ | 14 (n = 141) |
| $EcR^{261st}/SM6b \times$ $DSin3A^{KO7401}/CyO$ | ♀ ♂ | 0 (n = 144) |

A similar wing held-out phenotype is also observed in $EcR^{E261st}/$ $DSin3A^{xe374}$, $Df(2R)nap11/DSin3A^{KO7401}$, and $Df(2R)nap11/Dsin2A^{xe374}$. $EcR^{E261st}$ and $Df(2R)nap11$ are both described in FIG. 6. $Dsin2A^{KO7401}$ is an allele with a P element insertion within the 5' intron of Sin3A. $DSin3A^{xe374}$ is an X ray-generated allele (Neufeld et al., (1998)). n = the number of surviving flies scored. Note that CyO/SM6b is lethal.

EcRA483T flies showed developmental abnormalities in wings and tergites. A similar phenotype, although with a lower penetration rate, has been also observed in EcRA483T/Df(2R)20B and in EcRA483T/Df(2R)nap11. Df(2)20B and Df(2)nap11 are both deficiencies in which EcR is deleted (Bender et al., (1997), supra). Sequence alignment of EcR with the vertebrate TR, RAR, and v-erbA, an oncogenic TR variant, revealed that alanine 483 is located within a highly conserved 23-amino acid (aa) loop region connecting helices 3 and 4, termed the LBD signature motif (Wurtz et al., *Nat. Struct. Biol.*, 3:206, (1996)) (see FIG. 6C). Based on structural studies of vertebrate nuclear receptors (for review, see Moras and Gronemeyer, (1998), supra), this alanine residue appears to be on the exposed surface, consistent with it being a potential corepressor binding site for nuclear receptors.

These in vivo studies indicate that EcRA483T is a semi-lethal allele (Bender et al., (1997), supra). When EcRA483T is in trans with EcRE261st, an allele that removes both the DBD and LBD domains of EcR, animals are primarily lethal (>95%). The few surviving EcRA483T/EcRE261st flies, however, display significant delays in development, blistered wings, and defective tergites, indicating that EcR is involved in the development of these tissues. The ability of EcR to bind a vertebrate corepressor and the loss of this property in EcR A483T suggests that the defects observed in EcRA483T flies may result from the disruption of its interaction with an as yet unidentified *Drosophila* corepressor.

EXAMPLE 19

Isolation of an EcR-Interacting Factor

Figure 6B:
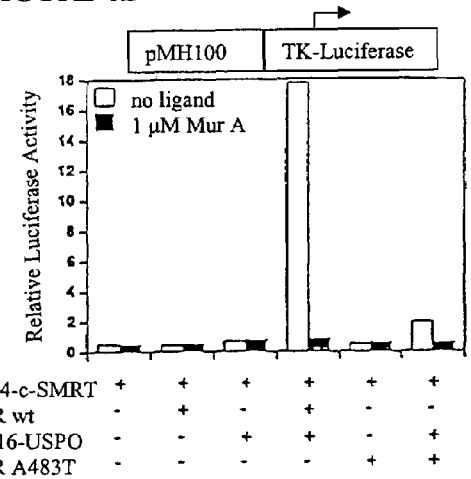
FIG. 6B is a graph showing the results of transactivation experiments using CMV promoter-driven expression vectors. Wild-type EcR or EcR A483T was cotransfected with vp16-USP and Gal4-c-SMRT (aa 981 to C terminus) (Chen and Evans, *Nature* 377:454-457, (1995)) into CV-1 cells to examine its effect on the interaction with vertebrate corepressor. All cells were also cotransfected with a TK-luciferase reporter construct, pMH100-TK-Luc, containing four copies of the yeast Gal4-responsive element.
Figure 7:
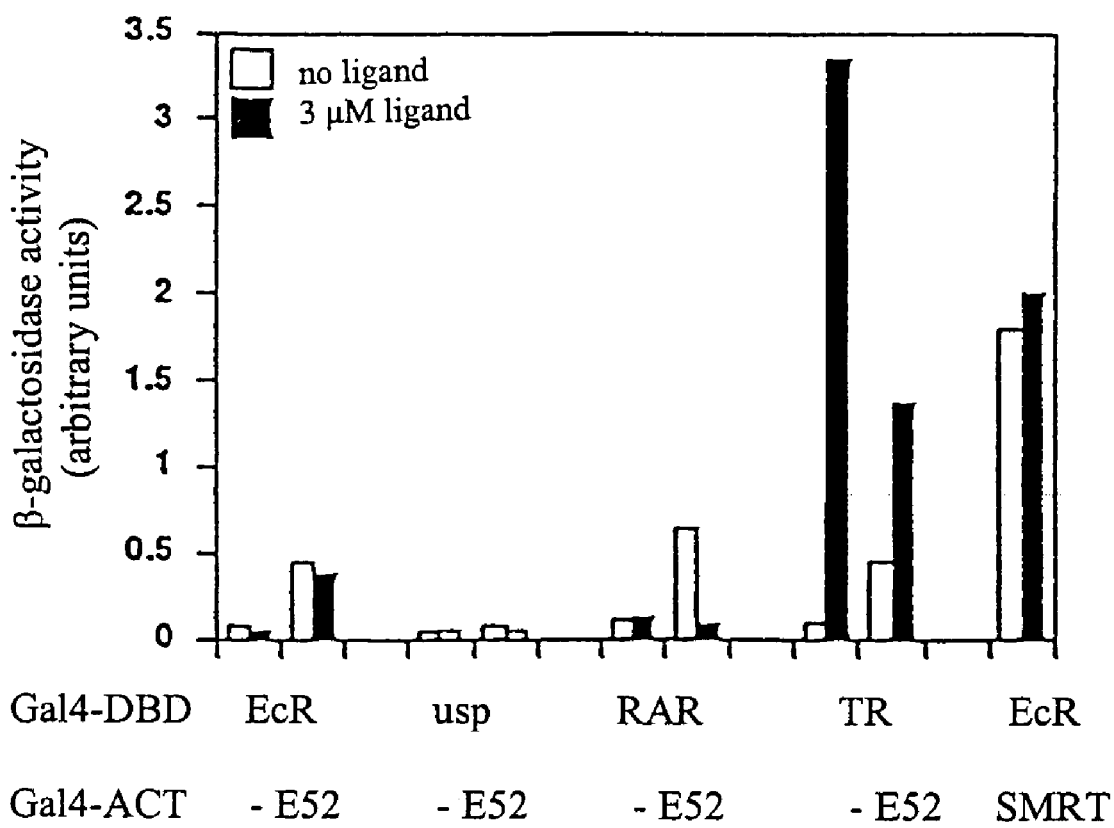
FIG. 7 is a graph showing β-galactosidase activity in a yeast two-hybrid screen with pAS-EcR as bait. pAS-EcR is a fusion gene with the region corresponding to aa 223-878 of EcRB1 fused C-terminally to the Gal4-DBD of the pAS1-CYH2 construct (Durfee et al., *Genes Dev* 7:555-569 (1993)); other Gal4-DBD-based nuclear receptor constructs used in this yeast two-hybrid assay include: USP (aa 50-508), HRAR (aa 186-462) and hTR (aa 121-410) (Schulman et al., *Proc. Natl. Acad. Sci. USA*, 92:8288-8292, (1995)), and SMRT (Chen and Evans, (1995), supra). β-galactosidase activities were quantified by liquid assay for yeast cells treated either without ligand or with 3 µM of corresponding hormone. All-trans retinoic acid (ATRA) is a ligand of RAR; 3,3',5-triiodothyroacetic acid (T3) is a ligand of TR. RAR, retinoic acid receptor; TR, thyroid hormone receptor.

The CMV promoter-driven expression vector including wild-type EcR or EcR A483T, was cotransfected with vp16-USP and Gal4-c-SMRT (amino acids 981 to C terminus) (Chen and Evans, (1995), supra) into CV-1 cells to examine its effect on the interaction of the invertebrate SMRTER with vertebrate corepressor. All cells were also cotransfected with a TK-luciferase reporter construct, pMH100-TK-Luc, containing four copies of the yeast Gal4-responsive element. EcR A483T corresponds to a single amino acid change (alanine→threonine) at the 483 site of EcR (Bender et al., (1997), supra). Although EcR readily interacted with SMRT in both mammalian and yeast cells (FIG. 6B; FIG. 7), repeated low-stringency hybridization screens failed to identify a *Drosophila* homolog of SMRT. No SMRT/N-CoR homolog was found in *C. elegans*.

EXAMPLE 20

Isolation and Characterization of an EcR-Interacting Clone—Yeast Two-Hybrid Screen To pursue the isolation of an EcR corepressor, a yeast two hybrid interaction screen was performed of a *Drosophila* embryonic cDNA library using pAS-EcR as bait. E52 was isolated as one of the complementary positive clones from a yeast two-hybrid screen with pAS-EcR as bait, as described in Example 12.

EXAMPLE 21

Characterization of a Repression-Defective EcR Allele, EcRA483T (A) CV-1 cells were transfected with wild-type EcR or EcR A483T, along with vp16-USP and a reporter, hsp27EcRE-TK-Luc, which contains six copies of the hsp27EcRE fused to the thymidine kinase (TK) promoter-luciferase reporter. In all experiments, cells were also cotransfected with CMV-lacZ, which is used to normalize the luciferase activity. The ability to dimerize with USP was reflected in reporter activity without treatment with hormone (open bar), and the ability to respond to hormone was reflected in reporter activity when cells were treated with 1 µM Muristerone A (closed bar). vp16-USP fusion contains the region of USP (amino acids 50-508) fused C-terminally to the vp16 domain. Muristerone A (MurA) is a potent ecdysone agonist (Christopherson et al., (1992), supra). In these tests EcR A483T was selectively defective in repression.

(B) CMV promoter-driven expression vector including wild-type EcR or EcR A483T was cotransfected with vp16-USP and Gal4-c-SMRT (amino acids 981 to C terminus) (Chen and Evans, (1995), supra) into CV-1 cells to examine its effect on the interaction with vertebrate corepressor. All cells were also cotransfected with a TK-luciferase reporter construct, pMH100-TK-Luc, containing four copies of the yeast Gal4-responsive element. EcR A483T corresponds to a single amino acid change (alanine threonine) at the 483 site of EcR (Bender et al., (1997), supra). The results of this test show that EcR A483T disrupts the interaction with SMRT.

Figure 6C:
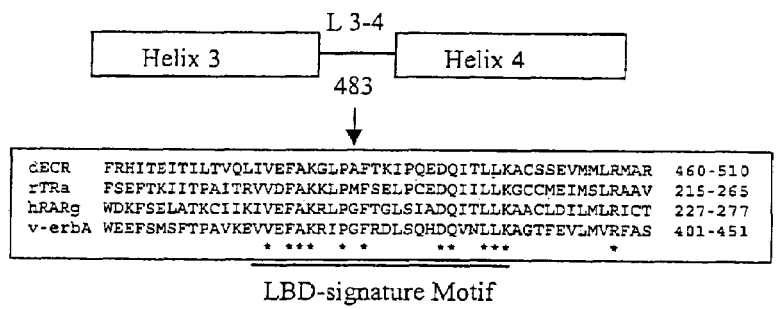
FIG. 6C shows alignment of EcR (amino acids 460-510; SEQ ID NO: 14), rTR (amino acids 215-265; SEQ ID NO:15), hRAR (amino acids 227-277; SEQ ID NO:16), and rRev-erbA (amino acids 401-451; SEQ ID NO:17) receptor sequences and the secondary structure in the LBD signature motif region. Conserved residues are marked with asterisks. The mutation 483 (AT) is marked at the top of the corresponding residue.

(C) Sequence alignment of EcR with the vertebrate TR, RAR, and v-erbA, an oncogenic TR variant, reveals that the alanine 483 of the EcRA4831T mutant is located within a highly conserved 23-amino acid (aa) loop region connecting helices 3 and 4, termed the LBD signature motif (Wurtz et al., (1996), supra) (FIG. 6C). Based on structural studies of vertebrate nuclear receptors (for review, see Moras and Gronemeyer, (1998), supra), this alanine residue appears to be on the exposed surface, consistent with it being a potential corepressor binding site for nuclear receptors.

In vivo studies indicated that EcRA483T is a semilethal allele (Bender et al., (1997), supra). When EcRA483T is in trans with EcRE261st, an allele that removes both the DBD and LBD domains of EcR, animals are primarily lethal (>95%). The few surviving EcRA483T/EcRE261st flies, however, display significant delays in development, blistered wings, and defective tergites, indicating that EcR is involved in the development of these tissues. The ability of EcR to bind a vertebrate corepressor and the loss of this property in EcR A483T suggested to us that the defects observed in EcRA483T flies may result from the disruption of its interaction with an as yet unidentified *Drosophila* corepressor.

EXAMPLE 22

Isolation of an EcR-Interacting Factor

Although EcR readily interacts with SMRT in both mammalian and yeast cells (FIG. 6B; FIG. 7), repeated low-stringency hybridization screens failed to identify a *Drosophila* homolog of SMRT. Given that no SMRT/N-CoR homolog is found in *C. elegans*, it was believed that either a SMRT/N-CoR-like corepressor is not conserved in invertebrates or, alternatively, invertebrate corepressors may diverge significantly from their vertebrate counterparts. To pursue the isolation of an EcR corepressor, a yeast interaction screen of a *Drosophila* embryonic cDNA library using EcR as bait was conducted as described in Example 19. This screen resulted in the isolation of a clone, E52, whose protein product interacts with EcR as well as with the vertebrate RAR and TR, but notably not with USP (FIG. 7). Unlike the interaction between E52 and RAR, which can be dissociated by all-trans retinoic acid, the interaction between E52 and EcR, or the interaction between SMRT and EcR, is not dissociated by Muristerone A (MurA). This result suggests that other factors essential for the dissociation of E52 from EcR, such as USP, are missing in yeast (see below).

EXAMPLE 23

Isolation and Characterization of an EcR-Interacting Clone

E52 was isolated as one of the complementary positive clones from a yeast two-hybrid screen. Isolation of overlapping cDNA and genomic clones led to the identification of a full-length sequence encoding a large protein of 3446 amino acids (FIG. 8A). This protein contains several unusually long stretches of Gln, Ala, Gly, and Ser repeats. Comparative analysis reveals it to be a novel protein with limited regions of clear homology with the vertebrate nuclear receptor corepressors SMRT and N-CoR (Chen and Evans, (1995), supra; Hörlein et al., (1995), supra; Ordentlich et al., (1999), supra; Park et al., (1999), supra). This protein SMRTER, SMRT-related ecdysone receptor-interacting factor, was shown by Northern blot analysis to encode large transcripts (>12 kb) expressed broadly throughout the embryonic stage and three larvae stages, as well as in adult *Drosophila* flies.

EXAMPLE 24

Molecular and Biochemical Analysis for ERID1 and ERID2

Interaction with the EcR complex was evaluated based on transient transfection with the Gal4-SMRTER fusion genes. USP, EcR-vp16 (VP16 transactivating domain was fused C-terminally to the end of the EcRB1 isoform), and the reporter, pMH100-TK-Luc.

In vitro pull down assays (Example 12) were conducted to determine whether EcR interacts with ERID1 and ERID2. In vitro translated 35S-methionine-labeled EcRB1 alone, or a mixture of 35S-methionine-labeled EcRB1 and unlabeled USP, or 35S-methionine-labeled USP alone, were incubated with GST, GST-ERID1 (amino acids 1698-2063 of SEQ ID NO:12), or GST-ERID2 (amino acids 2929-3038 of SEQ ID NO: 12), GST-ERID1 and GST-ERID2, but not GST alone, pull down labeled ECR, whereas little interaction is found between USP and any of the three GST proteins. In addition, the pull-own complex was disrupted by the addition of 3 µM MurA when USP is present. These in vitro results establish that SMRTER and EcR may interact directly.

Further in vitro tests were conducted to determine if ERID1, ERID2, and c-SMRT compete with each other to bind EcR. Gal4-ERID1 (amino acids 1698-2063 of SEQ ID NO:12) or Gal4ERID2 (amino acids 2929-3181 of SEQ ID NO: 12), along with EcR-vp16 and USP, were transfected in CV-1 cells as described above. In this competition experiment, additional ERID1, ERID2, and c-SMRT (Chen et al., (1996), supra) were cotransfected into cells. ERID1 (amino acids 1698-2063 of SEQ ID NO:12) and ERID2 (amino acids 2929-3038 of SEQ ID NO:12) were tagged with the nuclear targeting signal (MAPKKKRKV) (SEQ ID NO:13) to ensure that these proteins were localized in nuclei. As shown in FIG. 11C, interaction between each Gal4-ERID fusion and EcR-vp16:USP was significantly decreased by both ERIDs and by c-SMRT. Interestingly, a more prominent effect was observed in experiments when Gal4ERID1

(amino acids 1698-2063 of SEQ ID NO: 12) was challenged by ERID2, and, conversely, a more efficient competition was achieved by ERIL to Gal4-ERID2 (amino acids 2094-3181 of SEQ ID NO: 12). Together, these results suggest that ERID1, ERID2, and c-SMRT may bind similar or overlapping surface(s) in EcR.

EXAMPLE 25

SMRTER Colocalizes with the EcR on Polytene Chromosomes

SMRTER antibodies were prepared as described in Example 12 to examine its cytological and chromosomal localization patterns of SMRTER. Consistent with its action as a corepressor of EcR, SMRTER was localized to nuclei of salivary glands and of fat bodies, as well as to nuclei of eye, wing, and leg imaginal discs isolated from the third instar larvae.

Next association of SMRTER with the EcR:USP complex on chromosomes was examined. The USP staining pattern was used as an index for EcRs presence on chromosomes. Since USP and EcR colocalized with each other on polytene chromosomes (Yao et al., (1993), supra), chromosomal spreads prepared from the salivary glands of wandering third instar larvae (prior to pupariation) were subjected to simultaneous immunological staining with antibodies against SMRTER and USP. SMRTER was detected with antibody conjugated with Texas red, USP with FITC.

To visualize the band, interband, and puffing patterns of the polytene chromosomes, the chromosomes were counterstained with DAPI to show the banding regions while leaving the interbands and puffs unstained or lightly stained. Indirect immunofluorescence staining revealed that SMRTER is a chromosome-bound protein and colocalizes with USP (FITC) at a majority of chromosomal sites; whereas in a pilot experiment, no such staining patterns were detected using the preimmunization serum. The strongest SMRTER staining was primarily associated with the boundary between band and interband regions as well as within the interband regions of chromosomes counterstained with DAPI. This result confirms that, as an EcR-associating factor, SMRTER is recruited by the EcR:USP heterodimers to their specific target chromosomal loci.

SMRTER staining can still be detected in puffed regions, such as the 2B puff. Since the polytene chromosomes consist of a parallel arrangement of several hundred to two thousand copies of the euchromatic portions of the chromosomes, an individual binding protein like SMRTER may be cycling on and off, resulting in a steady state of signals detected in the broader chromatin regions. Whether or not SMRTER levels actually change prior to or after the peak of ecdysone pulses remains to be established.

While the invention has been described in detail with reference to certain preferred embodiments thereof, it will be understood that modifications and variations are within the spirit and scope of that which is described and claimed.

That which is claimed is:

1. An isolated polynucleotide encoding a SMRT co-repressor (silencing mediator of retinoic acid receptor and thyroid hormone receptor), or an isolated polynucleotide complementary thereto, wherein said SMRT co-repressor is capable of mediating the transcriptional silencing of at least one member of the steroid/thyroid hormone superfamily of receptors, and wherein the amino acid sequence of said SMRT co-repressor comprises the amino acid sequence of SEQ ID NO: 5 or conservative variations thereof.

2. The polynucleotide of claim 1, wherein the SMRT co-repressor comprises a repression domain having
   a) less than 83% identity with a Sin3A interaction domain of N-CoR set forth as amino acids 255 to 312 of SEQ ID NO: 11;
   b) less than 57% identity with repression domain 1 of N-CoR set forth as amino acids 1 to 312 of SEQ ID NO: 11;
   c) less than 66% identity with a SANT domain of N-CoR set forth as amino acids 312 to 668 of SEQ ID NO: 11; or
   d) less than 30% identity with repression domain 2 of N-CoR set forth as amino acids 736 to 1031 of SEQ ID NO: 11.

3. The polynucleotide of claim 1, which is operably linked to a second nucleotide sequence.

4. The polynucleotide of claim 3, which encodes a fusion polypeptide comprising the SMRT co-repressor operably linked to a DNA binding domain of a transcription factor.

5. A vector comprising the polynucleotide of claim 1.

6. A host cell containing the polynucleotide of claim 1.

7. An isolated polynucleotide encoding a SMRT co-repressor (silencing mediator of retinoic acid receptor and thyroid hormone receptor), or an isolated polynucleotide complementary thereto, wherein said SMRT co-repressor is capable of mediating the transcriptional silencing of at least one member of the steroid/thyroid hormone superfamily of receptors, and wherein the amino acid sequence of said SMRT co-repressor comprises the amino acid sequence of SEQ ID NO: 5.

8. An isolated polynucleotide encoding a SMRT co-repressor (silencing mediator of retinoic acid receptor and thyroid hormone receptor), or an isolated polynucleotide entirely complementary thereto, wherein said SMRT co-repressor is capable of mediating the transcriptional silencing of at least one member of the steroid/thyroid hormone superfamily of receptors, and wherein said polynucleotide has the sequence set forth in SEQ ID NO: 4.

9. The polynucleotide of claim 8, comprising nucleotides 1 to 8561 of SEQ ID NO: 4.

* * * * *

SEQUENCE LISTING

<160> NUMBER OF SEQ ID NOS: 52

<210> SEQ ID NO 1
<211> LENGTH: 1495
<212> TYPE: PRT
<213> ORGANISM: Homo sapiens

<400> SEQUENCE: 1

```
Met Glu Ala Trp Asp Ala His Pro Asp Lys Glu Ala Phe Ala Ala Glu
 1               5                  10                  15

Ala Gln Lys Leu Pro Gly Asp Pro Pro Cys Trp Thr Ser Gly Leu Pro
             20                  25                  30

Phe Pro Val Pro Pro Arg Glu Val Ile Lys Ala Ser Pro His Ala Pro
         35                  40                  45

Asp Pro Ser Ala Phe Ser Tyr Ala Pro Pro Gly His Pro Leu Pro Leu
     50                  55                  60

Gly Leu His Asp Thr Ala Arg Pro Val Leu Pro Arg Pro Pro Thr Ile
 65                  70                  75                  80

Ser Asn Pro Pro Pro Leu Ile Ser Ser Ala Lys His Pro Ser Val Leu
                 85                  90                  95

Glu Arg Gln Ile Gly Ala Ile Ser Gln Gly Met Ser Val Gln Leu His
                100                 105                 110

Val Pro Tyr Ser Glu His Ala Lys Ala Pro Val Gly Pro Val Thr Met
            115                 120                 125

Gly Leu Pro Leu Pro Met Asp Pro Lys Lys Leu Ala Pro Phe Ser Gly
        130                 135                 140

Val Lys Gln Glu Gln Leu Ser Pro Arg Gly Gln Ala Gly Pro Pro Glu
145                 150                 155                 160
```

-continued

```
Ser Leu Gly Val Pro Thr Ala Gln Glu Ala Ser Val Leu Arg Gly Thr
            165                 170                 175
Ala Leu Gly Ser Val Pro Gly Gly Ser Ile Thr Lys Gly Ile Pro Ser
        180                 185                 190
Thr Arg Val Pro Ser Asp Ser Ala Ile Thr Tyr Arg Gly Ser Ile Thr
    195                 200                 205
His Gly Thr Pro Ala Asp Val Leu Tyr Lys Gly Thr Ile Thr Arg Ile
210                 215                 220
Ile Gly Glu Asp Ser Pro Ser Arg Leu Asp Arg Gly Arg Glu Asp Ser
225                 230                 235                 240
Leu Pro Lys Gly His Val Ile Tyr Glu Gly Lys Lys Gly His Val Leu
            245                 250                 255
Ser Tyr Glu Gly Gly Met Ser Val Thr Gln Cys Ser Lys Glu Asp Gly
        260                 265                 270
Arg Ser Ser Gly Pro Pro His Glu Thr Ala Ala Pro Lys Arg Thr
    275                 280                 285
Tyr Asp Met Met Glu Gly Arg Val Gly Arg Ala Ile Ser Ser Ala Ser
    290                 295                 300
Ile Glu Gly Leu Met Gly Arg Ala Ile Pro Pro Glu Arg His Ser Pro
305                 310                 315                 320
His His Leu Lys Glu Gln His His Ile Arg Gly Ser Ile Thr Gln Gly
            325                 330                 335
Ile Pro Arg Ser Tyr Val Glu Ala Gln Glu Asp Tyr Leu Arg Arg Glu
            340                 345                 350
Ala Lys Leu Leu Lys Arg Glu Gly Thr Pro Pro Pro Pro Pro Ser
        355                 360                 365
Arg Asp Leu Thr Glu Ala Tyr Lys Thr Gln Ala Leu Gly Pro Leu Lys
    370                 375                 380
Leu Lys Pro Ala His Glu Gly Leu Val Ala Thr Val Lys Glu Ala Gly
385                 390                 395                 400
Arg Ser Ile His Glu Ile Pro Arg Glu Glu Leu Arg His Thr Pro Glu
            405                 410                 415
Leu Pro Leu Ala Pro Arg Pro Leu Lys Glu Gly Ser Ile Thr Gln Gly
        420                 425                 430
Thr Pro Leu Lys Tyr Asp Thr Gly Ala Ser Thr Thr Gly Ser Lys Lys
    435                 440                 445
His Asp Val Arg Ser Leu Ile Gly Ser Pro Gly Arg Thr Phe Pro Pro
450                 455                 460
Val His Pro Leu Asp Val Met Ala Asp Ala Arg Ala Leu Glu Arg Ala
465                 470                 475                 480
Cys Tyr Glu Glu Ser Leu Lys Ser Arg Pro Gly Thr Ala Ser Ser Ser
            485                 490                 495
Gly Gly Ser Ile Ala Arg Gly Ala Pro Val Ile Val Pro Glu Leu Gly
        500                 505                 510
Lys Pro Arg Gln Ser Pro Leu Thr Tyr Glu Asp His Gly Ala Pro Phe
    515                 520                 525
Ala Gly His Leu Pro Arg Gly Ser Pro Val Thr Met Arg Glu Pro Thr
    530                 535                 540
Pro Arg Leu Gln Glu Gly Ser Leu Ser Ser Lys Ala Ser Gln Asp
545                 550                 555                 560
Arg Lys Leu Thr Ser Thr Pro Arg Glu Ile Ala Lys Ser Pro His Ser
            565                 570                 575
Thr Val Pro Glu His His Pro His Pro Ile Ser Pro Tyr Glu His Leu
```

-continued

```
            580                 585                 590
Leu Arg Gly Val Ser Gly Val Asp Leu Tyr Arg Ser His Ile Pro Leu
        595                 600                 605
Ala Phe Asp Pro Thr Ser Ile Pro Arg Gly Ile Pro Leu Asp Ala Ala
        610                 615                 620
Ala Ala Tyr Tyr Leu Pro Arg His Leu Ala Pro Asn Pro Thr Tyr Pro
625                 630                 635                 640
His Leu Tyr Pro Pro Tyr Leu Ile Arg Gly Tyr Pro Asp Thr Ala Ala
                645                 650                 655
Leu Glu Asn Arg Gln Thr Ile Ile Asn Asp Tyr Ile Thr Ser Gln Gln
        660                 665                 670
Met His His Asn Thr Ala Thr Ala Met Ala Gln Arg Ala Asp Met Leu
        675                 680                 685
Arg Gly Leu Ser Pro Arg Glu Ser Ser Leu Ala Leu Asn Tyr Ala Ala
        690                 695                 700
Gly Pro Arg Gly Ile Ile Asp Leu Ser Gln Val Pro His Leu Pro Val
705                 710                 715                 720
Leu Val Pro Pro Thr Pro Gly Thr Pro Ala Thr Ala Met Asp Arg Leu
                725                 730                 735
Ala Tyr Leu Pro Thr Ala Pro Gln Pro Phe Ser Ser Arg His Ser Ser
                740                 745                 750
Ser Pro Leu Ser Pro Gly Gly Pro Thr His Leu Thr Lys Pro Thr Thr
        755                 760                 765
Thr Ser Ser Ser Glu Arg Glu Arg Asp Arg Asp Arg Glu Arg Asp Arg
        770                 775                 780
Asp Arg Glu Arg Glu Lys Ser Ile Leu Thr Ser Thr Thr Thr Val Glu
785                 790                 795                 800
His Ala Pro Ile Trp Arg Pro Gly Thr Glu Gln Ser Ser Gly Ser Ser
                805                 810                 815
Gly Ser Ser Gly Gly Gly Gly Ser Ser Arg Pro Ala Ser His
                820                 825                 830
Ser His Ala His Gln His Ser Pro Ile Ser Pro Arg Thr Gln Asp Ala
        835                 840                 845
Leu Gln Gln Arg Pro Ser Val Leu His Asn Thr Gly Met Lys Gly Ile
        850                 855                 860
Ile Thr Ala Val Glu Pro Ser Lys Pro Thr Val Leu Arg Ser Thr Ser
865                 870                 875                 880
Thr Ser Ser Pro Val Arg Pro Ala Ala Thr Phe Pro Pro Ala Thr His
                885                 890                 895
Cys Pro Leu Gly Gly Thr Leu Asp Gly Val Tyr Pro Thr Leu Met Glu
                900                 905                 910
Pro Val Leu Leu Pro Lys Glu Ala Pro Arg Val Ala Arg Pro Glu Arg
        915                 920                 925
Pro Arg Ala Asp Thr Gly His Ala Phe Leu Ala Lys Pro Pro Ala Arg
        930                 935                 940
Ser Gly Leu Glu Pro Ala Ser Ser Pro Ser Lys Gly Ser Glu Pro Arg
945                 950                 955                 960
Pro Leu Val Pro Pro Val Ser Gly His Ala Thr Ile Ala Arg Thr Pro
                965                 970                 975
Ala Lys Asn Leu Ala Pro His His Ala Ser Asp Pro Pro Ala Pro
                980                 985                 990
Pro Ala Ser Ala Ser Asp Pro His Arg Glu Lys Thr Gln Ser Lys Pro
        995                 1000                1005
```

-continued

Phe Ser Ile Gln Glu Leu Glu Leu Arg Ser Leu Gly Tyr His Gly Ser
    1010                1015                1020

Ser Tyr Ser Pro Glu Gly Val Glu Pro Val Ser Pro Val Ser Ser Pro
1025                1030                1035                1040

Ser Leu Thr His Asp Lys Gly Leu Pro Lys His Leu Glu Glu Leu Asp
            1045                1050                1055

Lys Ser His Leu Glu Gly Glu Leu Arg Pro Lys Gln Pro Gly Pro Val
        1060                1065                1070

Lys Leu Gly Gly Glu Ala Ala His Leu Pro His Leu Arg Pro Leu Pro
    1075                1080                1085

Glu Ser Gln Pro Ser Ser Ser Pro Leu Leu Gln Thr Ala Pro Gly Val
    1090                1095                1100

Lys Gly His Gln Arg Val Val Thr Leu Ala Gln His Ile Ser Glu Val
1105                1110                1115                1120

Ile Thr Gln Asp Tyr Thr Arg His His Pro Gln Gln Leu Ser Ala Pro
            1125                1130                1135

Leu Pro Ala Pro Leu Tyr Ser Phe Pro Gly Ala Ser Cys Pro Val Leu
        1140                1145                1150

Asp Leu Arg Arg Pro Pro Ser Asp Leu Tyr Leu Pro Pro Pro Asp His
    1155                1160                1165

Gly Ala Pro Ala Arg Gly Ser Pro His Ser Glu Gly Gly Lys Arg Ser
    1170                1175                1180

Pro Glu Pro Asn Lys Thr Ser Val Leu Gly Gly Gly Glu Asp Gly Ile
1185                1190                1195                1200

Glu Pro Val Ser Pro Pro Glu Gly Met Thr Glu Pro Gly His Ser Arg
            1205                1210                1215

Ser Ala Val Tyr Pro Leu Leu Tyr Arg Asp Gly Glu Gln Thr Glu Pro
        1220                1225                1230

Ser Arg Met Gly Ser Lys Ser Pro Gly Asn Thr Ser Gln Pro Pro Ala
    1235                1240                1245

Phe Phe Ser Lys Leu Thr Glu Ser Asn Ser Ala Met Val Lys Ser Lys
    1250                1255                1260

Lys Gln Glu Ile Asn Lys Lys Leu Asn Thr His Asn Arg Asn Glu Pro
1265                1270                1275                1280

Glu Tyr Asn Ile Ser Gln Pro Gly Thr Glu Ile Phe Asn Met Pro Ala
            1285                1290                1295

Ile Thr Gly Thr Gly Leu Met Thr Tyr Arg Ser Gln Ala Val Gln Glu
        1300                1305                1310

His Ala Ser Thr Asn Met Gly Leu Glu Ala Ile Ile Arg Lys Ala Leu
    1315                1320                1325

Met Gly Lys Tyr Asp Gln Trp Glu Glu Ser Pro Pro Leu Ser Ala Asn
    1330                1335                1340

Ala Phe Asn Pro Leu Asn Ala Ser Ala Ser Leu Pro Ala Ala Met Pro
1345                1350                1355                1360

Ile Thr Ala Ala Asp Gly Arg Ser Asp His Thr Leu Thr Ser Pro Gly
            1365                1370                1375

Gly Gly Gly Lys Ala Lys Val Ser Gly Arg Pro Ser Ser Arg Lys Ala
        1380                1385                1390

Lys Ser Pro Ala Pro Gly Leu Ala Ser Gly Asp Arg Pro Pro Ser Val
    1395                1400                1405

Ser Ser Val His Ser Glu Gly Asp Cys Asn Arg Arg Thr Pro Leu Thr
    1410                1415                1420

-continued

```
Asn Arg Val Trp Glu Asp Arg Pro Ser Ser Ala Gly Ser Thr Pro Phe
1425                1430                1435                1440

Pro Tyr Asn Pro Leu Ile Met Arg Leu Gln Ala Gly Val Met Ala Ser
            1445                1450                1455

Pro Pro Pro Pro Gly Leu Pro Ala Gly Ser Gly Pro Leu Ala Gly Pro
        1460                1465                1470

His His Ala Trp Asp Glu Pro Lys Pro Leu Leu Cys Ser Gln Tyr
    1475                1480                1485

Glu Thr Leu Ser Asp Ser Glu
    1490                1495

<210> SEQ ID NO 2
<211> LENGTH: 46
<212> TYPE: PRT
<213> ORGANISM: Homo sapiens

<400> SEQUENCE: 2

His Ser Asp Val Ser Glu Ser Lys Arg Lys Arg Phe Glu Leu Asn Ser
  1               5                  10                  15

Gly Glu Ala Gly Gly Asn Ala Thr Ser Ala Met Thr Asn Ser Ser Thr
            20                  25                  30

Ser Gly Ser Met Asn Ile Ser Asn Ser His Gly Leu Lys Ala
        35                  40                  45

<210> SEQ ID NO 3
<211> LENGTH: 17
<212> TYPE: DNA
<213> ORGANISM: Saccharomyces sp.

<400> SEQUENCE: 3
cggaggactg tcctccg                                                      17

<210> SEQ ID NO 4
<211> LENGTH: 8561
<212> TYPE: DNA
<213> ORGANISM: Homo sapiens

<400> SEQUENCE: 4
catgtcgggc tccacacagc ttgtggcaca gacgtggagg gccactgagc cccgctaccc        60
gccccacagc ctttcctacc cagtgcagat cgcccggacg cacacggacg tcgggctcct       120
ggagtaccag caccactccc gcgactatgc ctcccacctg tcgccgggct ccatcatcca       180
gccccagcgg cggaggccct ccctgctgtc tgagttccag cccgggaatg aacgtcccca       240
ggagctccac ctgcggccag agtcccactc atacctgccc gagctgggga agtcagagat       300
ggagttcatt gaaagcaagc gccctcggct agagctgctg cctgaccccc tgctgcgacc       360 gtcaccctg ctggccacgg gccagcctgc gggatctgaa gacctcacca aggaccgtag       420
cctgacgggc aagctggaac cggtgtctcc ccccagcccc ccgcacactg accctgagct       480
ggagctggtg ccgccacggc tgtccaagga ggagctgatc cagaacatgg accgcgtgga       540
ccgagagatc accatggtag agcagcagat ctctaagctg aagaagaagc agcaacagct       600
ggaggaggag gctgccaagc cgcccgagcc tgagaagccc gtgtcaccgc gcccatcga       660 gtcgaagcac cgcagcctgg tgcagatcat ctacgacgag aaccggaaga aggctgaagc       720
tgcacatcgg attctggaag gcctggggcc ccaggtggag ctgccgctgt acaaccagcc       780
ctccgacacc cggcagtatc atgagaacat caaaataaac caggcgatgc ggaagaagct       840
aatcttgtac ttcaagagga ggaatcacgc tcggaaacaa tggaagcaga agttctgcca       900
```

```
gcgctatgac cagctcatgg aggccttgga aaaaaggtg gagcgcatcg aaaacaaccc    960
gcgccggcgg gccaaggaga gcaaggtgcg cgagtactac gaaaagcagt tccctgagat   1020
ccgcaagcag cgcgagctgc aggagcgcat gcagagcagg gtgggccagc ggggcagtgg   1080
gctgtccatg tcggccgccc gcagcgagca cgaggtgtca gagatcatcg atggcctctc   1140
agagcaggag aacctggaga agcagatgcg ccagctggcc gtgatcccgc ccatgctgta   1200
cgacgctgac cagcagcgca tcaagttcat caacatgaac gggcttatgg ccgacccat    1260
gaaggtgtac aaagaccgcc aggtcatgaa catgtggagt gagcaggaga aggagacctt   1320
ccgggagaag ttcatgcagc atcccaagaa ctttggcctg atcgcatcat tcctggagag   1380
gaagacagtg gctgagtgcg tcctctatta ctacctgact aagaagaatg agaactataa   1440
gagcctggtg agacggagct atcggcgccg cggcaagagc cagcagcaac aacagcagca   1500
gcagcagcag cagcagcagc agcagcagca gcccatgccc cgcagcagcc aggaggagaa   1560
agatgagaag gagaaggaaa aggaggcgga gaaggaggag gagaagccgg aggtggagaa   1620
cgacaaggaa gacctcctca aggagaagac agacgcacac tcaggggagg acaacgacga   1680
gaaggaggct gtggcctcca aggccgcaa aactgccaac agccagggaa gacgcaaagg   1740
ccgcatcacc cgctcaatgg ctaatgagcc aacagcgag gaggccatca ccccccagca   1800
gagcgccgag ctggcctcca tggagctgaa tgagagttct cgctggacag aagaagaaat   1860
ggaaacagcc aagaaggtc tcctggaaca cggccgcaac tggtcggcca tcgcccggat   1920
ggtgggctcc aagactgtgt cgcagtgtaa gaacttctac ttcaactaca agaagaggca   1980
gaacctcgat gagatcttgc agcagcacaa gctgaagatg gagaaggaga ggaacgcgcg   2040
gaggaagaag aagaaagcgc cggcggcggc cagcgaggag gctgcattcc cgcccgtggt   2100
ggaggatgag gagatggagg cgtcgggcgt gagcggaaat gaggaggaga tggtggagga   2160
ggctgaagcc ttcatgcct ctgggaatga ggtgccaga ggggaatgca gtggcccagc   2220
cactgtcaac aacagctcag acaccgagag catcccctct cctcacactg aggccgccaa   2280
ggacacaggg cagaatgggc ccaagccccc agccaccctg ggcgccgacg ggccacccc   2340
aggcccaccc acccaccac ggaggacatc ccgggccccc attgagccca cccggcctc   2400
tgaagccacc ggagcccta cgccccacc agcaccccca tcgccctctg cacctcctcc   2460
tgtggtcccc aaggaggaga aggaggagga gaccgcagca gcgcccccag tggaggaggg   2520
ggaggagcag aagccccccg cggctgagga gctggcagtg gacacaggga aggccgagga   2580
gcccgtcaag agcgagtgca cggaggaagc cgaggagggg ccggccaagg gcaaggacgc   2640
ggaggccgct gaggccacgg ccgaggggc gctcaaggca gagaagaagg agggcgggag   2700
cggcagggcc accactgcca agagctcggg cgcccccag acagcgact ccagtgctac   2760
ctgcagtgca gacgaggtgg atgaggccga ggcggcgac aagaaccggc tgctgtcccc   2820
aaggcccagc ctcctcaccc cgactggcga ccccgggcc aatgcctcac cccagaagcc   2880
actggacctg aagcagctga agcagcgagc ggctgccatc cccccatcc aggtcaccaa   2940
agtccatgag ccccccggg aggacgcagc tcccaccaag ccagctcccc cagccccacc   3000
gccaccgcaa aacctgcagc cggagagcga cgcccctcag cagcctggca gcagcccccg   3060
gggcaagagc aggagcccgg cacccccgc cgacaaggag gccttcgcag ccgaggccca   3120
gaagctgcct ggggacccc cttgctggac ttcggcctg cccttccccg tgccccccg    3180
tgaggtgatc aaggcctccc cgcatgcccc ggaccccca gccttctcct acgctccacc   3240
```

-continued

```
tggtcaccca ctgcccctgg gcctccatga cactgcccgg cccgtcctgc cgcgcccacc     3300
caccatctcc aacccgcctc ccctcatctc ctctgccaag caccccagcg tcctcgagag     3360
gcaaataggt gccatctccc aaggaatgtc ggtccagctc cacgtcccgt actcagagca     3420
tgccaaggcc ccggtgggcc ctgtcaccat ggggctgccc ctgcccatgg accccaaaaa     3480
gctggcaccc ttcagcggag tgaagcagga gcagctgtcc ccacggggcc aggctgggcc     3540
accggagagc ctgggggtgc ccacagccca ggaggcgtcg tgctgagag gacagctct      3600 gggctcagtt ccggcggaa gcatcaccaa aggcattccc agcacacggg tgccctcgga      3660
cagcgccatc acataccgcg gctccatcac ccacggcacg ccagctgacg tcctgtacaa     3720
gggcaccatc accaggatca tcggcgagga cagcccgagt cgcttggacc gcggccggga     3780
ggacagcctg cccaagggcc acgtcatcta cgaaggcaag aagggccacg tcttgtccta     3840
tgagggtggc atgtctgtga cccagtgctc caaggaggac ggcagaagca gctcaggacc     3900
cccccatgag acgccgccc caagcgcac ctatgacatg atggagggcc gcgtgggcag       3960
agccatctcc tcagccagca tcgaaggtct catgggccgt gccatcccgc cggagcgaca     4020
cagcccccac cacctcaaag agcagcacca catccgcggg tccatcacac aagggatccc     4080
tcggtcctac gtggaggcac aggaggacta cctgcgtcgg gaggccaagc tcctaaagcg     4140
ggagggcacg cctccgcccc caccgccctc acgggacctg accgaggcct acaagacgca     4200
ggccctgggc cccctgaagc tgaagccggc ccatgagggc ctggtggcca cggtgaagga     4260
ggcgggccgc tccatccatg agatcccgcg cgaggagctg cggcacacgc ccgagctgcc     4320
cctggccccg cggccgctca aggagggctc catcacgcag ggcacccccgc tcaagtacga    4380 caccggcgcg tccaccactg gctccaaaaa gcacgacgta cgctccctca tcggcagccc     4440
cggccggacg ttcccacccg tgcacccgct ggatgtgatg gccgacgccc gggcactgga     4500
acgtgcctgc tacgaggaga gcctgaagag ccggccaggg accgcagca gctcgggggg     4560 ctccattgcg cgcggcgccc cggtcattgt gcctgagctg ggtaagccgc ggcagagccc     4620
cctgacctat gaggaccacg gggcacccctt tgccggccac ctcccacgag gttcgcccgt    4680
gaccatgcgg gagcccacgc cgcgcctgca ggagggcagc ctttcgtcca gcaaggcatc     4740
ccaggaccga aagctgacgt cgacgcctcg tgagatcgcc aagtcccgc acagcaccgt      4800 gcccgagcac cacccacacc ccatctcgcc ctatgagcac ctgcttcggg gcgtgagtgg     4860
cgtggacctg tatcgcagcc acatcccccct ggccttcgac cccacctcca taccccgcgg   4920
catccctctg gacgcagccg ctgcctacta cctgccccga cacctggccc caacccccac    4980
ctacccgcac ctgtacccac cctacctcat ccgcggctac cccgacacgg cggcgctgga    5040
gaaccggcag accatcatca tgactacat cacctcgcag cagatgcacc acaacacggc     5100
caccgccatg gcccagcgag ctgatatgct gagggggcctc tcgccccgcg agtcctcgct    5160
ggcactcaac tacgctgcgg gtccccgagg catcatcgac ctgtcccaag tgccacacct    5220
gcctgtgctc gtgccccga caccaggcac cccagccacc gccatggacc gccttgccta     5280
cctccccacc gcgcccagc ccttcagcag ccgccacagc agctcccac tctccccagg      5340 aggtccaaca cacttgacaa aaccaaccac cacgtcctcg tccgagcggg agcgagaccg    5400
ggatcgagag cgggaccggg atcgggagcg ggaaaagtcc atcctcacgt ccaccacgac    5460
ggtggagcac gcacccatct ggagacctgg tacagagcag agcagcggca gcagcggcag    5520
cagcggcggg ggtgggggca gcagcagccg ccccgcctcc cactcccatg cccaccagca    5580
ctcgcccatc tcccctcgga cccaggatgc cctccagcag agacccagtg tgcttcacaa    5640
```

```
cacaggcatg aagggtatca tcaccgctgt ggagcccagc aagcccacgg tcctgaggtc   5700
cacctccacc tcctcacccg ttcgcccagc tgccacattc ccacctgcca cccactgccc   5760
actgggcggc accctcgatg gggtctaccc taccctcatg gagcccgtct tgctgcccaa   5820
ggaggccccc cgggtcgccc ggccagagcg gccccgagca gacaccggcc atgccttcct   5880
cgccaagccc ccagcccgct ccgggctgga gcccgcctcc tcccccagca agggctcgga   5940
gccccggccc ctagtgcctc ctgtctctgg ccacgccacc atcgcccgca cccctgcgaa   6000
gaacctcgca cctcaccacg ccagcccgga cccgccggcg ccacctgcct cggcctcgga   6060
cccgcaccgg gaaaagactc aaagtaaacc cttttccatc caggaactgg aactccgttc   6120
tctgggttac cacggcagca gctacagccc cgaaggggtg gagcccgtca gccctgtgag   6180
ctcacccagt ctgacccacg acaagggct ccccaagcac ctggaagagc tcgacaagag   6240
ccacctggag gggagctgc ggcccaagca gccaggcccc gtgaagcttg cggggaggc   6300 cgcccacctc ccacacctgc ggccgctgcc tgagagccag ccctcgtcca gcccgctgct   6360
ccagaccgcc ccaggggtca aggtcacca gcgggtggtc accctggccc agcacatcag   6420
tgaggtcatc acacaggact acacccggca ccacccacag cagctcagcg caccccctgcc   6480 cgccccctc tactccttcc ctggggccag ctgccccgtc ctggacctcc gccgcccacc   6540
cagtgacctc tacctcccgc ccccggacca tggtgccccg gccgtggct cccccacag   6600 cgaaggggc aagaggtctc cagagccaaa caagacgtcg gtcttgggtg gtggtgagga   6660
cggtattgaa cctgtgtccc caccggaggg catgacggga ccagggcact cccggagtgc   6720
tgtgtacccg ctgctgtacc gggatgggga acagacggag cccagcagga tgggctccaa   6780
gtctccaggc aacaccagcc agccgccagc cttcttcagc aagctgaccg agagcaactc   6840
cgccatggtc aagtccaaga agcaagagat caacaagaag ctgaacaccc acaaccggaa   6900
tgagcctgaa tacaatatca gccagcctgg gacggagatc ttcaatatgc ccgccatcac   6960
cggaacaggc cttatgacct atagaagcca ggcggtgcag aacatgcca gcaccaacat   7020 ggggctggag gccataatta gaaaggcact catgggtaaa tatgaccagt gggaagagtc   7080
cccgccgctc agcgccaatg cttttaaccc tctgaatgcc agtgccagcc tgcccgctgc   7140
tatgcccata accgctgctg acggacggag tgaccacaca ctcacctcgc caggtggcgg   7200
cgggaaggcc aaggtctctg cagacccag cagccgaaaa gccaagtccc cggccccggg   7260
cctggcatct ggggaccggc caccctctgt ctcctcagtg cactcggagg gagactgcaa   7320
ccgccggacg ccgctcacca accgcgtgtg ggaggacagg ccctcgtccg caggttccac   7380
gccattcccc tacaaccccc tgatcatgcg gctgcaggcg ggtgtcatgg cttccccacc   7440
cccaccgggc ctcccgcgcg gcagcgggcc cctcgctggc cccaccacg cctgggacga   7500 ggagcccaag ccactgctct gctcgcagta cgagacactc tccgacagcg agtgactcag   7560
aacagggcgg gggggggcgg gcggtgtcag gtcccagcga gccacaggaa cggccctgca   7620
ggagcggggc ggctgccgac tcccccaacc aaggaaggag ccctgagtc cgcctgcgcc   7680 tccatccatc tgtccgtcca gagccggcat ccttgcctgt ctaaagcctt aactaagact   7740
cccgccccgg gctggccctg tgcagacctt actcagggga tgtttacctg gtgctcggga   7800
agggagggga aggggccggg gaggggggcac ggcaggcgtg tggcagccac acacaggcgg   7860
ccagggcggc cagggaccca aagcaggatg accacgcacc tccacgccac tgcctccccc   7920
gaatgcattt ggaaccaaag tctaaactga gctcgcagcc ccgcgccct ccctccgcct   7980
```

```
cccatcccgc ttagcgctct ggacagatgg acgcaggccc tgtccagccc ccagtgcgct    8040
cgttccggtc cccacagact gccccagcca acgagattgc tggaaaccaa gtcaggccag    8100
gtgggcggac aaaagggcca ggtgcggcct gggggaacg gatgctccga ggactggact    8160 gttttttca cacatcgttg ccgcagcggt gggaaggaaa ggcagatgta aatgatgtgt    8220
tggtttacag ggtatatttt tgataccttc aatgaattaa ttcagatgtt ttacgcaagg    8280
aaggacttac ccagtattac tgctgctgtg cttttgatct ctgcttaccg ttcaagaggc    8340
gtgtgcaggc cgacagtcgg tgaccccatc actcgcagga ccaagggggc ggggactgct    8400
cgtcacgccc cgctgtgtcc tccctccctc ccttccttgg gcagaatgaa ttcgatgcgt    8460
attctgtggc cgccatttgc gcaggtggt ggtattctgt catttacaca cgtcgttcta    8520
attaaaaagc gaattatact ccaaaaaaaa aaaaaaaaa a                         8561
```

<210> SEQ ID NO 5
<211> LENGTH: 2517
<212> TYPE: PRT
<213> ORGANISM: Homo sapiens

<400> SEQUENCE: 5

```
Met Ser Gly Ser Thr Gln Leu Val Ala Gln Thr Trp Arg Ala Thr Glu
  1               5                  10                  15

Pro Arg Tyr Pro Pro His Ser Leu Ser Tyr Pro Val Gln Ile Ala Arg
             20                  25                  30

Thr His Thr Asp Val Gly Leu Leu Glu Tyr Gln His His Ser Arg Asp
         35                  40                  45

Tyr Ala Ser His Leu Ser Pro Gly Ser Ile Ile Gln Pro Gln Arg Arg
     50                  55                  60

Arg Pro Ser Leu Leu Ser Glu Phe Gln Pro Gly Asn Glu Arg Ser Gln
 65                  70                  75                  80

Glu Leu His Leu Arg Pro Glu Ser His Ser Tyr Leu Pro Glu Leu Gly
                 85                  90                  95

Lys Ser Glu Met Glu Phe Ile Glu Ser Lys Arg Pro Arg Leu Glu Leu
            100                 105                 110

Leu Pro Asp Pro Leu Leu Arg Pro Ser Pro Leu Leu Ala Thr Gly Gln
        115                 120                 125

Pro Ala Gly Ser Glu Asp Leu Thr Lys Asp Arg Ser Leu Thr Gly Lys
    130                 135                 140

Leu Glu Pro Val Ser Pro Pro Ser Pro Pro His Thr Asp Pro Glu Leu
145                 150                 155                 160

Glu Leu Val Pro Pro Arg Leu Ser Lys Glu Glu Leu Ile Gln Asn Met
                165                 170                 175

Asp Arg Val Asp Arg Glu Ile Thr Met Val Glu Gln Gln Ile Ser Lys
            180                 185                 190

Leu Lys Lys Lys Gln Gln Gln Leu Glu Glu Glu Ala Ala Lys Pro Pro
        195                 200                 205

Glu Pro Glu Lys Pro Val Ser Pro Pro Ile Glu Ser Lys His Arg
    210                 215                 220

Ser Leu Val Gln Ile Ile Tyr Asp Glu Asn Arg Lys Lys Ala Glu Ala
225                 230                 235                 240

Ala His Arg Ile Leu Glu Gly Leu Gly Pro Gln Val Glu Leu Pro Leu
                245                 250                 255

Tyr Asn Gln Pro Ser Asp Thr Arg Gln Tyr His Glu Asn Ile Lys Ile
            260                 265                 270
```

```
Asn Gln Ala Met Arg Lys Lys Leu Ile Leu Tyr Phe Lys Arg Arg Asn
            275                 280                 285

His Ala Arg Lys Gln Trp Lys Gln Lys Phe Cys Gln Arg Tyr Asp Gln
            290                 295                 300

Leu Met Glu Ala Leu Glu Lys Lys Val Glu Arg Ile Glu Asn Asn Pro
305                 310                 315                 320

Arg Arg Arg Ala Lys Glu Ser Lys Val Arg Glu Tyr Tyr Glu Lys Gln
                    325                 330                 335

Phe Pro Glu Ile Arg Lys Gln Arg Glu Leu Gln Glu Arg Met Gln Ser
                340                 345                 350

Arg Val Gly Gln Arg Gly Ser Gly Leu Ser Met Ser Ala Ala Arg Ser
                355                 360                 365

Glu His Glu Val Ser Glu Ile Ile Asp Gly Leu Ser Glu Gln Glu Asn
            370                 375                 380

Leu Glu Lys Gln Met Arg Gln Leu Ala Val Ile Pro Pro Met Leu Tyr
385                 390                 395                 400

Asp Ala Asp Gln Gln Arg Ile Lys Phe Ile Asn Met Asn Gly Leu Met
                    405                 410                 415

Ala Asp Pro Met Lys Val Tyr Lys Asp Arg Gln Val Met Asn Met Trp
                420                 425                 430

Ser Glu Gln Glu Lys Glu Thr Phe Arg Glu Lys Phe Met Gln His Pro
            435                 440                 445

Lys Asn Phe Gly Leu Ile Ala Ser Phe Leu Glu Arg Lys Thr Val Ala
            450                 455                 460

Glu Cys Val Leu Tyr Tyr Tyr Leu Thr Lys Lys Asn Glu Asn Tyr Lys
465                 470                 475                 480

Ser Leu Val Arg Arg Ser Tyr Arg Arg Arg Gly Lys Ser Gln Gln Gln
                    485                 490                 495

Gln Gln Gln Gln Gln Gln Gln Gln Gln Gln Gln Gln Gln Gln Pro Met
                500                 505                 510

Pro Arg Ser Ser Gln Glu Glu Lys Asp Glu Lys Glu Lys Glu Lys Glu
            515                 520                 525

Ala Glu Lys Glu Glu Glu Lys Pro Glu Val Glu Asn Asp Lys Glu Asp
530                 535                 540

Leu Leu Lys Glu Lys Thr Asp Asp Thr Ser Gly Glu Asp Asn Asp Glu
545                 550                 555                 560

Lys Glu Ala Val Ala Ser Lys Gly Arg Lys Thr Ala Asn Ser Gln Gly
                565                 570                 575

Arg Arg Lys Gly Arg Ile Thr Arg Ser Met Ala Asn Glu Ala Asn Ser
                580                 585                 590

Glu Glu Ala Ile Thr Pro Gln Gln Ser Ala Glu Leu Ala Ser Met Glu
            595                 600                 605

Leu Asn Glu Ser Ser Arg Trp Thr Glu Glu Met Glu Thr Ala Lys
610                 615                 620

Lys Gly Leu Leu Glu His Gly Arg Asn Trp Ser Ala Ile Ala Arg Met
625                 630                 635                 640

Val Gly Ser Lys Thr Val Ser Gln Cys Lys Asn Phe Tyr Phe Asn Tyr
                    645                 650                 655

Lys Lys Arg Gln Asn Leu Asp Glu Ile Leu Gln Gln His Lys Leu Lys
                660                 665                 670

Met Glu Lys Glu Arg Asn Ala Arg Arg Lys Lys Lys Ala Pro Ala
            675                 680                 685

Ala Ala Ser Glu Glu Ala Ala Phe Pro Pro Val Val Glu Asp Glu Glu
```

-continued

```
            690                 695                 700
Met Glu Ala Ser Gly Val Ser Gly Asn Glu Glu Met Val Glu Glu
705                 710                 715                 720

Ala Glu Ala Leu His Ala Ser Gly Asn Glu Val Pro Arg Gly Glu Cys
                725                 730                 735

Ser Gly Pro Ala Thr Val Asn Asn Ser Ser Asp Thr Glu Ser Ile Pro
                740                 745                 750

Ser Pro His Thr Glu Ala Ala Lys Asp Thr Gly Gln Asn Gly Pro Lys
                755                 760                 765

Pro Pro Ala Thr Leu Gly Ala Asp Gly Pro Pro Gly Pro Pro Thr
770                 775                 780

Pro Pro Arg Arg Thr Ser Arg Ala Pro Ile Glu Pro Thr Pro Ala Ser
785                 790                 795                 800

Glu Ala Thr Gly Ala Pro Thr Pro Pro Ala Pro Pro Ser Pro Ser
                805                 810                 815

Ala Pro Pro Val Val Pro Lys Glu Lys Glu Glu Glu Thr Ala
                820                 825                 830

Ala Ala Pro Pro Val Glu Glu Gly Glu Glu Gln Lys Pro Pro Ala Ala
                835                 840                 845

Glu Glu Leu Ala Val Asp Thr Gly Lys Ala Glu Glu Pro Val Lys Ser
850                 855                 860

Glu Cys Thr Glu Glu Ala Glu Glu Gly Pro Ala Lys Gly Lys Asp Ala
865                 870                 875                 880

Glu Ala Ala Glu Ala Thr Ala Glu Gly Ala Leu Lys Ala Glu Lys Lys
                885                 890                 895

Glu Gly Gly Ser Gly Arg Ala Thr Thr Ala Lys Ser Ser Gly Ala Pro
                900                 905                 910

Gln Asp Ser Asp Ser Ser Ala Thr Cys Ser Ala Asp Glu Val Asp Glu
                915                 920                 925

Ala Glu Gly Gly Asp Lys Asn Arg Leu Leu Ser Pro Arg Pro Ser Leu
                930                 935                 940

Leu Thr Pro Thr Gly Asp Pro Arg Ala Asn Ala Ser Pro Gln Lys Pro
945                 950                 955                 960

Leu Asp Leu Lys Gln Leu Lys Gln Arg Ala Ala Ile Pro Pro Ile
                965                 970                 975

Gln Val Thr Lys Val His Glu Pro Pro Arg Glu Asp Ala Ala Pro Thr
                980                 985                 990

Lys Pro Ala Pro Pro Ala Pro Pro Pro Gln Asn Leu Gln Pro Glu
                995                 1000                1005

Ser Asp Ala Pro Gln Gln Pro Gly Ser Ser Pro Arg Gly Lys Ser Arg
                1010                1015                1020

Ser Pro Ala Pro Ala Asp Lys Glu Ala Phe Ala Ala Glu Ala Gln
1025                1030                1035                1040

Lys Leu Pro Gly Asp Pro Pro Cys Trp Thr Ser Gly Leu Pro Phe Pro
                1045                1050                1055

Val Pro Pro Arg Glu Val Ile Lys Ala Ser Pro His Ala Pro Asp Pro
                1060                1065                1070

Ser Ala Phe Ser Tyr Ala Pro Pro Gly His Pro Leu Pro Leu Gly Leu
                1075                1080                1085

His Asp Thr Ala Arg Pro Val Leu Pro Arg Pro Pro Thr Ile Ser Asn
                1090                1095                1100

Pro Pro Pro Leu Ile Ser Ser Ala Lys His Pro Ser Val Leu Glu Arg
1105                1110                1115                1120
```

```
Gln Ile Gly Ala Ile Ser Gln Gly Met Ser Val Gln Leu His Val Pro
            1125                1130                1135

Tyr Ser Glu His Ala Lys Ala Pro Val Gly Pro Val Thr Met Gly Leu
        1140                1145                1150

Pro Leu Pro Met Asp Pro Lys Lys Leu Ala Pro Phe Ser Gly Val Lys
    1155                1160                1165

Gln Glu Gln Leu Ser Pro Arg Gly Gln Ala Gly Pro Pro Glu Ser Leu
1170                1175                1180

Gly Val Pro Thr Ala Gln Glu Ala Ser Val Leu Arg Gly Thr Ala Leu
1185                1190                1195                1200

Gly Ser Val Pro Gly Gly Ser Ile Thr Lys Gly Ile Pro Ser Thr Arg
            1205                1210                1215

Val Pro Ser Asp Ser Ala Ile Thr Tyr Arg Gly Ser Ile Thr His Gly
        1220                1225                1230

Thr Pro Ala Asp Val Leu Tyr Lys Gly Thr Ile Thr Arg Ile Ile Gly
    1235                1240                1245

Glu Asp Ser Pro Ser Arg Leu Asp Arg Gly Arg Glu Asp Ser Leu Pro
1250                1255                1260

Lys Gly His Val Ile Tyr Glu Gly Lys Lys Gly His Val Leu Ser Tyr
1265                1270                1275                1280

Glu Gly Gly Met Ser Val Thr Gln Cys Ser Lys Glu Asp Gly Arg Ser
            1285                1290                1295

Ser Ser Gly Pro Pro His Glu Thr Ala Ala Pro Lys Arg Thr Tyr Asp
        1300                1305                1310

Met Met Glu Gly Arg Val Gly Arg Ala Ile Ser Ser Ala Ser Ile Glu
    1315                1320                1325

Gly Leu Met Gly Arg Ala Ile Pro Pro Glu Arg His Ser Pro His His
1330                1335                1340

Leu Lys Glu Gln His His Ile Arg Gly Ser Ile Thr Gln Gly Ile Pro
1345                1350                1355                1360

Arg Ser Tyr Val Glu Ala Gln Glu Asp Tyr Leu Arg Arg Glu Ala Lys
            1365                1370                1375

Leu Leu Lys Arg Glu Gly Thr Pro Pro Pro Pro Pro Ser Arg Asp
        1380                1385                1390

Leu Thr Glu Ala Tyr Lys Thr Gln Ala Leu Gly Pro Leu Lys Leu Lys
    1395                1400                1405

Pro Ala His Glu Gly Leu Val Ala Thr Val Lys Glu Ala Gly Arg Ser
1410                1415                1420

Ile His Glu Ile Pro Arg Glu Glu Leu Arg His Thr Pro Glu Leu Pro
1425                1430                1435                1440

Leu Ala Pro Arg Pro Leu Lys Glu Gly Ser Ile Thr Gln Gly Thr Pro
            1445                1450                1455

Leu Lys Tyr Asp Thr Gly Ala Ser Thr Thr Gly Ser Lys Lys His Asp
        1460                1465                1470

Val Arg Ser Leu Ile Gly Ser Pro Gly Arg Thr Phe Pro Pro Val His
    1475                1480                1485

Pro Leu Asp Val Met Ala Asp Ala Arg Ala Leu Glu Arg Ala Cys Tyr
1490                1495                1500

Glu Glu Ser Leu Lys Ser Arg Pro Gly Thr Ala Ser Ser Ser Gly Gly
1505                1510                1515                1520

Ser Ile Ala Arg Gly Ala Pro Val Ile Val Pro Glu Leu Gly Lys Pro
            1525                1530                1535
```

-continued

```
Arg Gln Ser Pro Leu Thr Tyr Glu Asp His Gly Ala Pro Phe Ala Gly
        1540                1545                1550

His Leu Pro Arg Gly Ser Pro Val Thr Met Arg Glu Pro Thr Pro Arg
        1555                1560                1565

Leu Gln Glu Gly Ser Leu Ser Ser Ser Lys Ala Ser Gln Asp Arg Lys
        1570                1575                1580

Leu Thr Ser Thr Pro Arg Glu Ile Ala Lys Ser Pro His Ser Thr Val
1585                1590                1595                1600

Pro Glu His His Pro His Pro Ile Ser Pro Tyr Glu His Leu Leu Arg
                1605                1610                1615

Gly Val Ser Gly Val Asp Leu Tyr Arg Ser His Ile Pro Leu Ala Phe
        1620                1625                1630

Asp Pro Thr Ser Ile Pro Arg Gly Ile Pro Leu Asp Ala Ala Ala Ala
        1635                1640                1645

Tyr Tyr Leu Pro Arg His Leu Ala Pro Asn Pro Thr Tyr Pro His Leu
    1650                1655                1660

Tyr Pro Pro Tyr Leu Ile Arg Gly Tyr Pro Asp Thr Ala Ala Leu Glu
1665                1670                1675                1680

Asn Arg Gln Thr Ile Ile Asn Asp Tyr Ile Thr Ser Gln Gln Met His
                1685                1690                1695

His Asn Thr Ala Thr Ala Met Ala Gln Arg Ala Asp Met Leu Arg Gly
        1700                1705                1710

Leu Ser Pro Arg Glu Ser Ser Leu Ala Leu Asn Tyr Ala Ala Gly Pro
        1715                1720                1725

Arg Gly Ile Ile Asp Leu Ser Gln Val Pro His Leu Pro Val Leu Val
        1730                1735                1740

Pro Pro Thr Pro Gly Thr Pro Ala Thr Ala Met Asp Arg Leu Ala Tyr
1745                1750                1755                1760

Leu Pro Thr Ala Pro Gln Pro Phe Ser Ser Arg His Ser Ser Ser Pro
                1765                1770                1775

Leu Ser Pro Gly Gly Pro Thr His Leu Thr Lys Pro Thr Thr Thr Ser
        1780                1785                1790

Ser Ser Glu Arg Glu Arg Asp Arg Asp Arg Glu Arg Asp Arg Asp Arg
        1795                1800                1805

Glu Arg Glu Lys Ser Ile Leu Thr Ser Thr Thr Thr Val Glu His Ala
        1810                1815                1820

Pro Ile Trp Arg Pro Gly Thr Glu Gln Ser Ser Gly Ser Ser Gly Ser
1825                1830                1835                1840

Ser Gly Gly Gly Gly Ser Ser Ser Arg Pro Ala Ser His Ser His
                1845                1850                1855

Ala His Gln His Ser Pro Ile Ser Pro Arg Thr Gln Asp Ala Leu Gln
        1860                1865                1870

Gln Arg Pro Ser Val Leu His Asn Thr Gly Met Lys Gly Ile Ile Thr
        1875                1880                1885

Ala Val Glu Pro Ser Lys Pro Thr Val Leu Arg Ser Thr Ser Thr Ser
        1890                1895                1900

Ser Pro Val Arg Pro Ala Ala Thr Phe Pro Ala Thr His Cys Pro
1905                1910                1915                1920

Leu Gly Gly Thr Leu Asp Gly Val Tyr Pro Thr Leu Met Glu Pro Val
                1925                1930                1935

Leu Leu Pro Lys Glu Ala Pro Arg Val Ala Arg Pro Glu Arg Pro Arg
        1940                1945                1950

Ala Asp Thr Gly His Ala Phe Leu Ala Lys Pro Pro Ala Arg Ser Gly
```

-continued

```
            1955                1960                1965

Leu Glu Pro Ala Ser Ser Pro Ser Lys Gly Ser Glu Pro Arg Pro Leu
    1970                1975                1980

Val Pro Pro Val Ser Gly His Ala Thr Ile Ala Arg Thr Pro Ala Lys
1985                1990                1995                2000

Asn Leu Ala Pro His His Ala Ser Pro Asp Pro Pro Ala Pro Pro Ala
            2005                2010                2015

Ser Ala Ser Asp Pro His Arg Glu Lys Thr Gln Ser Lys Pro Phe Ser
            2020                2025                2030

Ile Gln Glu Leu Glu Leu Arg Ser Leu Gly Tyr His Gly Ser Ser Tyr
    2035                2040                2045

Ser Pro Glu Gly Val Glu Pro Val Ser Pro Val Ser Ser Pro Ser Leu
    2050                2055                2060

Thr His Asp Lys Gly Leu Pro Lys His Leu Glu Glu Leu Asp Lys Ser
2065                2070                2075                2080

His Leu Glu Gly Glu Leu Arg Pro Lys Gln Pro Gly Pro Val Lys Leu
            2085                2090                2095

Gly Gly Glu Ala Ala His Leu Pro His Leu Arg Pro Leu Pro Glu Ser
            2100                2105                2110

Gln Pro Ser Ser Ser Pro Leu Leu Gln Thr Ala Pro Gly Val Lys Gly
            2115                2120                2125

His Gln Arg Val Val Thr Leu Ala Gln His Ile Ser Glu Val Ile Thr
    2130                2135                2140

Gln Asp Tyr Thr Arg His His Pro Gln Gln Leu Ser Ala Pro Leu Pro
2145                2150                2155                2160

Ala Pro Leu Tyr Ser Phe Pro Gly Ala Ser Cys Pro Val Leu Asp Leu
            2165                2170                2175

Arg Arg Pro Pro Ser Asp Leu Tyr Leu Pro Pro Pro Asp His Gly Ala
            2180                2185                2190

Pro Ala Arg Gly Ser Pro His Ser Glu Gly Gly Lys Arg Ser Pro Glu
            2195                2200                2205

Pro Asn Lys Thr Ser Val Leu Gly Gly Gly Glu Asp Gly Ile Glu Pro
    2210                2215                2220

Val Ser Pro Pro Glu Gly Met Thr Glu Pro Gly His Ser Arg Ser Ala
2225                2230                2235                2240

Val Tyr Pro Leu Leu Tyr Arg Asp Gly Glu Gln Thr Glu Pro Ser Arg
            2245                2250                2255

Met Gly Ser Lys Ser Pro Gly Asn Thr Ser Gln Pro Pro Ala Phe Phe
            2260                2265                2270

Ser Lys Leu Thr Glu Ser Asn Ser Ala Met Val Lys Ser Lys Lys Gln
    2275                2280                2285

Glu Ile Asn Lys Lys Leu Asn Thr His Asn Arg Asn Glu Pro Glu Tyr
    2290                2295                2300

Asn Ile Ser Gln Pro Gly Thr Glu Ile Phe Asn Met Pro Ala Ile Thr
2305                2310                2315                2320

Gly Thr Gly Leu Met Thr Tyr Arg Ser Gln Ala Val Gln Glu His Ala
            2325                2330                2335

Ser Thr Asn Met Gly Leu Glu Ala Ile Ile Arg Lys Ala Leu Met Gly
            2340                2345                2350

Lys Tyr Asp Gln Trp Glu Glu Ser Pro Pro Leu Ser Ala Asn Ala Phe
    2355                2360                2365

Asn Pro Leu Asn Ala Ser Ala Ser Leu Pro Ala Ala Met Pro Ile Thr
    2370                2375                2380
```

-continued

```
Ala Ala Asp Gly Arg Ser Asp His Thr Leu Thr Ser Pro Gly Gly Gly
2385                2390                2395                2400

Gly Lys Ala Lys Val Ser Gly Arg Pro Ser Ser Arg Lys Ala Lys Ser
            2405                2410                2415

Pro Ala Pro Gly Leu Ala Ser Gly Asp Arg Pro Ser Val Ser Ser
        2420                2425                2430

Val His Ser Glu Gly Asp Cys Asn Arg Arg Thr Pro Leu Thr Asn Arg
    2435                2440                2445

Val Trp Glu Asp Arg Pro Ser Ser Ala Gly Ser Thr Pro Phe Pro Tyr
2450                2455                2460

Asn Pro Leu Ile Met Arg Leu Gln Ala Gly Val Met Ala Ser Pro Pro
2465                2470                2475                2480

Pro Pro Gly Leu Pro Ala Gly Ser Gly Pro Leu Ala Gly Pro His His
            2485                2490                2495

Ala Trp Asp Glu Glu Pro Lys Pro Leu Leu Cys Ser Gln Tyr Glu Thr
            2500                2505                2510

Leu Ser Asp Ser Glu
        2515

<210> SEQ ID NO 6
<211> LENGTH: 8388
<212> TYPE: DNA
<213> ORGANISM: Mus musculus
<220> FEATURE:
<221> NAME/KEY: modified_base
<222> LOCATION: (109)
<223> OTHER INFORMATION: a, c, t, g, other or unknown
<220> FEATURE:
<221> NAME/KEY: modified_base
<222> LOCATION: (8173)
<223> OTHER INFORMATION: a, c, t, g, other or unknown
<220> FEATURE:
<221> NAME/KEY: modified_base
<222> LOCATION: (8180)
<223> OTHER INFORMATION: a, c, t, g, other or unknown
<220> FEATURE:
<221> NAME/KEY: modified_base
<222> LOCATION: (8302)
<223> OTHER INFORMATION: a, c, t, g, other or unknown
<220> FEATURE:
<221> NAME/KEY: modified_base
<222> LOCATION: (8343)
<223> OTHER INFORMATION: a, c, t, g, other or unknown
<220> FEATURE:
<221> NAME/KEY: modified_base
<222> LOCATION: (8359)
<223> OTHER INFORMATION: a, c, t, g, other or unknown
<220> FEATURE:
<221> NAME/KEY: modified_base
<222> LOCATION: (8384)
<223> OTHER INFORMATION: a, c, t, g, other or unknown

<400> SEQUENCE: 6
cttaaaaaaa aaaccccttac ttgtggttaa aggaaaagaa ataaagactt aggaaaaatg      60
taattttcca gggggtacct acacccaaga catatggttc tcaagaggna ctcagcatat     120
cactttgatt ccagagaagc tacaaaagtc attaccaaac tccaggctgg aaagcagtgc     180
tcatactaaa tatttaaaca tttaaagacc tgattaagag acatcaaagg ctttatacca     240
ggggcacacc aacagagaca ggcttttca aggataattt atgtctgccc attgtcttct     300
ggcttaggag acatagaggg aaacatcacc taggaaaacc agtaaccaat gtgtaccatc     360
caggagttat tctatgacaa aaccaaaagt tttgttcttg tgtacttctc tgtgcaccat     420
ctttctatat ctatttagaa aacaaaacaa attttggtaa cacgcttgtg tataaagagc     480
```

-continued

```
aggacagcgg tgtcacagat caacctagaa agtaattatt taacgagtaa atgactcata    540
taggacaagg caagctgtga cttttcaacct gttctgtctc gtgccgaatt cggcacgagc   600
caaagcctac ctggacccta ccaccatgtc aggatccaca cagcctgtgg cacagacatg    660
gcgggctgct gagccccgct acccacccca tggcatctcc tacccggtgc agatagcccg    720
gtcccacacg gacgtgggc tgcttgagta ccaacaccac ccccgtgact acacctcaca     780
cctgtcaccc ggttccatca tccagccaca gaggaggcgg ccctcactgc tgtcagagtt    840
ccagcctggg agtgaacggt ctcaggagct ccacctgcgc cctgagtccc gcacgttcct    900
gcctgagctg ggcaagcccg acatagaatt caccgagagc aagcgccccc gcctggagct    960
actaccgat accctgctgc gcccatcacc cctgctggcc actgggcagc cgagtgggtc    1020
tgaagacctt accaaggacc gtagcctggc aggcaagctg gagcctgtgt cacctcccag    1080
tccccgcac gctgaccctg agctagagct ggcgccatct cgactgtcca aggaggagct    1140
gatccagaac atggaccgcg tggaccgtga gatcaccatg gtagagcagc agatctccaa    1200
gctgaagaag aagcagcaac agttggagga ggaggccgcc aagccgcccg aacccgagaa    1260
gcctgtgtcg ccaccaccca tagaatcaaa gcaccgaagc ctggtccaga tcatctacga    1320
tgagaaccgg aagaaagccg aagccgcaca ccggatccta aaggcctgg ggccccaggt     1380
ggagctgcct ctgtacaacc agccgtctga cacacgccag taccatgaaa acatcaaaat    1440
aaaccaggcg atgcggaaga agctgatctt gtactttaag cggaggaacc acgcgcgcaa    1500
gcagtgggaa cagcgcttct gccagcgcta tgaccagctc atggaggcgt gggagaagaa    1560
ggtagagcgc atagagaaca atccgcgaag gagggccaag gagagcaagg tgagggagta    1620
ctacgagaaa cagttcccgg agatccgcaa gcagcgggag ctgcaggagc gcatgcgagag   1680
cagggtgggc cagcgtggca gtgggctctc catgtcggct gcccgcagtg agcatgaggt    1740
ttctgagatc attgatggct tgtctgagca ggagaacctg gagaagcaga tgcgccagct    1800
ggccgtgatc ccgcccatgt tgtacgacgc ggaccagcag aggatcaagt tcatcaacat    1860
gaatggactc atggatgacc ccatgaaggt ctacaaggac cgtcaggtta ccaacatgtg    1920
gagcgagcag gagagggaca ccttccgtga aagtttatg cagcacccta gaactttgg     1980
cctgattgcc tcattcctgg agagaaagac ggtcgctgag tgtgtcctct attactacct    2040
gaccaagaag aatgaaaatt caagagctt ggtgaggcgg agctatcggc gccgtggcaa     2100
gagccagcag cagcagcagc agcaacaaca gcagcagcag cagcagatgg cacgagcag     2160
ccaggaggag aaggaggaga aggagaagga aaggaggcc gacaaggagg aagagaagca     2220
ggatgcggag aacgagaagg aagaactcag caaggagaag acagacgaca cttctggcga    2280
ggacaaccat gagaaagagg ccgtggcctc caaaggccgc aaaactgcca acagccaagg    2340
ccgccgcaaa ggccgtatca cgcgctccat ggccaacgag gccaaccatg aggagacagc    2400
cacccccacag caaagttcag agctggcttc catggagatg aacgagagtt ctcgctggac    2460
tgaggaagag atggagacag caaagaaagg cctcctggaa catgggagga actggtcagc    2520
cattgcccgc atggtgggct ccaagaccgt gtcccagtgt aagaacttct acttcaacta    2580
caagaagagg cagaacctgg acgaaatcct tcagcagcac aagctaaaga tggaaggaa     2640
gaggaacgct cggaggaaga agaagaagac cccagctgcg gcgagcgagg agacagcctt    2700
cccacctgcc gctgaggacg aagagatgga agcatcaggc gcaagtgcca atgaggaaga    2760
gctggcggag gaggcagaag cctcacaggc ctctgggaat gaggttccca gagttgggga    2820
```

```
gtgcagtggc ccagctgctg tcaacaacag ctctgatact gagagtgtcc catccccgcg    2880
ttcagaagcc atgaaggaca ctgggcctaa acccactggc actgaagcat tgcccgctgc    2940
cacccagcca cctgttcctc ctccagaaga accggcagta gcccctgctg agccctcccc    3000
agtccctgat gccagtggcc caccatcccc agagccttcc catcacctgc cgcacccccg    3060
gctactgtgg acaaggatga acaagaagcc ccggctgctc cagctcccca gacagaggat    3120
gccaaggagc agaagtctga ggccgaggag atcgatgtgg aaaagccag aggagcccga    3180 ggcctctgag gagcccccgg agagtgtaaa gagtgaccac aaggaggaga ccgaggaaga    3240
gcctgaagac aaagccaagg gcacagaggc cattgaaact gtgtctgagg caccacttaa    3300
ggtggaggag gctggtagca aggcagctgt gaccaagggt tccagctcag gtgccaccca    3360
ggacagtgac ttcagtgcca cctgcagtgc cgatgaggtg gacgaacccg aaggaggtga    3420
caagggcagg ctgctgtcac caaggcccag cctcctcacc ccggctggag atccccgggc    3480
cagtacctcg ccccagaagc cgctggacct gaagcagctg aagcagcgag cagccgccat    3540 ccccccctatc caggtcacca aggtccatga gccccccgg gaggacacag taccccaaa    3600 gccagttccc cctgtgcctc cacccacgca gcacctacag ccagagggtg acgtgtctca    3660
gcagtcggga ggaagtccac gtggcaagtc ccgcagccca gtgcctcctg ccgagaaaga    3720
ggcagagaaa cccgcattct ttccggcttt cccaactgag ggcccaaagc taccgactga    3780
gcccccacgc tggtcatcgg gcctgccctt cccatccct ccacgggagg tgatcaagac    3840
ttccccacac gccgctgacc cctctgcctt ctcctacaca ccccccggtc accgctgcc    3900 tctgggcctc cacgatagtg cccggcccgt cctgccacgt ccccccatct ctaaccccc    3960 accctcatc tcctctgcca agcatcccgg cgtacttgag aggcagctgg gtgccatctc    4020
ccagcagggg atgtcagtcc agcttcgtgt gcctcactca gagcatgcca aggcccccat    4080
gggccctctc accatggggc tgccccttgc cgtggaccct aagaagctgg ggacagcact    4140
gggctccgcc accagtggaa gcatcaccaa gggcctcccc agtacccggg ctgcagacgg    4200
ccccagctac agaggctcta tcacccacgg cacgcccgca gacgtcctct acaagggtac    4260
catcagcagg atcgtcggtg aggacagccc aagtcgcctt gaccgggcac gagaggacac    4320
cctgcccaag ggccatgtca tctatgaggg caagaaaggc cacgtcctat cctatgaagg    4380
tggtatgtcc gtgtcacagt gctctaagga ggatggaagg agcagctcgg gcccacccca    4440
tgagactgcc gcccctaaac gcacctatga catgatggag ggccgtgtag gcaggactgt    4500
cacctcagcc agcatagagg gactcatggg ccgcgccatc cctgagcagc acagccccca    4560
cctcaaggag cagcatcaca tccgaggctc catcacgcaa ggcatcccga ggtcctatgt    4620
ggaggcgcag gaggactact tacggcggga ggccaagctc ttgaagcgag aagggacacc    4680 accacccca ccaccacctc gggacctgac tgagacctac aagccccggc ccctggaccc    4740
tctgggtccc ctgaagctga agccgactca cgagggtgtg gtagcaactg tgaaggaggc    4800
gggccgctct atccatgaga tcccgagaga ggagctgcgc cgcacacctg agctacccct    4860
ggcaccacgg cctctgaagg agggttccat cacccagggc accccactca agtacgactc    4920
tggggcaccc tccactggca ccaagaaaca cgacgtgcgc tccatcatcg gcagccccgg    4980
ccggcctttc cctgccctgc acccgctgga cataatggct gacgcccggg cactggagcg    5040
tgcctgctat gaagagagtc tgaagagccg gtcagggacc agcagtggtg caggggctc    5100 catcacacgt ggggctccag tcgtcgtgcc tgaactgggc aagccacggc aaagcccact    5160
gacttacgaa gaccacgggg cacccttcac cagtcacctg ccacgtggct ccctgtgac    5220
```

-continued

```
cacgagggag cccacgccac gccttcagga aggcagcctc ctatccagca aggcgtccca    5280
ggaccggaag ctgacatcta caccccggga gatcgccaag tccccacaca gcactgtgcc    5340
cgagcaccac cctcacccca tctcccccta tgagcacttg ctccggggcg tgactggtgt    5400
ggacctgtac cgtggtcaca tcccattggc ctttgacccc acctccatac cccgagggat    5460
ccctctggaa gcagcagccg cagcctacta cctgccccgg cacttggccc ccagccccac    5520
ctacccacac ctgtacccac cttacctcat ccgcggctac cctgacacgg cggccctgga    5580
gaaccgccac accatcatca atgactacat cacctcgcag cagatgcacc acaacgctgc    5640
ctccgccatg gcccagcgtg ctgacatgct gagggggtctg tcaccgcgag agtcctcgct    5700
ggccctcaat tatgccgctg cccaagagg cattatcgac ctgtcccaag tgccacacct    5760
gcccgtgctg gtgccaccaa cgccaggcac ccctgccacc gccatcgacc gccttgccta    5820
cctcccccact cgcgccccac ccttcagcag ccgccacagt agctcaccgc tgtccccagg    5880
aggcccccact cacctagcta aaccaactgc cacatcttca tcggagcggg aacgggaacg    5940
tgagcgggaa cgagacaagt ccatcctcac gtctaccact acagtggagc atgcacccat    6000
ctggagacct ggtacggagc agagcagcgg ggctgggggc agcagccgcc ccgcctccca    6060
caccaccag cactcgccca tctcccccg gacccaggac gccttgcagc agaggcccag    6120
tgtgctgcac aacacgagca tgaagggcgt ggtcacctcc gtggaacccg gcacgcccac    6180
ggtcctgagg tgggccaggt ccacctccac ctcttcgcct gtccgcccag ctgccacatt    6240
cccacctgcc acccactgcc cacttggtgg caccccttgaa ggggtctacc ctaccctcat    6300
ggagcccgtc ctgttaccca aggagacctc tcgggtcgcc cggcccgagc gggcccgggt    6360
ggacgctggc catgcctttc ttaccaaacc cccgggccgg gagcccgcct cctcacccag    6420
caagagctcc gagccccgat ccctagcacc cccagctcc agccacacag ccatcgcccg    6480
cacccccagca aagaaccttg caccccacca tgccagtccg gacccgccgg cgcccacctc    6540
ggcctcagat ctgcaccgag aaaagactca agtaaaccc ttttccatcc aggaattgga    6600
actccgttct ctgggttacc acagtggagc tggctacagc cccgatgggg tggagcccat    6660
cagcccggtg agctccccca gcctgaccca cgacaagggg ctctccaaac ctctggaaga    6720
gctagagaag agccacttgg aagggagct gcggcacaag cagccaggcc ccatgaagct    6780
cagcgcggag gctgccatc tcccacatct gcggcactg cccgagagcc agccctcatc    6840
cagcccactc ctccagactg ccccaggcat caaaggtcac cagagggtgg tcaccctggc    6900
tcagcacatc agcgaggtca ttacgcagga ctacacgcgc caccacccgc agcagctcag    6960
tggcccccctt cccgccccctc tctactcctt tcccggagcc agctgccctg tcctggatct    7020
tcgccgccca cccagtgacc tctacctccc accccccgac catggcaccc cagcccgggg    7080
atcccccccac agtgaagggg gcaaaaggtc cccagaaccc agcaaaacat cggtcctggg    7140
cagcagcgag gatgccattg agcctgtgtc cccaccagag ggcatgactg agccaggaca    7200
tgctcggagc actgcgtacc cactgctgta tcgagacggg gaacagggcg agcccaggat    7260
gggtctagag tctccaggca acaccagcca gccgccaacc ttcttcagta agctgactga    7320
gagcaactcc gccatggtga agtcgaagaa gcaggagatc aacaagaaac tcaacaccca    7380
caaccggaac gagccagaat acaatattgg ccagcctggg acggaaatct tcaacatgcc    7440
cgccatcact ggagcaggcc ttatgacctg tagaagccag gcggtgcaag aacacgccag    7500
caccaacatg gggctagagg ccattattag aaaggcactc atgggtaaat atgatcagtg    7560
```

-continued

```
ggaagagccc ccgccgctcg gcgccaatgc ttttaaccct ctgaatgcca gcgccagtct    7620
gcccgctgct gctatgccca taaccactgc tgacggacgg agtgaccacg cactcacctc    7680
gccaggtgga ggtgggaaag ccaaggtctc tggcagacct agcagccgaa aagccaagtc    7740
gccagcacca ggcctagcgt ccggagaccg acccccttct gtctcctcag tacactcaga    7800 ggggactgc aatcgccgaa caccactcac caaccgtgtg tgggaggacc ggccctcatc     7860 tgcaggtcc acgccattcc cctacaaccc tttgattatg aggctacagg caggtgtcat     7920 ggcctcccg cccccacctg gccttgcggc aggcagcggg ccctagctg gtccccacca      7980 cgcctgggat gaggagccca gccactgct gtgttcacag tatgagacac tctcggacag     8040
cgagtgacca cggattgggg gggagcggtg ccaggtcccg cacaaggcag aagcagccca    8100
gcatggagca gacagctgct gactcccgag actgaggaag gagcccctga gtctgcctgc    8160
gcgtccatcc gtncgtcgtn cactcatctg tccatccaga gctggcattc tgcctgtcta    8220
aagccttaac taagacttcc accccgggct ggccctgcgc agtgaccta cactcagggg     8280 attgtttacc ttggtgctcg anaaggggga gtggacagga aggggaggga caagccgggc    8340 cangagggggg gggacaanc aattcgtgtg tcaagtcgca ctcntgct                 8388
```

<210> SEQ ID NO 7
<211> LENGTH: 2473
<212> TYPE: PRT
<213> ORGANISM: Mus musculus

<400> SEQUENCE: 7

```
Met Ser Gly Ser Thr Gln Pro Val Ala Gln Thr Trp Arg Ala Ala Glu
 1               5                  10                  15

Pro Arg Tyr Pro Pro His Gly Ile Ser Tyr Pro Val Gln Ile Ala Arg
            20                  25                  30

Ser His Thr Asp Val Gly Leu Leu Glu Tyr Gln His His Pro Arg Asp
        35                  40                  45

Tyr Thr Ser His Leu Ser Pro Gly Ser Ile Ile Gln Pro Gln Arg Arg
    50                  55                  60

Arg Pro Ser Leu Leu Ser Glu Phe Gln Pro Gly Ser Glu Arg Ser Gln
65                  70                  75                  80

Glu Leu His Leu Arg Pro Glu Ser Arg Thr Phe Leu Pro Glu Leu Gly
                85                  90                  95

Lys Pro Asp Ile Glu Phe Thr Glu Ser Lys Arg Pro Arg Leu Glu Leu
            100                 105                 110

Leu Pro Asp Thr Leu Leu Arg Pro Ser Pro Leu Leu Ala Thr Gly Gln
        115                 120                 125

Pro Ser Gly Ser Glu Asp Leu Thr Lys Asp Arg Ser Leu Ala Gly Lys
    130                 135                 140

Leu Glu Pro Val Ser Pro Pro Ser Pro Pro His Ala Asp Pro Glu Leu
145                 150                 155                 160

Glu Leu Ala Pro Ser Arg Leu Ser Lys Glu Glu Leu Ile Gln Asn Met
                165                 170                 175

Asp Arg Val Asp Arg Glu Ile Thr Met Val Glu Gln Gln Ile Ser Lys
            180                 185                 190

Leu Lys Lys Lys Gln Gln Gln Leu Glu Glu Ala Ala Lys Pro Pro
        195                 200                 205

Glu Pro Glu Lys Pro Val Ser Pro Pro Ile Glu Ser Lys His Arg
    210                 215                 220

Ser Leu Val Gln Ile Ile Tyr Asp Glu Asn Arg Lys Lys Ala Glu Ala
```

```
                    225                 230                 235                 240
Ala His Arg Ile Leu Glu Gly Leu Gly Pro Gln Val Glu Leu Pro Leu
                245                 250                 255

Tyr Asn Gln Pro Ser Asp Thr Arg Gln Tyr His Glu Asn Ile Lys Ile
            260                 265                 270

Asn Gln Ala Met Arg Lys Lys Leu Ile Leu Tyr Phe Lys Arg Arg Asn
        275                 280                 285

His Ala Arg Lys Gln Trp Glu Gln Arg Phe Cys Gln Arg Tyr Asp Gln
    290                 295                 300

Leu Met Glu Ala Trp Glu Lys Lys Val Glu Arg Ile Glu Asn Asn Pro
305                 310                 315                 320

Arg Arg Arg Ala Lys Glu Ser Lys Val Arg Glu Tyr Tyr Glu Lys Gln
                325                 330                 335

Phe Pro Glu Ile Arg Lys Gln Arg Glu Leu Gln Glu Arg Met Gln Ser
            340                 345                 350

Arg Val Gly Gln Arg Gly Ser Gly Leu Ser Met Ser Ala Ala Arg Ser
        355                 360                 365

Glu His Glu Val Ser Glu Ile Ile Asp Gly Leu Ser Glu Gln Glu Asn
    370                 375                 380

Leu Glu Lys Gln Met Arg Gln Leu Ala Val Ile Pro Pro Met Leu Tyr
385                 390                 395                 400

Asp Ala Asp Gln Gln Arg Ile Lys Phe Ile Asn Met Asn Gly Leu Met
                405                 410                 415

Asp Asp Pro Met Lys Val Tyr Lys Asp Arg Gln Val Thr Asn Met Trp
            420                 425                 430

Ser Glu Gln Glu Arg Asp Thr Phe Arg Glu Lys Phe Met Gln His Pro
        435                 440                 445

Lys Asn Phe Gly Leu Ile Ala Ser Phe Leu Glu Arg Lys Thr Val Ala
    450                 455                 460

Glu Cys Val Leu Tyr Tyr Tyr Leu Thr Lys Lys Asn Glu Asn Tyr Lys
465                 470                 475                 480

Ser Leu Val Arg Arg Ser Tyr Arg Arg Arg Gly Lys Ser Gln Gln Gln
                485                 490                 495

Gln Gln Gln Gln Gln Gln Gln Gln Gln Gln Met Ala Arg Ser Ser
            500                 505                 510

Gln Glu Glu Lys Glu Glu Lys Glu Lys Glu Lys Glu Ala Asp Lys Glu
        515                 520                 525

Glu Glu Lys Gln Asp Ala Glu Asn Glu Lys Glu Glu Leu Ser Lys Glu
    530                 535                 540

Lys Thr Asp Asp Thr Ser Gly Glu Asp Asn His Glu Lys Glu Ala Val
545                 550                 555                 560

Ala Ser Lys Gly Arg Lys Thr Ala Asn Ser Gln Gly Arg Arg Lys Gly
                565                 570                 575

Arg Ile Thr Arg Ser Met Ala Asn Glu Ala Asn His Glu Glu Thr Ala
            580                 585                 590

Thr Pro Gln Gln Ser Ser Glu Leu Ala Ser Met Glu Met Asn Glu Ser
        595                 600                 605

Ser Arg Trp Thr Glu Glu Met Glu Thr Ala Lys Lys Gly Leu Leu
    610                 615                 620

Glu His Gly Arg Asn Trp Ser Ala Ile Ala Arg Met Val Gly Ser Lys
625                 630                 635                 640

Thr Val Ser Gln Cys Lys Asn Phe Tyr Phe Asn Tyr Lys Lys Arg Gln
                645                 650                 655
```

```
Asn Leu Asp Glu Ile Leu Gln Gln His Lys Leu Lys Met Glu Lys Glu
                660                 665                 670
Arg Asn Ala Arg Arg Lys Lys Lys Thr Pro Ala Ala Ala Ser Glu
        675                 680                 685
Glu Thr Ala Phe Pro Pro Ala Ala Glu Asp Glu Met Glu Ala Ser
        690                 695                 700
Gly Ala Ser Ala Asn Glu Glu Leu Ala Glu Ala Glu Ala Ser
705                 710                 715                 720
Gln Ala Ser Gly Asn Glu Val Pro Arg Val Gly Glu Cys Ser Gly Pro
                725                 730                 735
Ala Ala Val Asn Asn Ser Ser Asp Thr Glu Ser Val Pro Ser Pro Arg
                740                 745                 750
Ser Glu Ala Met Lys Asp Thr Gly Pro Lys Pro Thr Gly Thr Glu Ala
        755                 760                 765
Leu Pro Ala Ala Thr Gln Pro Pro Val Pro Pro Glu Glu Pro Ala
770                 775                 780
Val Ala Pro Ala Glu Pro Ser Pro Val Pro Asp Ala Ser Gly Pro Pro
785                 790                 795                 800
Ser Pro Glu Pro Ser His His Leu Pro His Pro Arg Leu Leu Trp Thr
                805                 810                 815
Arg Met Asn Lys Lys Pro Arg Leu Leu Gln Leu Pro Arg Gln Arg Met
        820                 825                 830
Pro Arg Ser Arg Ser Leu Arg Pro Arg Arg Ser Met Trp Glu Lys Pro
        835                 840                 845
Glu Glu Pro Glu Ala Ser Glu Glu Pro Pro Glu Ser Val Lys Ser Asp
        850                 855                 860
His Lys Glu Glu Thr Glu Glu Glu Pro Glu Asp Lys Ala Lys Gly Thr
865                 870                 875                 880
Glu Ala Ile Glu Thr Val Ser Glu Ala Pro Leu Lys Val Glu Glu Ala
                885                 890                 895
Gly Ser Lys Ala Ala Val Thr Lys Gly Ser Ser Ser Gly Ala Thr Gln
                900                 905                 910
Asp Ser Asp Phe Ser Ala Thr Cys Ser Ala Asp Glu Val Asp Glu Pro
        915                 920                 925
Glu Gly Gly Asp Lys Gly Arg Leu Leu Ser Pro Arg Pro Ser Leu Leu
        930                 935                 940
Thr Pro Ala Gly Asp Pro Arg Ala Ser Thr Ser Pro Gln Lys Pro Leu
945                 950                 955                 960
Asp Leu Lys Gln Leu Lys Gln Arg Ala Ala Ala Ile Pro Pro Ile Gln
                965                 970                 975
Val Thr Lys Val His Glu Pro Pro Arg Glu Asp Thr Val Pro Pro Lys
                980                 985                 990
Pro Val Pro Pro Val Pro Pro Pro Thr Gln His Leu Gln Pro Glu Gly
        995                 1000                1005
Asp Val Ser Gln Gln Ser Gly Gly Ser Pro Arg Gly Lys Ser Arg Ser
        1010                1015                1020
Pro Val Pro Pro Ala Glu Lys Glu Ala Glu Lys Pro Ala Phe Phe Pro
1025                1030                1035                1040
Ala Phe Pro Thr Glu Gly Pro Lys Leu Pro Thr Glu Pro Pro Arg Trp
                1045                1050                1055
Ser Ser Gly Leu Pro Phe Pro Ile Pro Pro Arg Glu Val Ile Lys Thr
        1060                1065                1070
```

```
Ser Pro His Ala Ala Asp Pro Ser Ala Phe Ser Tyr Thr Pro Pro Gly
    1075                1080                1085

His Pro Leu Pro Leu Gly Leu His Asp Ser Ala Arg Pro Val Leu Pro
    1090                1095                1100

Arg Pro Pro Ile Ser Asn Pro Pro Leu Ile Ser Ser Ala Lys His
1105                1110                1115                1120

Pro Gly Val Leu Glu Arg Gln Leu Gly Ala Ile Ser Gln Gln Gly Met
                1125                1130                1135

Ser Val Gln Leu Arg Val Pro His Ser Glu His Ala Lys Ala Pro Met
            1140                1145                1150

Gly Pro Leu Thr Met Gly Leu Pro Leu Ala Val Asp Pro Lys Lys Leu
        1155                1160                1165

Gly Thr Ala Leu Gly Ser Ala Thr Ser Gly Ser Ile Thr Lys Gly Leu
    1170                1175                1180

Pro Ser Thr Arg Ala Ala Asp Gly Pro Ser Tyr Arg Gly Ser Ile Thr
1185                1190                1195                1200

His Gly Thr Pro Ala Asp Val Leu Tyr Lys Gly Thr Ile Ser Arg Ile
                1205                1210                1215

Val Gly Glu Asp Ser Pro Ser Arg Leu Asp Arg Ala Arg Glu Asp Thr
            1220                1225                1230

Leu Pro Lys Gly His Val Ile Tyr Glu Gly Lys Lys Gly His Val Leu
        1235                1240                1245

Ser Tyr Glu Gly Gly Met Ser Val Ser Gln Cys Ser Lys Glu Asp Gly
    1250                1255                1260

Arg Ser Ser Gly Pro Pro His Glu Thr Ala Ala Pro Lys Arg Thr
1265                1270                1275                1280

Tyr Asp Met Met Glu Gly Arg Val Gly Arg Thr Val Thr Ser Ala Ser
                1285                1290                1295

Ile Glu Gly Leu Met Gly Arg Ala Ile Pro Glu Gln His Ser Pro His
            1300                1305                1310

Leu Lys Glu Gln His His Ile Arg Gly Ser Ile Thr Gln Gly Ile Pro
        1315                1320                1325

Arg Ser Tyr Val Glu Ala Gln Glu Asp Tyr Leu Arg Arg Glu Ala Lys
    1330                1335                1340

Leu Leu Lys Arg Glu Gly Thr Pro Pro Pro Pro Pro Pro Arg Asp
1345                1350                1355                1360

Leu Thr Glu Thr Tyr Lys Pro Arg Pro Leu Asp Pro Leu Gly Pro Leu
                1365                1370                1375

Lys Leu Lys Pro Thr His Glu Gly Val Val Ala Thr Val Lys Glu Ala
            1380                1385                1390

Gly Arg Ser Ile His Glu Ile Pro Arg Glu Glu Leu Arg Arg Thr Pro
        1395                1400                1405

Glu Leu Pro Leu Ala Pro Arg Pro Leu Lys Glu Gly Ser Ile Thr Gln
    1410                1415                1420

Gly Thr Pro Leu Lys Tyr Asp Ser Gly Ala Pro Ser Thr Gly Thr Lys
1425                1430                1435                1440

Lys His Asp Val Arg Ser Ile Ile Gly Ser Pro Gly Arg Pro Phe Pro
                1445                1450                1455

Ala Leu His Pro Leu Asp Ile Met Ala Asp Ala Arg Ala Leu Glu Arg
            1460                1465                1470

Ala Cys Tyr Glu Glu Ser Leu Lys Ser Arg Ser Gly Thr Ser Ser Gly
        1475                1480                1485

Ala Gly Gly Ser Ile Thr Arg Gly Ala Pro Val Val Val Pro Glu Leu
```

-continued

```
             1490                1495                1500
Gly Lys Pro Arg Gln Ser Pro Leu Thr Tyr Glu Asp His Gly Ala Pro
1505                1510                1515                1520

Phe Thr Ser His Leu Pro Arg Gly Ser Pro Val Thr Thr Arg Glu Pro
             1525                1530                1535

Thr Pro Arg Leu Gln Glu Gly Ser Leu Leu Ser Ser Lys Ala Ser Gln
             1540                1545                1550

Asp Arg Lys Leu Thr Ser Thr Pro Arg Glu Ile Ala Lys Ser Pro His
             1555                1560                1565

Ser Thr Val Pro Glu His His Pro His Pro Ile Ser Pro Tyr Glu His
             1570                1575                1580

Leu Leu Arg Gly Val Thr Gly Val Asp Leu Tyr Arg Gly His Ile Pro
1585                1590                1595                1600

Leu Ala Phe Asp Pro Thr Ser Ile Pro Arg Gly Ile Pro Leu Glu Ala
             1605                1610                1615

Ala Ala Ala Ala Tyr Tyr Leu Pro Arg His Leu Ala Pro Ser Pro Thr
             1620                1625                1630

Tyr Pro His Leu Tyr Pro Pro Tyr Leu Ile Arg Gly Tyr Pro Asp Thr
             1635                1640                1645

Ala Ala Leu Glu Asn Arg Gln Thr Ile Ile Asn Asp Tyr Ile Thr Ser
             1650                1655                1660

Gln Gln Met His His Asn Ala Ala Ser Ala Met Ala Gln Arg Ala Asp
1665                1670                1675                1680

Met Leu Arg Gly Leu Ser Pro Arg Glu Ser Ser Leu Ala Leu Asn Tyr
             1685                1690                1695

Ala Ala Gly Pro Arg Gly Ile Ile Asp Leu Ser Gln Val Pro His Leu
             1700                1705                1710

Pro Val Leu Val Pro Pro Thr Pro Gly Thr Pro Ala Thr Ala Ile Asp
             1715                1720                1725

Arg Leu Ala Tyr Leu Pro Thr Ala Pro Pro Phe Ser Ser Arg His
             1730                1735                1740

Ser Ser Ser Pro Leu Ser Pro Gly Gly Pro Thr His Leu Ala Lys Pro
1745                1750                1755                1760

Thr Ala Thr Ser Ser Ser Glu Arg Glu Arg Glu Arg Glu Arg
             1765                1770                1775

Asp Lys Ser Ile Leu Thr Ser Thr Thr Thr Val Glu His Ala Pro Ile
             1780                1785                1790

Trp Arg Pro Gly Thr Glu Gln Ser Ser Gly Ala Gly Gly Ser Ser Arg
             1795                1800                1805

Pro Ala Ser His Thr His Gln His Ser Pro Ile Ser Pro Arg Thr Gln
             1810                1815                1820

Asp Ala Leu Gln Gln Arg Pro Ser Val Leu His Asn Thr Ser Met Lys
1825                1830                1835                1840

Gly Val Val Thr Ser Val Glu Pro Gly Thr Pro Thr Val Leu Arg Trp
             1845                1850                1855

Ala Arg Ser Thr Ser Thr Ser Ser Pro Val Arg Pro Ala Ala Thr Phe
             1860                1865                1870

Pro Pro Ala Thr His Cys Pro Leu Gly Gly Thr Leu Glu Gly Val Tyr
             1875                1880                1885

Pro Thr Leu Met Glu Pro Val Leu Leu Pro Lys Glu Thr Ser Arg Val
             1890                1895                1900

Ala Arg Pro Glu Arg Ala Arg Val Asp Ala Gly His Ala Phe Leu Thr
1905                1910                1915                1920
```

```
Lys Pro Pro Gly Arg Glu Pro Ala Ser Ser Pro Ser Lys Ser Ser Glu
            1925                1930                1935

Pro Arg Ser Leu Ala Pro Pro Ser Ser His Thr Ala Ile Ala Arg
        1940                1945                1950

Thr Pro Ala Lys Asn Leu Ala Pro His His Ala Ser Pro Asp Pro Pro
        1955                1960                1965

Ala Pro Thr Ser Ala Ser Asp Leu His Arg Glu Lys Thr Gln Ser Lys
        1970                1975                1980

Pro Phe Ser Ile Gln Glu Leu Glu Leu Arg Ser Leu Gly Tyr His Ser
1985                1990                1995                2000

Gly Ala Gly Tyr Ser Pro Asp Gly Val Glu Pro Ile Ser Pro Val Ser
            2005                2010                2015

Ser Pro Ser Leu Thr His Asp Lys Gly Leu Ser Lys Pro Leu Glu Glu
            2020                2025                2030

Leu Glu Lys Ser His Leu Glu Gly Glu Leu Arg His Lys Gln Pro Gly
            2035                2040                2045

Pro Met Lys Leu Ser Ala Glu Ala Ala His Leu Pro His Leu Arg Pro
    2050                2055                2060

Leu Pro Glu Ser Gln Pro Ser Ser Ser Pro Leu Leu Gln Thr Ala Pro
2065                2070                2075                2080

Gly Ile Lys Gly His Gln Arg Val Val Thr Leu Ala Gln His Ile Ser
            2085                2090                2095

Glu Val Ile Thr Gln Asp Tyr Thr Arg His His Pro Gln Gln Leu Ser
            2100                2105                2110

Gly Pro Leu Pro Ala Pro Leu Tyr Ser Phe Pro Gly Ala Ser Cys Pro
            2115                2120                2125

Val Leu Asp Leu Arg Arg Pro Pro Ser Asp Leu Tyr Leu Pro Pro Pro
    2130                2135                2140

Asp His Gly Thr Pro Ala Arg Gly Ser Pro His Ser Glu Gly Gly Lys
2145                2150                2155                2160

Arg Ser Pro Glu Pro Ser Lys Thr Ser Val Leu Gly Ser Ser Glu Asp
            2165                2170                2175

Ala Ile Glu Pro Val Ser Pro Pro Glu Gly Met Thr Glu Pro Gly His
            2180                2185                2190

Ala Arg Ser Thr Ala Tyr Pro Leu Leu Tyr Arg Asp Gly Glu Gln Gly
            2195                2200                2205

Glu Pro Arg Met Gly Leu Glu Ser Pro Gly Asn Thr Ser Gln Pro Pro
    2210                2215                2220

Thr Phe Phe Ser Lys Leu Thr Glu Ser Asn Ser Ala Met Val Lys Ser
2225                2230                2235                2240

Lys Lys Gln Glu Ile Asn Lys Lys Leu Asn Thr His Asn Arg Asn Glu
            2245                2250                2255

Pro Glu Tyr Asn Ile Gly Gln Pro Gly Thr Glu Ile Phe Asn Met Pro
            2260                2265                2270

Ala Ile Thr Gly Ala Gly Leu Met Thr Cys Arg Ser Gln Ala Val Gln
        2275                2280                2285

Glu His Ala Ser Thr Asn Met Gly Leu Glu Ala Ile Ile Arg Lys Ala
    2290                2295                2300

Leu Met Gly Lys Tyr Asp Gln Trp Glu Glu Pro Pro Pro Leu Gly Ala
2305                2310                2315                2320

Asn Ala Phe Asn Pro Leu Asn Ala Ser Ala Ser Leu Pro Ala Ala Ala
            2325                2330                2335
```

-continued

```
Met Pro Ile Thr Thr Ala Asp Gly Arg Ser Asp His Ala Leu Thr Ser
        2340                2345                2350
Pro Gly Gly Gly Gly Lys Ala Lys Val Ser Gly Arg Pro Ser Ser Arg
            2355                2360                2365
Lys Ala Lys Ser Pro Ala Pro Gly Leu Ala Ser Gly Asp Arg Pro Pro
    2370                2375                2380
Ser Val Ser Ser Val His Ser Glu Gly Asp Cys Asn Arg Arg Thr Pro
2385                2390                2395                2400
Leu Thr Asn Arg Val Trp Glu Asp Arg Pro Ser Ser Ala Gly Ser Thr
                2405                2410                2415
Pro Phe Pro Tyr Asn Pro Leu Ile Met Arg Leu Gln Ala Gly Val Met
        2420                2425                2430
Ala Ser Pro Pro Pro Gly Leu Ala Ala Gly Ser Gly Pro Leu Ala
        2435                2440                2445
Gly Pro His His Ala Trp Asp Glu Glu Pro Lys Pro Leu Leu Cys Ser
    2450                2455                2460
Gln Tyr Glu Thr Leu Ser Asp Ser Glu
2465                2470
```

```
<210> SEQ ID NO 8
<211> LENGTH: 7465
<212> TYPE: DNA
<213> ORGANISM: Mus sp.
<220> FEATURE:
<221> NAME/KEY: modified_base
<222> LOCATION: (7250)
<223> OTHER INFORMATION: a, c, t, g, other or unknown
<220> FEATURE:
<221> NAME/KEY: modified_base
<222> LOCATION: (7257)
<223> OTHER INFORMATION: a, c, t, g, other or unknown
<220> FEATURE:
<221> NAME/KEY: modified_base
<222> LOCATION: (7379)
<223> OTHER INFORMATION: a, c, t, g, other or unknown
<220> FEATURE:
<221> NAME/KEY: modified_base
<222> LOCATION: (7420)
<223> OTHER INFORMATION: a, c, t, g, other or unknown
<220> FEATURE:
<221> NAME/KEY: modified_base
<222> LOCATION: (7436)
<223> OTHER INFORMATION: a, c, t, g, other or unknown
<220> FEATURE:
<221> NAME/KEY: modified_base
<222> LOCATION: (7461)
<223> OTHER INFORMATION: a, c, t, g, other or unknown

<400> SEQUENCE: 8
ggcacgaggg cagcgcaggc cgggccgcat ccccgtcccc gcgccagccg cccgcgcccg     60
ccatgcgcgc cccgcagcgg cccgcgcgtc cgggccccgc gtcgtagcgc ggcgggcgga    120
gaccgcaggc tctcagcccg gacccgccgc atcctcgagc ccgatcggcg ccgtagcccg    180
gcgccagcgc ccggtgccgc cgccggcgag tgctcctgag tctttgagga acacagcctc    240
ctggtggaag ttcgtggcac ctgtgacgag gtcacctgcc agcagatgac cgagaccagc    300
ccttagtcct aggtgtggtc aagagtgtct tgggctccaa agcctacctg gaccctacca    360
ccatgtcagg atccacacag cctgtggcac agacatggcg ggctgctgag ccccgctacc    420 cacccccatgg catctcctac ccggtgcaga tagcccggtc ccacacgcct ctgtacaacc    480
agccgtctga cacacgccag taccatgaaa acatcaaaat aaaccaggcg atgcggaaga    540
agctgatctt gtactttaag cggaggaacc acgcgcgcaa gcagtgggaa cagcgcttct    600
```

```
gccagcgcta tgaccagctc atggaggcgt gggagaagaa ggtagagcgc atagagaaca    660
atccgcgaag gagggccaag gagagcaagg tgagggagta ctacgagaaa cagttcccgg    720
agatccgcaa gcagcgggag ctgcaggagc gcatgcagag cagggtgggc cagcgtggca    780
gtgggctctc catgtcggct gcccgcagtg agcatgaggt ttctgagatc attgatggct    840
tgtctgagca ggagaacctg gagaagcaga tgcgccagct ggccgtgatc ccgcccatgt    900
tgtacgacgc ggaccagcag aggatcaagt tcatcaacat gaatggactc atggatgacc    960
ccatgaaggt ctacaaggac cgtcaggtta ccaacatgtg gagcgagcag gagagggaca   1020
ccttccgtga gaagtttatg cagcacccta gaactttggg cctgattgcc tcattcctgg   1080
agagaaagac ggtcgctgag tgtgtcctct attactacct gaccaagaag aatgaaaatt   1140
acaagagctt ggtgaggcgg agctatcggc gccgtggcaa gagccagcag cagcagcagc   1200
agcaacaaca gcagcagcag cagcagatgg cacggagcag ccaggaggag aaggaggaga   1260
aggagaagga gaaggaggcc gacaaggagg aagagaagca ggatgcggag aacgagaagg   1320
aagaactcag caaggagaag acagacgaca cttctggcga ggacaacgat gagaaagagg   1380
ccgtggcctc caaggccgc aaaactgcca acagccaagg ccgccgcaaa ggccgtatca   1440
cgcgctccat ggccaacgag gccaaccatg aggagacagc caccccacag caaagttcag   1500
agctggcttc catggagatg aacgagagtt ctcgctggac tgaggaagag atggagacag   1560
caaagaaagg cctcctggaa catgggagga actggtcagc cattgcccgc atggtgggct   1620
ccaagaccgt gtcccagtgt aagaacttct acttcaacta caagaagagg cagaacctgg   1680
acgaaatcct tcagcagcac aagctaaaga tggagaagga gaggaacgct cggaggaaga   1740
agaagaagac cccagctgcg gcgagcgagg agacagcctt cccacctgcc gctgaggacg   1800
aagagatgga agcatcaggc gcaagtgcca atgaggaaga gctggcggag gaggcagaag   1860
cctcacaggc ctctgggaat gaggttccca gagttgggga gtgcagtggc ccagctgctg   1920
tcaacaacag ctctgatact gagagtgtcc catccccgcg ttcagaagcc acgaaggaca   1980
ctgggcctaa acccactggc actgaagcat gcccgctgc cacccagcca cctgttcctc   2040
ctccagaaga accggcagta gcccctgctg agccctcccc agtccctgat gccagtggcc   2100
caccatcccc agagccttcc catcacctgc cgcacccccg gctactgtgg acaaggatga   2160
acaagaagcc ccggctgctc cagctccca gacagaggat gccaaggagc agaagtctga   2220
ggccgaggag atcgatgtgg aaaagccag aggagcccga ggcttctgag aagccccga    2280
agagtgtaaa gagtgaccac aagaaggaga ccgaggaaga gcctgaagac aaagccaagg   2340
gcacagaggc cattgaaact gtgtctgagg caccacttaa ggtggagaag gctggtagca   2400
aggcagctgt gaccaagggt tccagctcag gtgccaccca ggacagtgac tccagtgcca   2460
cctgcagtgc cgatgaggtg gacgaacccg aaggaggtga caagggcagg ctgctgtcac   2520
caaggcccag cctcctcacc ccggctggag atccccgggc cagtacctcg ccccagaagc   2580
cgctggacct gaagcagctg aagcagcgag cagccgccat ccccctatc gtcaccaagg   2640
tccatgagcc ccccgggag gacacagtac ccccaaagcc agttcccct gtgcctccac   2700
ccacgcagca cctacagcca gagggtgacg tgtctcagca gtcgggagga agtccacgtg   2760
gcaagtcccg cagcccagtg cctcctgccg agaaagaggc agagaaaccc gcattctttc   2820
cggcttttccc aactgagggc ccaaagctac cgactgagcc cccacgctgg tcatcgggcc   2880
tgcccttccc catccctcca cgggaggtga tcaagacttc cccacacgcc gctgacccct   2940
ctgccttctc ctacacaccc cccggtcacc cgctgcctct gggcctccac gatagtgccc   3000
```

-continued

```
ggcccgtcct gccacgtccc cccatctcta acccccacc cctcatctcc tctgccaagc    3060
atcccggcgt acttgagagg cagctggtg ccatctccca gcagggatg tcagtccagc    3120 ttcgtgtgcc tcactcagag catgccaagg ccccatggg ccctctcacc atggggctgc    3180
cccttgccgt ggaccctaag aagctgggga cagcactggg ctccgccacc agtggaagca    3240
tcaccaaggg cctccccagt acccgggctg cagacggccc cagctacaga ggctctatca    3300
cccacggcac gcccgcagac gtcctctaca agggtaccat cagcaggatc gtcggtgagg    3360
acagcccaag tcgccttgac cgggcacgag aggacaccct gcccaagggc catgtcatct    3420
atgagggcaa gaaaggccac gtcctatcct atgaaggtgg tatgtccgtg tcacagtgct    3480
ctaaggagga tggaaggagc agctcgggcc cacccatga gactgccgcc ctaaacgca    3540 cctatgacat gatggagggc cgtgtaggca ggactgtcac ctcagccagc atagagggac    3600
tcatgggccg cgccatccct gagcagcaca gccccacct caaggagcag catcacatcc    3660
gaggctccat cacgcaaggc atcccgaggt cctatgtgga ggcgcaggag gactacttac    3720
ggcgggaggc caagtcttg aagcgagaag gacaccacc accccacca ccacctcggg    3780 acctgactga gacctacaag ccccggcccc tggaccctct gggtcccctg aagctgaagc    3840
cgactcacga gggtgtggta gcaactgtga aggaggcggg ccgctctatc catgagatcc    3900
cgagagagga gctgcgccgc acacctgagc taccctggc accacggcct ctgaaggagg    3960
gttccatcac ccagggcacc ccactcaagt acgactctgg ggcacctcc actggcacca    4020 agaaacgca cgtgcgctcc atcatcggca gccccgccg gcctttccct gccctgcacc    4080
cgctggacat aatggctgac gcccgggcac tggagcgtgc ctgctatgaa gagagtctga    4140
agagccggtc agggaccagc agtggtgcag ggggctccat cacacgtggg gctccagtcg    4200
tcgtgcctga actgggcaag ccacggcaaa gcccactgac ttacgaagac cacggggcac    4260
ccttcaccag tcacctgcca cgtggctccc ctgtgaccac gagggagccc acgccacgcc    4320
ttcaggaagg cagcctccta tccagcaagg cgtcccagga ccggaagctg acatctacac    4380
cccgggagat cgccaagtcc ccacacagca ctgtgcccga gcaccaccct caccccatct    4440 cccctatga gcacttgctc cggggcgtga ctggtgtgga cctgtaccgt ggtcacatcc    4500
cattggcctt tgaccccacc tccatacccc gagggatccc tctggaagca gcagccgcag    4560
cctactacct gccccggcac ttggccccca gccccaccta cccacacctg tacccacctt    4620
acctcatccg cggctaccct gacacggcgg ccctggagaa ccgccagacc atcatcaatg    4680
actacatcac ctcgcagcag atgcaccaca cgctgcctc cgccatggcc cagcgtgctg    4740
acatgctgag gggtctgtca ccgcgagagt cctcgctggc cctcaattat gccgctggcc    4800
caagaggcat tatcgacctg tcccaagtgc cacacctgcc cgtgctggtg ccaccaacgc    4860
caggcacccc tgccaccgcc atcgaccgcc ttgcctacct ccccactgcg cccccaccct    4920
tcagcagccg ccacagtagc tcaccgctgt ccccaggagg ccccactcac ctagctaaac    4980
caactgccac atcttcatcg gagcgggaac gggaacgtga gcgggaacga gacaagtcca    5040
tcctcacgtc taccactaca gtggagcatg cacccatctg gagacctggt acggagcaga    5100
gcagcggggc tggggcagc agccgccccg cctcccacac ccaccagcac tcgcccatct    5160
cccccgggac ccaggacgcc ttgcagcaga ggcccagtgt gctgcacaac acgagcatga    5220
agggcgtggt cacctccgtg gaacccggca cgccacggt cctgaggtgg gccaggtcca    5280
cctccacctc ttcgcctgtc cgcccagctg ccacattccc acctgccacc cactgcccac    5340
```

```
ttggtggcac ccttgaaggg gtctacccta ccctcatgga gcccgtcctg ttacccaagg    5400
agacctctcg ggtcgcccgg cccgagcggg cccggtggac gctggccat gcctttctta    5460
ccaaaccccc gggccgggag cccgcctcct cacccagcaa gagctccgag ccccgatccc    5520
tagcacccc cagctccagc cacacagcca tcgcccgcac cccagcaaag aaccttgcac    5580
cccaccatgc cagtccggac ccgccggcgc ccacctcggc ctcagatctg caccgagaaa    5640
agactcaaag taaacccttt tccatccagg aattggaact ccgttctctg ggttaccaca    5700
gtggagctgg ctacagcccc gatggggtgg agcccatcag cccggtgagc tcccccagcc    5760
tgacccacga caagggggctc tccaaacctc tggaagagct agagaagagc cacttggaag    5820
gggagctgcg gcacaagcag ccaggcccca tgaagctcag cgcggaggct gcccatctcc    5880
cacatctgcg gccactgccc gagagccagc cctcatccag cccactcctc cagactgccc    5940
caggcatcaa aggtcaccag agggtggtca ccctggctca gcacatcagc gaggtcatta    6000
cgcaggacta cacgcgccac cacccgcagc agctcagtgg ccccctttccc gcccctctct    6060
actcctttcc cggagccagc tgccctgtcc tggatcttcg ccgcccaccc agtgacctct    6120
acctcccacc ccccgaccat ggcacccag cccggggatc cccccacagt gaaggggca    6180
aaaggtcccc agaacccagc aaaacatcgg tcctgggcag cagcgaggat gccattgagc    6240
ctgtgtcccc accagagggc atgactgagc caggacatgc tcggagcact gcgtaccac    6300
tgctgtatcg agacggggaa cagggcgagc ccaggatggg tctagagtct ccaggcaaca    6360
ccagccagcc gccaaccttc ttcagtaagc tgactgagag caactccgcc atggtgaagt    6420
cgaagaagca ggagatcaac aagaaactca acacccacaa ccggaacgag ccagaataca    6480
atattggcca gcctgggacg gaaatcttca acatgcccgc catcactgga gcaggcctta    6540
tgacctgtag aagccaggcg gtgcaagaac acgccagcac caacatgggg ctagaggcca    6600
ttattagaaa ggcactcatg ggtaaatatg atcagtggga agagccccg ccgctcggcg    6660
ccaatgcttt taaccctctg aatgccagcg ccagtctgcc cgctgctgct atgcccataa    6720
ccactgctga cggacggagt gaccacgcac tcacctcgcc aggtggaggt gggaaagcca    6780
aggtctctgg cagacctagc agccgaaaag ccaagtcgcc agcaccaggc ctagcgtccg    6840
gagaccgacc cccttctgtc tcctcagtac actcagaggg ggactgcaat cgccgaacac    6900
cactcaccaa ccgtgtgtgg gaggaccggc cctcatctgc agggtccacg ccattcccct    6960
acaacccttt gattatgagg ctacaggcag gtgtcatggc ctccccgccc ccacctggcc    7020
ttgcggcagg cagcgggccc ctagctggtc cccaccacgc ctgggatgag gagcccaagc    7080
cactgctgtg ttcacagtat gagacactct cggacagcga gtgaccacgg attgggggg    7140
agcggtgcca ggtcccgcac aaggcagaag cagcccagca tggagcagac agctgctgac    7200
tcccgagact gaggaaggag cccctgagtc tgcctgcgcg tccatccgtn cgtcgtncac    7260
tcatctgtcc atccagagct ggcattctgc ctgtctaaag ccttaactaa gacttccacc    7320
ccgggctggc cctgcgcagt gaccttacac tcagggatt gtttaccttg gtgctcgana    7380
aggggagtg gacaggaagg ggagggacaa gccgggccan gaggggggg gacaancaat    7440
tcgtgtgtca agtcgcactc ntgct                                         7465

<210> SEQ ID NO 9
<211> LENGTH: 2253
<212> TYPE: PRT
<213> ORGANISM: Mus sp.

<400> SEQUENCE: 9
```

```
Met Ser Gly Ser Thr Gln Pro Val Ala Gln Thr Trp Arg Ala Glu
 1               5                  10                  15

Pro Arg Tyr Pro Pro His Gly Ile Ser Tyr Pro Val Gln Ile Ala Arg
            20                  25                  30

Ser His Thr Pro Leu Tyr Asn Gln Pro Ser Asp Thr Arg Gln Tyr His
            35                  40                  45

Glu Asn Ile Lys Ile Asn Gln Ala Met Arg Lys Leu Ile Leu Tyr
 50                  55                  60

Phe Lys Arg Arg Asn His Ala Arg Lys Gln Trp Glu Gln Arg Phe Cys
 65                  70                  75                  80

Gln Arg Tyr Asp Gln Leu Met Glu Ala Trp Glu Lys Lys Val Glu Arg
                85                  90                  95

Ile Glu Asn Asn Pro Arg Arg Ala Lys Glu Ser Lys Val Arg Glu
            100                 105                 110

Tyr Tyr Glu Lys Gln Phe Pro Glu Ile Arg Lys Gln Arg Glu Leu Gln
            115                 120                 125

Glu Arg Met Gln Ser Arg Val Gly Gln Arg Gly Ser Gly Leu Ser Met
130                 135                 140

Ser Ala Ala Arg Ser Glu His Glu Val Ser Glu Ile Ile Asp Gly Leu
145                 150                 155                 160

Ser Glu Gln Glu Asn Leu Glu Lys Gln Met Arg Gln Leu Ala Val Ile
                165                 170                 175

Pro Pro Met Leu Tyr Asp Ala Asp Gln Gln Arg Ile Lys Phe Ile Asn
            180                 185                 190

Met Asn Gly Leu Met Asp Asp Pro Met Lys Val Tyr Lys Asp Arg Gln
            195                 200                 205

Val Thr Asn Met Trp Ser Glu Gln Glu Arg Asp Thr Phe Arg Glu Lys
            210                 215                 220

Phe Met Gln His Pro Lys Asn Phe Gly Leu Ile Ala Ser Phe Leu Glu
225                 230                 235                 240

Arg Lys Thr Val Ala Glu Cys Val Leu Tyr Tyr Tyr Leu Thr Lys Lys
                245                 250                 255

Asn Glu Asn Tyr Lys Ser Leu Val Arg Arg Ser Tyr Arg Arg Arg Gly
            260                 265                 270

Lys Ser Gln Gln Gln Gln Gln Gln Gln Gln Gln Gln Gln Gln Gln
            275                 280                 285

Met Ala Arg Ser Ser Gln Glu Glu Lys Glu Glu Lys Glu Lys Glu Lys
290                 295                 300

Glu Ala Asp Lys Glu Glu Glu Lys Gln Asp Ala Glu Asn Glu Lys Glu
305                 310                 315                 320

Glu Leu Ser Lys Glu Lys Thr Asp Asp Thr Ser Gly Glu Asp Asn Asp
                325                 330                 335

Glu Lys Glu Ala Val Ala Ser Lys Gly Arg Lys Thr Ala Asn Ser Gln
            340                 345                 350

Gly Arg Arg Lys Gly Arg Ile Thr Arg Ser Met Ala Asn Glu Ala Asn
            355                 360                 365

His Glu Glu Thr Ala Thr Pro Gln Gln Ser Ser Glu Leu Ala Ser Met
            370                 375                 380

Glu Met Asn Glu Ser Ser Arg Trp Thr Glu Glu Met Glu Thr Ala
385                 390                 395                 400

Lys Lys Gly Leu Leu Glu His Gly Arg Asn Trp Ser Ala Ile Ala Arg
                405                 410                 415
```

-continued

```
Met Val Gly Ser Lys Thr Val Ser Gln Cys Lys Asn Phe Tyr Phe Asn
            420                 425                 430

Tyr Lys Lys Arg Gln Asn Leu Asp Glu Ile Leu Gln Gln His Lys Leu
        435                 440                 445

Lys Met Glu Lys Glu Arg Asn Ala Arg Lys Lys Lys Thr Pro
    450                 455                 460

Ala Ala Ala Ser Glu Glu Thr Ala Phe Pro Ala Ala Glu Asp Glu
465                 470                 475                 480

Glu Met Glu Ala Ser Gly Ala Ser Ala Asn Glu Glu Leu Ala Glu
            485                 490                 495

Glu Ala Glu Ala Ser Gln Ala Ser Gly Asn Glu Val Pro Arg Val Gly
                500                 505                 510

Glu Cys Ser Gly Pro Ala Ala Val Asn Asn Ser Ser Asp Thr Glu Ser
            515                 520                 525

Val Pro Ser Pro Arg Ser Glu Ala Thr Lys Asp Thr Gly Lys Pro
    530                 535                 540

Thr Gly Thr Glu Ala Leu Pro Ala Ala Thr Gln Pro Pro Val Pro Pro
545                 550                 555                 560

Pro Glu Glu Pro Ala Val Ala Pro Ala Glu Pro Ser Pro Val Pro Asp
                565                 570                 575

Ala Ser Gly Pro Pro Ser Pro Glu Pro Ser His His Leu Pro His Pro
            580                 585                 590

Arg Leu Leu Trp Thr Arg Met Asn Lys Lys Pro Arg Leu Leu Gln Leu
            595                 600                 605

Pro Arg Gln Arg Met Pro Arg Ser Arg Ser Leu Arg Pro Arg Arg Ser
    610                 615                 620

Met Trp Glu Lys Pro Glu Glu Pro Glu Ala Ser Glu Lys Pro Pro Lys
625                 630                 635                 640

Ser Val Lys Ser Asp His Lys Lys Glu Thr Glu Glu Pro Glu Asp
                645                 650                 655

Lys Ala Lys Gly Thr Glu Ala Ile Glu Thr Val Ser Glu Ala Pro Leu
            660                 665                 670

Lys Val Glu Lys Ala Gly Ser Lys Ala Ala Val Thr Lys Gly Ser Ser
            675                 680                 685

Ser Gly Ala Thr Gln Asp Ser Asp Ser Ser Ala Thr Cys Ser Ala Asp
            690                 695                 700

Glu Val Asp Glu Pro Glu Gly Gly Asp Lys Gly Arg Leu Leu Ser Pro
705                 710                 715                 720

Arg Pro Ser Leu Leu Thr Pro Ala Gly Asp Pro Arg Ala Ser Thr Ser
                725                 730                 735

Pro Gln Lys Pro Leu Asp Leu Lys Gln Leu Lys Gln Arg Ala Ala Ala
            740                 745                 750

Ile Pro Pro Ile Val Thr Lys Val His Glu Pro Pro Arg Glu Asp Thr
            755                 760                 765

Val Pro Pro Lys Pro Val Pro Val Pro Pro Thr Gln His Leu
    770                 775                 780

Gln Pro Glu Gly Asp Val Ser Gln Gln Ser Gly Ser Pro Arg Gly
785                 790                 795                 800

Lys Ser Arg Ser Pro Val Pro Ala Glu Lys Glu Ala Glu Lys Pro
                805                 810                 815

Ala Phe Phe Pro Ala Phe Pro Thr Glu Gly Pro Lys Leu Pro Thr Glu
            820                 825                 830

Pro Pro Arg Trp Ser Ser Gly Leu Pro Phe Pro Ile Pro Pro Arg Glu
```

```
                    835                 840                 845
Val Ile Lys Thr Ser Pro His Ala Ala Asp Pro Ser Ala Phe Ser Tyr
850                 855                 860

Thr Pro Pro Gly His Pro Leu Pro Leu Gly Leu His Asp Ser Ala Arg
865                 870                 875                 880

Pro Val Leu Pro Arg Pro Pro Ile Ser Asn Pro Pro Leu Ile Ser
                885                 890                 895

Ser Ala Lys His Pro Gly Val Leu Glu Arg Gln Leu Gly Ala Ile Ser
                900                 905                 910

Gln Gln Gly Met Ser Val Gln Leu Arg Val Pro His Ser Glu His Ala
                915                 920                 925

Lys Ala Pro Met Gly Pro Leu Thr Met Gly Leu Pro Leu Ala Val Asp
930                 935                 940

Pro Lys Lys Leu Gly Thr Ala Leu Gly Ser Ala Thr Ser Gly Ser Ile
945                 950                 955                 960

Thr Lys Gly Leu Pro Ser Thr Arg Ala Ala Asp Gly Pro Ser Tyr Arg
                965                 970                 975

Gly Ser Ile Thr His Gly Thr Pro Ala Asp Val Leu Tyr Lys Gly Thr
                980                 985                 990

Ile Ser Arg Ile Val Gly Glu Asp Ser Pro Ser Arg Leu Asp Arg Ala
                995                 1000                1005

Arg Glu Asp Thr Leu Pro Lys Gly His Val Ile Tyr Glu Gly Lys Lys
1010                1015                1020

Gly His Val Leu Ser Tyr Glu Gly Gly Met Ser Val Ser Gln Cys Ser
1025                1030                1035                1040

Lys Glu Asp Gly Arg Ser Ser Ser Gly Pro Pro His Glu Thr Ala Ala
                1045                1050                1055

Pro Lys Arg Thr Tyr Asp Met Met Glu Gly Arg Val Gly Arg Thr Val
                1060                1065                1070

Thr Ser Ala Ser Ile Glu Gly Leu Met Gly Arg Ala Ile Pro Glu Gln
                1075                1080                1085

His Ser Pro His Leu Lys Glu Gln His His Ile Arg Gly Ser Ile Thr
                1090                1095                1100

Gln Gly Ile Pro Arg Ser Tyr Val Glu Ala Gln Glu Asp Tyr Leu Arg
1105                1110                1115                1120

Arg Glu Ala Lys Leu Leu Lys Arg Glu Gly Thr Pro Pro Pro Pro
                1125                1130                1135

Pro Pro Arg Asp Leu Thr Glu Thr Tyr Lys Pro Arg Pro Leu Asp Pro
                1140                1145                1150

Leu Gly Pro Leu Lys Leu Lys Pro Thr His Glu Gly Val Val Ala Thr
                1155                1160                1165

Val Lys Glu Ala Gly Arg Ser Ile His Glu Ile Pro Arg Glu Glu Leu
1170                1175                1180

Arg Arg Thr Pro Glu Leu Pro Leu Ala Pro Arg Pro Leu Lys Glu Gly
1185                1190                1195                1200

Ser Ile Thr Gln Gly Thr Pro Leu Lys Tyr Asp Ser Gly Ala Pro Ser
                1205                1210                1215

Thr Gly Thr Lys Lys His Asp Val Arg Ser Ile Ile Gly Ser Pro Gly
                1220                1225                1230

Arg Pro Phe Pro Ala Leu His Pro Leu Asp Ile Met Ala Asp Ala Arg
                1235                1240                1245

Ala Leu Glu Arg Ala Cys Tyr Glu Glu Ser Leu Lys Ser Arg Ser Gly
                1250                1255                1260
```

-continued

```
Thr Ser Ser Gly Ala Gly Gly Ser Ile Thr Arg Gly Ala Pro Val Val
1265                1270                1275                1280

Val Pro Glu Leu Gly Lys Pro Arg Gln Ser Pro Leu Thr Tyr Glu Asp
            1285                1290                1295

His Gly Ala Pro Phe Thr Ser His Leu Pro Arg Gly Ser Pro Val Thr
            1300                1305                1310

Thr Arg Glu Pro Thr Pro Arg Leu Gln Glu Gly Ser Leu Leu Ser Ser
            1315                1320                1325

Lys Ala Ser Gln Asp Arg Lys Leu Thr Ser Thr Pro Arg Glu Ile Ala
    1330                1335                1340

Lys Ser Pro His Ser Thr Val Pro Glu His His Pro His Pro Ile Ser
1345                1350                1355                1360

Pro Tyr Glu His Leu Leu Arg Gly Val Thr Gly Val Asp Leu Tyr Arg
            1365                1370                1375

Gly His Ile Pro Leu Ala Phe Asp Pro Thr Ser Ile Pro Arg Gly Ile
            1380                1385                1390

Pro Leu Glu Ala Ala Ala Ala Ala Tyr Tyr Leu Pro Arg His Leu Ala
            1395                1400                1405

Pro Ser Pro Thr Tyr Pro His Leu Tyr Pro Pro Tyr Leu Ile Arg Gly
    1410                1415                1420

Tyr Pro Asp Thr Ala Ala Leu Glu Asn Arg Gln Thr Ile Ile Asn Asp
1425                1430                1435                1440

Tyr Ile Thr Ser Gln Gln Met His His Asn Ala Ala Ser Ala Met Ala
            1445                1450                1455

Gln Arg Ala Asp Met Leu Arg Gly Leu Ser Pro Arg Glu Ser Ser Leu
            1460                1465                1470

Ala Leu Asn Tyr Ala Ala Gly Pro Arg Gly Ile Ile Asp Leu Ser Gln
            1475                1480                1485

Val Pro His Leu Pro Val Leu Val Pro Pro Thr Pro Gly Thr Pro Ala
    1490                1495                1500

Thr Ala Ile Asp Arg Leu Ala Tyr Leu Pro Thr Ala Pro Pro Pro Phe
1505                1510                1515                1520

Ser Ser Arg His Ser Ser Ser Pro Leu Ser Pro Gly Gly Pro Thr His
            1525                1530                1535

Leu Ala Lys Pro Thr Ala Thr Ser Ser Ser Glu Arg Glu Arg Glu Arg
            1540                1545                1550

Glu Arg Glu Arg Asp Lys Ser Ile Leu Thr Ser Thr Thr Thr Val Glu
            1555                1560                1565

His Ala Pro Ile Trp Arg Pro Gly Thr Glu Gln Ser Ser Gly Ala Gly
            1570                1575                1580

Gly Ser Ser Arg Pro Ala Ser His Thr His Gln His Ser Pro Ile Ser
1585                1590                1595                1600

Pro Arg Thr Gln Asp Ala Leu Gln Gln Arg Pro Ser Val Leu His Asn
            1605                1610                1615

Thr Ser Met Lys Gly Val Val Thr Ser Val Glu Pro Gly Thr Pro Thr
            1620                1625                1630

Val Leu Arg Trp Ala Arg Ser Thr Ser Thr Ser Ser Pro Val Arg Pro
            1635                1640                1645

Ala Ala Thr Phe Pro Pro Ala Thr His Cys Pro Leu Gly Gly Thr Leu
    1650                1655                1660

Glu Gly Val Tyr Pro Thr Leu Met Glu Pro Val Leu Leu Pro Lys Glu
1665                1670                1675                1680
```

-continued

Thr Ser Arg Val Ala Arg Pro Glu Arg Ala Arg Val Asp Gly His
        1685                1690                1695

Ala Phe Leu Thr Lys Pro Pro Gly Arg Glu Pro Ala Ser Ser Pro Ser
        1700                1705                1710

Lys Ser Ser Glu Pro Arg Ser Leu Ala Pro Pro Ser Ser His Thr
        1715                1720                1725

Ala Ile Ala Arg Thr Pro Ala Lys Asn Leu Ala Pro His His Ala Ser
        1730                1735                1740

Pro Asp Pro Pro Ala Pro Thr Ser Ala Ser Asp Leu His Arg Glu Lys
1745                1750                1755                1760

Thr Gln Ser Lys Pro Phe Ser Ile Gln Glu Leu Glu Leu Arg Ser Leu
        1765                1770                1775

Gly Tyr His Ser Gly Ala Gly Tyr Ser Pro Asp Gly Val Glu Pro Ile
        1780                1785                1790

Ser Pro Val Ser Ser Pro Ser Leu Thr His Asp Lys Gly Leu Ser Lys
        1795                1800                1805

Pro Leu Glu Glu Leu Glu Lys Ser His Leu Glu Gly Glu Leu Arg His
        1810                1815                1820

Lys Gln Pro Gly Pro Met Lys Leu Ser Ala Glu Ala Ala His Leu Pro
1825                1830                1835                1840

His Leu Arg Pro Leu Pro Glu Ser Gln Pro Ser Ser Ser Pro Leu Leu
        1845                1850                1855

Gln Thr Ala Pro Gly Ile Lys Gly His Gln Arg Val Val Thr Leu Ala
        1860                1865                1870

Gln His Ile Ser Glu Val Ile Thr Gln Asp Tyr Thr Arg His His Pro
        1875                1880                1885

Gln Gln Leu Ser Gly Pro Leu Pro Ala Pro Leu Tyr Ser Phe Pro Gly
        1890                1895                1900

Ala Ser Cys Pro Val Leu Asp Leu Arg Arg Pro Pro Ser Asp Leu Tyr
1905                1910                1915                1920

Leu Pro Pro Pro Asp His Gly Thr Pro Ala Arg Gly Ser Pro His Ser
        1925                1930                1935

Glu Gly Gly Lys Arg Ser Pro Glu Pro Ser Lys Thr Ser Val Leu Gly
        1940                1945                1950

Ser Ser Glu Asp Ala Ile Glu Pro Val Ser Pro Pro Glu Gly Met Thr
        1955                1960                1965

Glu Pro Gly His Ala Arg Ser Thr Ala Tyr Pro Leu Leu Tyr Arg Asp
        1970                1975                1980

Gly Glu Gln Gly Glu Pro Arg Met Gly Leu Glu Ser Pro Gly Asn Thr
1985                1990                1995                2000

Ser Gln Pro Pro Thr Phe Phe Ser Lys Leu Thr Glu Ser Asn Ser Ala
        2005                2010                2015

Met Val Lys Ser Lys Lys Gln Glu Ile Asn Lys Lys Leu Asn Thr His
        2020                2025                2030

Asn Arg Asn Glu Pro Glu Tyr Asn Ile Gly Gln Pro Gly Thr Glu Ile
        2035                2040                2045

Phe Asn Met Pro Ala Ile Thr Gly Ala Gly Leu Met Thr Cys Arg Ser
2050                2055                2060

Gln Ala Val Gln Glu His Ala Ser Thr Asn Met Gly Leu Glu Ala Ile
2065                2070                2075                2080

Ile Arg Lys Ala Leu Met Gly Lys Tyr Asp Gln Trp Glu Glu Pro Pro
        2085                2090                2095

Pro Leu Gly Ala Asn Ala Phe Asn Pro Leu Asn Ala Ser Ala Ser Leu

```
                       2100               2105               2110
Pro Ala Ala Met Pro Ile Thr Thr Ala Asp Gly Arg Ser Asp His
    2115               2120               2125
Ala Leu Thr Ser Pro Gly Gly Gly Lys Ala Lys Val Ser Gly Arg
    2130               2135               2140
Pro Ser Ser Arg Lys Ala Lys Ser Pro Ala Pro Gly Leu Ala Ser Gly
2145               2150               2155               2160
Asp Arg Pro Pro Ser Val Ser Ser Val His Ser Glu Gly Asp Cys Asn
                2165               2170               2175
Arg Arg Thr Pro Leu Thr Asn Arg Val Trp Glu Asp Arg Pro Ser Ser
            2180               2185               2190
Ala Gly Ser Thr Pro Phe Pro Tyr Asn Pro Leu Ile Met Arg Leu Gln
    2195               2200               2205
Ala Gly Val Met Ala Ser Pro Pro Pro Gly Leu Ala Ala Gly Ser
    2210               2215               2220
Gly Pro Leu Ala Gly Pro His His Ala Trp Asp Glu Pro Lys Pro
2225               2230               2235               2240
Leu Leu Cys Ser Gln Tyr Glu Thr Leu Ser Asp Ser Glu
            2245               2250

<210> SEQ ID NO 10
<211> LENGTH: 7940
<212> TYPE: DNA
<213> ORGANISM: Homo sapiens

<400> SEQUENCE: 10
ccaagatggc ggccaaggtg gcgaagcagc agccgcggcg gcggcggcgg ctggagtgag      60
cgtccgactc gccgcgccga acgaggtccc ggtgtagggc cgcgcgccgt ggccgcgtcc     120
cactcctcag gccggggcgc acgtcggctc ccacgcttag ccagctcccg gtggtttcct     180
agaaacatga ttgtttattg gcattgatct cacagtctgg tgaggacttc tttactgata     240
atgtcaagtt caggttatcc tcccaaccaa ggagcattca gcacagaaca agtcgttat      300 cctcctcact ctgtccagta tacatttccc aacacccgcc accagcagga gttcgcagtc     360
cctgattatc gttcctctca tcttgaagtg agtcaggcat cacagctttt gcagcaacag     420
cagcagcaac agcttcgaag gcgaccttcc ttgctttcag aatttcaccc aggttctgac     480
aggcctcaag aaaggagaac tagttatgaa ccgtttcatc caggcccatc cccagtggat     540
catgattcac tggaatcgaa gcgaccacgt ctggaacagg tttctgattc tcattttcag     600
cgtgtcagtg ctgcggtttt gcctttagtg cacccgctgc agaagggct gagggcttct      660 gcagatgcta agaaggatcc agcattcgga ggcaaacatg aagctccatc ctctccaatt     720
tcggggcaac catgtggaga tgatcaaaat gcttcacctt caaaactctc aaaggaagag     780
ttaatacaga gtatggatcg tgtagatcga gaaattgcaa agtagaaca gcagatcctt       840 aaactgaaaa agaaacaaca acagcttgaa gaagaggcag ctaaacctcc tgagcctgag     900
aagcccgtgt cccctcctcc tgtggagcag aaacaccgca gtattgtcca aattattttat    960 gatgagaatc ggaaaaaagc agaagaagct cataaaattt ttgaaggtct tggcccaaaa    1020
gttgaactgc cactgtataa ccagccatca gataccaagg tgtaccatga aacatcaag    1080 acaaaccagg tgatgaggaa aaaactcatt ttatttttta aagaagaaa tcatgcaaga     1140 aaacaaaggg aacaaaaaat ctgccagcgt tatgatcagc tcatggaggc atggagaaa     1200 aaagtggaca gaatagaaaa taatcctcgg aggaaagcta agaaaagcaa aacaagggaa    1260
```

-continued

```
tactatgaaa agcagtttcc agaaattcga aaacaaagag aacagcaaga aagatttcag      1320
cgagttgggc agaggggagc tggtctttca gccaccattg ctaggagtga gcatgagatt      1380
tctgaaatta ttgatgggct ctctgagcag gagaataatg agaaacaaat gcggcagctc      1440
tctgtgattc cacctatgat gtttgatgca gaacaaagac gagtcaagtt cattaacatg      1500
aatgggctta tggaggaccc tatgaaagtg tataaagata ggcagtttat gaatgtttgg      1560
actgaccatg aaaaggagat ctttaaggac aagtttatcc agcatccaaa aactttgga      1620 ctaattgcat catacttgga gaggaagagt gttcctgatt gtgttttgta ttactattta      1680
accaagaaaa atgagaatta taagccctc gtcagaagga attatgggaa acgcagaggc      1740
agaaaccagc aaattgctcg accctcgcaa gaagaaaaag tagaagaaaa agaagaggat      1800
aaagcagaaa aaacagaaaa aaagaagaa gaaagaaag atgaagagga aaagatgaa       1860 aaagaagact ccaaagaaaa taccaaggaa aaggacaaga tagatggtac agcagaagaa      1920
actgaggaaa gagagcaagc cacaccccgg gggcgaaaga ctgccaacag tcagggccgc      1980
cgtaagggcc ggatcaccag gtccatgaca aacgaagctg cagctgccag tgctgcagcc      2040
gcagcggcta ctgaagagcc cccaccacct ctgccaccgc caccgaaacc catttctaca      2100
gagcctgtgg agacctctcg atggacagaa gaagaaatgg aagttgctaa aaaaggtcta      2160
gtagaacatg tcgtaactg gcagcaatt gctaaaatgg tgggaacgaa aagtgaagct      2220
caatgtaaaa acttctattt taactataaa aggcgacaca atcttgacaa cctcttacag      2280
cagcataaac agaaaacttc acgaaaacct cgtgaagagc gagatgtgtc tcaatgtgaa      2340
agtgtcgctt ccactgtttc tgctcaggag gatgaagata ttgaagcctc caatgaagaa      2400
gaaaatccag aagacagcga agttgaagct gtcaagccca gcgaggacag tcctgaaaat      2460
gctacttctc gaggaaacac agaacctgcg gttgagcttg agcccaccac ggaaactgca      2520
cccagtacat ctccctcctt agcagttcca gtacaaaac cagctgaaga tgaaagtgtg      2580
gagacccagg tgaatgacag catcagtgct gagacagcag agcagatgga tgtagatcag      2640
caggagcaca gtgctgaaga gggttctgtt tgtgatcccc cacccgctac caaagctgac      2700
tctgtggacg ttgaagtgag ggtgccagaa aaccatgcat ctaaagttga aggtgataat      2760
accaaagaaa gagacttgga tagagccagt gagaaggtgg aacctagaga tgaagatttg      2820
gtggtagctc agcaaataaa tgcccaaagg cccgagcccc agtcagacaa tgattccagt      2880
gccacgtgca gcgctgatga ggatgtggat ggagagccag agaggcagag aatgtttcct      2940
atggactcaa agccttcact gttaaacccc actggatcta tactcgtctc atctccgtta      3000
aaaccaaatc cactggatct gccacagctt cagcatcgag ctgctgttat cccaccaatg      3060
gtatcctgca ccccatgtaa cataccaatt ggaaccccga tgagcggcta tgctctctac      3120
cagcgacaca ttaaagcaat gcatgagtca gcactcctgg aggagcagcg gcagagacaa      3180
gaacagatag atttggaatg tagaagttct acaagtccat gtggcacatc caagagtcca      3240
aacagagagt gggaagtcct tcagcctgct ccacatcaat tgataactaa tctccctgaa      3300
ggcgttcggc ttccgacaac tcgaccaacc aggccaccgc ccctctcat cccgtcatcc      3360 aaaccacag tggcttcaga aaaccatct tttataatgg gaggctccat ctcacaggga      3420
acaccaggca cttatttgac ttctcataat caggcttcct acactcaaga aacacccaag      3480
ccgtcagtag gatctatctc tcttggactg ccacggcaac aggaatctgc caaatcagct      3540
actttgccct acatcaagca ggaagaattt tctccccgaa gccaaaactc acaacctgag      3600
ggtctgttgg tcagggccca acatgaaggt gtagtcagag gtaccgcagg agccatacaa      3660
```

```
gaaggaagta taactcgggg aactccaacc agcaaaattt cagtggagag cattccatcc    3720
ctacggggct ctatcactca gggcaccccg gctctgcccc agactggcat accaacagag    3780
gctttggtga aggggtccat ttcgagaatg cccattgaag acagcagtcc tgagaaaggc    3840
agagaggaag ctgcatccaa aggccatgtt atttatgaag gcaaaagtgg acatatcttg    3900
tcatatgata atattaagaa tgcccgagaa gggactagga gtccaagaac agctcatgaa    3960
atcagtttaa agagaagcta tgaatcagtg gaaggaaata taaagcaagg gatgtcaatg    4020
agggagtctc ctgtatcagc accgttagag gggctgatat gccgagcatt acccaggggg    4080
agtcctcatt ctgacctcaa agaaaggact gtattgtctg gctccataat gcagggcaca    4140
ccaagagcaa caactgaaag ctttgaagat ggccttaaat atcccaaaca aattaaaagg    4200
gaaagtcctc ccatacgagc atttgaaggt gccattacca aaggaaaacc atatgatggc    4260
atcaccacca tcaaagaaat ggggcgttcc attcatgaga ttccaaggca agatatttta    4320
actcaggaaa gtcggaaaac tccagaagtg gtccagagca cacggccgat aattgagggt    4380
tccatttccc aggcacacc aataaagttt gacaacaact caggtcaatc tgccatcaaa    4440
cacaatgtca aatccttaat cacggggcct agcaaactat cccgtggaat gcctccgctg    4500
gaaattgtgc cagagaacat aaaagtggta gaacggggaa atatgaggga tgtgaaagca    4560
ggcgagaccg tgcgttcccg gcacacgtca gtggtaagct ctggcccctc cgttcttagg    4620
tccacactgc atgaagctcc caaagcacaa ctgagccctg ggatttatga tgacaccagt    4680
gcacggagga cccctgtgag ttatcaaaac accatgtcca gaggctcacc catgatgaac    4740
agaacttctg atgttacaat tcctcctaac aagtctacca atcatgaaag gaaatcgaca    4800 ctgacccta cccagaggga aagtatccca gcgaagtctc cagtgcctgg ggtggaccct    4860
gtcgtgagcc acagtccgtt tgatccccat cacagaggca gcactgcagg cgaggtttat    4920
tggagccacc tgcccacgca attggatcca gccatgcctt tcacagggc tttggatcct    4980 gcagcggctg cttacctgtt tcagagacag cttcaccaa ctccaggtta cccaagtcag    5040
tatcagcttt acgcaatgga gaacacaaga cagacaatct aaatgatta cattacctca    5100 caacagatgc aagtgaactt gcgtccagat gtggccagag gactctcccc aagagagcag    5160
ccactgggtc tccataccc agcaacgaga ggaatcattg acctgaccaa tatgcctcca    5220 acaatttag tgcctcatcc aggggaaca agcactcctc ccatggacag aatcacttat    5280
attcctggta cacagattac tttccctccc aggccgtaca actctgcttc catgtctcca    5340
ggacacccaa cacaccttgc agctgctgca agtgctgaga gggaacggga acgggagcgg    5400
gagaaggagc gggagcggga acggattgct gcagcttcct ccgacctcta cctgcggcca    5460
ggctcagaac agcctggccg acctggcagt catggatatg ttcgctcccc ttccccttca    5520
gtaagaactc aggagaccat gttgcaacag agacccagtg ttttccaagg aaccaatgga    5580
accagtgtaa tcacaccttt ggatccaact gctcagctac gaatcatgcc actgcctgct    5640
gggggccctt caataagcca aggcctgcca gcctcccgtt acaacactgc tgcggatgcc    5700
ctggctgctc ttgtggatgc tgcagcttct gcaccccaga tggatgtgtc caaaacaaaa    5760
gagagtaagc atgaagctgc caggttagaa gaaaatttga gaagcaggtc agcagcagtt    5820
agtgaacagc agcagctaga gcagaaaacc ctggaggtgg agaagagatc tgttcagtgt    5880
ttatacactt cttcagcctt tccaagtggc aagcccagc ctcattcttc agtagtttat    5940
tctgaggctg ggaaagataa agggcctcct ccaaaatcca gatatgagga agagctaagg    6000
```

```
accagaggga agactaccat tactgcagct aacttcatag acgtgatcat cacccggcaa      6060
attgcctcgg acaaggatgc gagggaacgt ggctctcaaa gttcagactc ttctagtagc      6120
ttatcttctc acaggtatga aacacctagc gatgctattg aggtgataag tcctgccagc      6180
tcacctgcgc caccccagga gaaactgcag acctatcagc cagaggttgt taaggcaaat      6240
caagcggaaa atgatcctac cagacaatat gaaggaccat tacatcacta tcgaccacag      6300
caggaatcac catctcccca acaacagctg ccccttctt cacaggcaga gggaatgggg       6360
caagtgccca ggacccatcg gctgatcaca cttgctgatc acatctgtca aattatcaca      6420
caagattttg ctagaaatca agtttcctcg cagactcccc agcagcctcc tacttctaca      6480
ttccagaact caccttctgc tttggtatct cacctgtga ggactaaaac atcaaaccgt       6540
tacagcccag aatcccaggc tcagtctgtc catcatcaaa gaccaggttc aagggtctct      6600
ccagaaaatc ttgtggacaa atccaggga agtaggcctg gaaaatcccc agagaggagt      6660
cacgtctctt ccgagcccta cgagcccatc tccccacccc aggttccggt tgtgcatgag      6720
aaacaggaca gcttgctgct cttgtctcag aggggcgcag agcctgcaga gcagaggaat      6780
gatgcccgct caccagggag tataagctac ttgccttcat tcttcaccaa gcttgaaaat      6840
acatcaccca tggttaaatc aaagaagcag gagattttc gtaagttgaa ctcctctggt       6900
ggaggtgact ctgatatggc agctgctcag ccaggaactg agatctttaa tctgccagca      6960
gttactacgt caggctcagt tagctctaga ggccattctt ttgctgatcc tgccagtaat      7020
cttgggctgg aagacattat caggaaggct ctcatgggaa gctttgatga caaagttgag      7080
gatcatggag ttgtcatgtc ccagcctatg ggagtagtgc ctggtactgc caacacctca      7140
gttgtgacca gtggtgagac acgaagagag aaggggacc catcacctca ttcaggagga      7200
gtttgcaaac caaagctgat cagcaagtca aacagcagga atctaagtc tcctatacct       7260 gggcaaggct acttaggaac ggaacggccc tcttcagtct cctctgtaca ttcagaaggg      7320
gattaccata ggcagacgcc agggtgggcc tgggaagaca ggccctcttc aacaggctca      7380
actcagtttc cttataaccc tctgactatg cggatgctca gcagtactcc accaacaccg      7440
attgcatgtg ctccctctgc ggtgaaccaa gcagctcctc accaacagaa caggatctgg      7500
gagcgagagc ctgccccact gctctcagca cagtacgaga ccctgtcgga tagtgatgac      7560
tgaactgcac aaagtgaggg gaacagggtg caggagaggg atctctagtt tttgtggttt      7620 aattttagt agcaggtcaa aaacctgccc tcctgtgact tattccctga gactttcag       7680 gagagccagc ccacagatga tgaagaaatg atggaagttc atttggagag tcaaatggga     7740
aaaaaacaaa caaaaaactg cctttgatac aggcaattca gtggactata ataatagtgg      7800
agggttgaga tgtagagttt ttaaaaagtg aacagttgct gttcttacat ctgtaaagaa      7860
aaccataatg tctttaaatc actcttctgt aaatagatga ccttttttgca gtgtaaaaaa      7920 aaaaaaaaaa aaaaaaaaa                                                 7940

<210> SEQ ID NO 11
<211> LENGTH: 2440
<212> TYPE: PRT
<213> ORGANISM: Homo sapiens

<400> SEQUENCE: 11

Met Ser Ser Ser Gly Tyr Pro Pro Asn Gln Gly Ala Phe Ser Thr Glu
1               5                   10                  15

Gln Ser Arg Tyr Pro Pro His Ser Val Gln Tyr Thr Phe Pro Asn Thr
            20                  25                  30
```

```
Arg His Gln Gln Glu Phe Ala Val Pro Asp Tyr Arg Ser Ser His Leu
            35                  40                  45

Glu Val Ser Gln Ala Ser Gln Leu Leu Gln Gln Gln Gln Gln Gln Gln
 50                  55                  60

Leu Arg Arg Arg Pro Ser Leu Leu Ser Glu Phe His Pro Gly Ser Asp
 65                  70                  75                  80

Arg Pro Gln Glu Arg Arg Thr Ser Tyr Glu Pro Phe His Pro Gly Pro
                 85                  90                  95

Ser Pro Val Asp His Asp Ser Leu Glu Ser Lys Arg Pro Arg Leu Glu
                100                 105                 110

Gln Val Ser Asp Ser His Phe Gln Arg Val Ser Ala Val Leu Pro
                115                 120                 125

Leu Val His Pro Leu Pro Glu Gly Leu Arg Ala Ser Ala Asp Ala Lys
            130                 135                 140

Lys Asp Pro Ala Phe Gly Gly Lys His Glu Ala Pro Ser Ser Pro Ile
145                 150                 155                 160

Ser Gly Gln Pro Cys Gly Asp Asp Gln Asn Ala Ser Pro Ser Lys Leu
                165                 170                 175

Ser Lys Glu Glu Leu Ile Gln Ser Met Asp Arg Val Asp Arg Glu Ile
                180                 185                 190

Ala Lys Val Glu Gln Gln Ile Leu Lys Leu Lys Lys Lys Gln Gln Gln
            195                 200                 205

Leu Glu Glu Glu Ala Ala Lys Pro Pro Glu Pro Glu Lys Pro Val Ser
        210                 215                 220

Pro Pro Pro Val Glu Gln Lys His Arg Ser Ile Val Gln Ile Ile Tyr
225                 230                 235                 240

Asp Glu Asn Arg Lys Lys Ala Glu Glu Ala His Lys Ile Phe Glu Gly
                245                 250                 255

Leu Gly Pro Lys Val Glu Leu Pro Leu Tyr Asn Gln Pro Ser Asp Thr
                260                 265                 270

Lys Val Tyr His Glu Asn Ile Lys Thr Asn Gln Val Met Arg Lys Lys
            275                 280                 285

Leu Ile Leu Phe Phe Lys Arg Arg Asn His Ala Arg Lys Gln Arg Glu
        290                 295                 300

Gln Lys Ile Cys Gln Arg Tyr Asp Gln Leu Met Glu Ala Trp Glu Lys
305                 310                 315                 320

Lys Val Asp Arg Ile Glu Asn Asn Pro Arg Arg Lys Ala Lys Glu Ser
                325                 330                 335

Lys Thr Arg Glu Tyr Tyr Glu Lys Gln Phe Pro Glu Ile Arg Lys Gln
                340                 345                 350

Arg Glu Gln Gln Glu Arg Phe Gln Arg Val Gly Gln Arg Gly Ala Gly
            355                 360                 365

Leu Ser Ala Thr Ile Ala Arg Ser Glu His Glu Ile Ser Glu Ile Ile
        370                 375                 380

Asp Gly Leu Ser Glu Gln Glu Asn Asn Glu Lys Gln Met Arg Gln Leu
385                 390                 395                 400

Ser Val Ile Pro Pro Met Met Phe Asp Ala Glu Gln Arg Arg Val Lys
                405                 410                 415

Phe Ile Asn Met Asn Gly Leu Met Glu Asp Pro Met Lys Val Tyr Lys
            420                 425                 430

Asp Arg Gln Phe Met Asn Val Trp Thr Asp His Glu Lys Glu Ile Phe
        435                 440                 445
```

-continued

Lys Asp Lys Phe Ile Gln His Pro Lys Asn Phe Gly Leu Ile Ala Ser
450                 455                 460

Tyr Leu Glu Arg Lys Ser Val Pro Asp Cys Val Leu Tyr Tyr Tyr Leu
465                 470                 475                 480

Thr Lys Lys Asn Glu Asn Tyr Lys Ala Leu Val Arg Arg Asn Tyr Gly
            485                 490                 495

Lys Arg Arg Gly Arg Asn Gln Gln Ile Ala Arg Pro Ser Gln Glu Glu
            500                 505                 510

Lys Val Glu Glu Lys Glu Glu Asp Lys Ala Glu Lys Thr Glu Lys Lys
        515                 520                 525

Glu Glu Glu Lys Lys Asp Glu Glu Lys Asp Lys Glu Asp Ser
530                 535                 540

Lys Glu Asn Thr Lys Glu Lys Asp Lys Ile Asp Gly Thr Ala Glu Glu
545                 550                 555                 560

Thr Glu Glu Arg Glu Gln Ala Thr Pro Arg Gly Arg Lys Thr Ala Asn
            565                 570                 575

Ser Gln Gly Arg Arg Lys Gly Arg Ile Thr Arg Ser Met Thr Asn Glu
            580                 585                 590

Ala Ala Ala Ala Ser Ala Ala Ala Ala Ala Thr Glu Glu Pro Pro
            595                 600                 605

Pro Pro Leu Pro Pro Pro Pro Glu Pro Ile Ser Thr Glu Pro Val Glu
    610                 615                 620

Thr Ser Arg Trp Thr Glu Glu Met Glu Val Ala Lys Lys Gly Leu
625                 630                 635                 640

Val Glu His Gly Arg Asn Trp Ala Ala Ile Ala Lys Met Val Gly Thr
            645                 650                 655

Lys Ser Glu Ala Gln Cys Lys Asn Phe Tyr Phe Asn Tyr Lys Arg Arg
            660                 665                 670

His Asn Leu Asp Asn Leu Leu Gln Gln His Lys Gln Lys Thr Ser Arg
            675                 680                 685

Lys Pro Arg Glu Glu Arg Asp Val Ser Gln Cys Glu Ser Val Ala Ser
    690                 695                 700

Thr Val Ser Ala Gln Glu Asp Glu Asp Ile Glu Ala Ser Asn Glu Glu
705                 710                 715                 720

Glu Asn Pro Glu Asp Ser Glu Val Glu Ala Val Lys Pro Ser Glu Asp
            725                 730                 735

Ser Pro Glu Asn Ala Thr Ser Arg Gly Asn Thr Glu Pro Ala Val Glu
            740                 745                 750

Leu Glu Pro Thr Thr Glu Thr Ala Pro Ser Thr Ser Pro Ser Leu Ala
        755                 760                 765

Val Pro Ser Thr Lys Pro Ala Glu Asp Glu Ser Val Glu Thr Gln Val
    770                 775                 780

Asn Asp Ser Ile Ser Ala Glu Thr Ala Glu Gln Met Asp Val Asp Gln
785                 790                 795                 800

Gln Glu His Ser Ala Glu Gly Ser Val Cys Asp Pro Pro Ala
            805                 810                 815

Thr Lys Ala Asp Ser Val Asp Val Glu Val Arg Val Pro Glu Asn His
            820                 825                 830

Ala Ser Lys Val Glu Gly Asp Asn Thr Lys Glu Arg Asp Leu Asp Arg
        835                 840                 845

Ala Ser Glu Lys Val Glu Pro Arg Asp Glu Asp Leu Val Val Ala Gln
        850                 855                 860

Gln Ile Asn Ala Gln Arg Pro Glu Pro Gln Ser Asp Asn Asp Ser Ser

-continued

```
            865                 870                 875                 880
        Ala Thr Cys Ser Ala Asp Glu Asp Val Asp Gly Glu Pro Glu Arg Gln
                            885                 890                 895

Arg Met Phe Pro Met Asp Ser Lys Pro Ser Leu Leu Asn Pro Thr Gly
                        900                 905                 910

Ser Ile Leu Val Ser Ser Pro Leu Lys Pro Asn Pro Leu Asp Leu Pro
                        915                 920                 925

Gln Leu Gln His Arg Ala Ala Val Ile Pro Pro Met Val Ser Cys Thr
                    930                 935                 940

Pro Cys Asn Ile Pro Ile Gly Thr Pro Val Ser Gly Tyr Ala Leu Tyr
        945                 950                 955                 960

Gln Arg His Ile Lys Ala Met His Glu Ser Ala Leu Leu Glu Glu Gln
                            965                 970                 975

Arg Gln Arg Gln Glu Gln Ile Asp Leu Glu Cys Arg Ser Ser Thr Ser
                        980                 985                 990

Pro Cys Gly Thr Ser Lys Ser Pro Asn Arg Glu Trp Glu Val Leu Gln
                        995                 1000                1005

Pro Ala Pro His Gln Leu Ile Thr Asn Leu Pro Glu Gly Val Arg Leu
        1010                1015                1020

Pro Thr Thr Arg Pro Thr Arg Pro Pro Pro Leu Ile Pro Ser Ser
        1025                1030                1035                1040

Lys Thr Thr Val Ala Ser Glu Lys Pro Ser Phe Ile Met Gly Gly Ser
                        1045                1050                1055

Ile Ser Gln Gly Thr Pro Gly Thr Tyr Leu Thr Ser His Asn Gln Ala
                    1060                1065                1070

Ser Tyr Thr Gln Glu Thr Pro Lys Pro Ser Val Gly Ser Ile Ser Leu
                1075                1080                1085

Gly Leu Pro Arg Gln Gln Glu Ser Ala Lys Ser Ala Thr Leu Pro Tyr
        1090                1095                1100

Ile Lys Gln Glu Glu Phe Ser Pro Arg Ser Gln Asn Ser Gln Pro Glu
        1105                1110                1115                1120

Gly Leu Leu Val Arg Ala Gln His Glu Gly Val Val Arg Gly Thr Ala
                        1125                1130                1135

Gly Ala Ile Gln Glu Gly Ser Ile Thr Arg Gly Thr Pro Thr Ser Lys
                    1140                1145                1150

Ile Ser Val Glu Ser Ile Pro Ser Leu Arg Gly Ser Ile Thr Gln Gly
            1155                1160                1165

Thr Pro Ala Leu Pro Gln Thr Gly Ile Pro Thr Glu Ala Leu Val Lys
        1170                1175                1180

Gly Ser Ile Ser Arg Met Pro Ile Glu Asp Ser Ser Pro Glu Lys Gly
        1185                1190                1195                1200

Arg Glu Glu Ala Ala Ser Lys Gly His Val Ile Tyr Glu Gly Lys Ser
                        1205                1210                1215

Gly His Ile Leu Ser Tyr Asp Asn Ile Lys Asn Ala Arg Glu Gly Thr
                    1220                1225                1230

Arg Ser Pro Arg Thr Ala His Glu Ile Ser Leu Lys Arg Ser Tyr Glu
                1235                1240                1245

Ser Val Glu Gly Asn Ile Lys Gln Gly Met Ser Met Arg Glu Ser Pro
        1250                1255                1260

Val Ser Ala Pro Leu Glu Gly Leu Ile Cys Arg Ala Leu Pro Arg Gly
        1265                1270                1275                1280

Ser Pro His Ser Asp Leu Lys Glu Arg Thr Val Leu Ser Gly Ser Ile
                    1285                1290                1295
```

-continued

```
Met Gln Gly Thr Pro Arg Ala Thr Thr Glu Ser Phe Glu Asp Gly Leu
            1300                1305                1310

Lys Tyr Pro Lys Gln Ile Lys Arg Glu Ser Pro Pro Ile Arg Ala Phe
        1315                1320                1325

Glu Gly Ala Ile Thr Lys Gly Lys Pro Tyr Asp Gly Ile Thr Thr Ile
    1330                1335                1340

Lys Glu Met Gly Arg Ser Ile His Glu Ile Pro Arg Gln Asp Ile Leu
1345                1350                1355                1360

Thr Gln Glu Ser Arg Lys Thr Pro Glu Val Val Gln Ser Thr Arg Pro
                1365                1370                1375

Ile Ile Glu Gly Ser Ile Ser Gln Gly Thr Pro Ile Lys Phe Asp Asn
            1380                1385                1390

Asn Ser Gly Gln Ser Ala Ile Lys His Asn Val Lys Ser Leu Ile Thr
        1395                1400                1405

Gly Pro Ser Lys Leu Ser Arg Gly Met Pro Pro Leu Glu Ile Val Pro
    1410                1415                1420

Glu Asn Ile Lys Val Val Glu Arg Gly Lys Tyr Glu Asp Val Lys Ala
1425                1430                1435                1440

Gly Glu Thr Val Arg Ser Arg His Thr Ser Val Val Ser Ser Gly Pro
                1445                1450                1455

Ser Val Leu Arg Ser Thr Leu His Glu Ala Pro Lys Ala Gln Leu Ser
            1460                1465                1470

Pro Gly Ile Tyr Asp Asp Thr Ser Ala Arg Arg Thr Pro Val Ser Tyr
        1475                1480                1485

Gln Asn Thr Met Ser Arg Gly Ser Pro Met Met Asn Arg Thr Ser Asp
    1490                1495                1500

Val Thr Ile Pro Pro Asn Lys Ser Thr Asn His Glu Arg Lys Ser Thr
1505                1510                1515                1520

Leu Thr Pro Thr Gln Arg Glu Ser Ile Pro Ala Lys Ser Pro Val Pro
                1525                1530                1535

Gly Val Asp Pro Val Val Ser His Ser Pro Phe Asp Pro His His Arg
            1540                1545                1550

Gly Ser Thr Ala Gly Glu Val Tyr Trp Ser His Leu Pro Thr Gln Leu
        1555                1560                1565

Asp Pro Ala Met Pro Phe His Arg Ala Leu Asp Pro Ala Ala Ala Ala
    1570                1575                1580

Tyr Leu Phe Gln Arg Gln Leu Ser Pro Thr Pro Gly Tyr Pro Ser Gln
1585                1590                1595                1600

Tyr Gln Leu Tyr Ala Met Glu Asn Thr Arg Gln Thr Ile Leu Asn Asp
                1605                1610                1615

Tyr Ile Thr Ser Gln Gln Met Gln Val Asn Leu Arg Pro Asp Val Ala
            1620                1625                1630

Arg Gly Leu Ser Pro Arg Glu Gln Pro Leu Gly Leu Pro Tyr Pro Ala
        1635                1640                1645

Thr Arg Gly Ile Ile Asp Leu Thr Asn Met Pro Pro Thr Ile Leu Val
    1650                1655                1660

Pro His Pro Gly Gly Thr Ser Thr Pro Pro Met Asp Arg Ile Thr Tyr
1665                1670                1675                1680

Ile Pro Gly Thr Gln Ile Thr Phe Pro Pro Arg Pro Tyr Asn Ser Ala
                1685                1690                1695

Ser Met Ser Pro Gly His Pro Thr His Leu Ala Ala Ala Ala Ser Ala
            1700                1705                1710
```

```
Glu Arg Glu Arg Glu Arg Glu Arg Glu Lys Glu Arg Glu Arg Glu Arg
        1715                1720                1725

Ile Ala Ala Ala Ser Ser Asp Leu Tyr Leu Arg Pro Gly Ser Glu Gln
    1730                1735                1740

Pro Gly Arg Pro Gly Ser His Gly Tyr Val Arg Ser Pro Ser Pro Ser
1745                1750                1755                1760

Val Arg Thr Gln Glu Thr Met Leu Gln Gln Arg Pro Ser Val Phe Gln
            1765                1770                1775

Gly Thr Asn Gly Thr Ser Val Ile Thr Pro Leu Asp Pro Thr Ala Gln
        1780                1785                1790

Leu Arg Ile Met Pro Leu Pro Ala Gly Gly Pro Ser Ile Ser Gln Gly
    1795                1800                1805

Leu Pro Ala Ser Arg Tyr Asn Thr Ala Ala Asp Ala Leu Ala Ala Leu
    1810                1815                1820

Val Asp Ala Ala Ala Ser Ala Pro Gln Met Asp Val Ser Lys Thr Lys
1825                1830                1835                1840

Glu Ser Lys His Glu Ala Ala Arg Leu Glu Glu Asn Leu Arg Ser Arg
            1845                1850                1855

Ser Ala Ala Val Ser Glu Gln Gln Gln Leu Glu Gln Lys Thr Leu Glu
        1860                1865                1870

Val Glu Lys Arg Ser Val Gln Cys Leu Tyr Thr Ser Ala Phe Pro
    1875                1880                1885

Ser Gly Lys Pro Gln Pro His Ser Ser Val Val Tyr Ser Glu Ala Gly
        1890                1895                1900

Lys Asp Lys Gly Pro Pro Pro Lys Ser Arg Tyr Glu Glu Glu Leu Arg
1905                1910                1915                1920

Thr Arg Gly Lys Thr Thr Ile Thr Ala Ala Asn Phe Ile Asp Val Ile
            1925                1930                1935

Ile Thr Arg Gln Ile Ala Ser Asp Lys Asp Ala Arg Glu Arg Gly Ser
        1940                1945                1950

Gln Ser Ser Asp Ser Ser Ser Ser Leu Ser Ser His Arg Tyr Glu Thr
        1955                1960                1965

Pro Ser Asp Ala Ile Glu Val Ile Ser Pro Ala Ser Ser Pro Ala Pro
    1970                1975                1980

Pro Gln Glu Lys Leu Gln Thr Tyr Gln Pro Glu Val Val Lys Ala Asn
1985                1990                1995                2000

Gln Ala Glu Asn Asp Pro Thr Arg Gln Tyr Glu Gly Pro Leu His His
            2005                2010                2015

Tyr Arg Pro Gln Gln Glu Ser Pro Ser Pro Gln Gln Gln Leu Pro Pro
        2020                2025                2030

Ser Ser Gln Ala Glu Gly Met Gly Gln Val Pro Arg Thr His Arg Leu
        2035                2040                2045

Ile Thr Leu Ala Asp His Ile Cys Gln Ile Ile Thr Gln Asp Phe Ala
    2050                2055                2060

Arg Asn Gln Val Ser Ser Gln Thr Pro Gln Gln Pro Pro Thr Ser Thr
2065                2070                2075                2080

Phe Gln Asn Ser Pro Ser Ala Leu Val Ser Thr Pro Val Arg Thr Lys
            2085                2090                2095

Thr Ser Asn Arg Tyr Ser Pro Glu Ser Gln Ala Gln Ser Val His His
        2100                2105                2110

Gln Arg Pro Gly Ser Arg Val Ser Pro Glu Asn Leu Val Asp Lys Ser
    2115                2120                2125

Arg Gly Ser Arg Pro Gly Lys Ser Pro Glu Arg Ser His Val Ser Ser
```

-continued

```
              2130                2135                2140
Glu Pro Tyr Glu Pro Ile Ser Pro Pro Gln Val Pro Val Val His Glu
2145                2150                2155                2160

Lys Gln Asp Ser Leu Leu Leu Ser Gln Arg Gly Ala Glu Pro Ala
            2165                2170                2175

Glu Gln Arg Asn Asp Ala Arg Ser Pro Gly Ser Ile Ser Tyr Leu Pro
            2180                2185                2190

Ser Phe Phe Thr Lys Leu Glu Asn Thr Ser Pro Met Val Lys Ser Lys
            2195                2200                2205

Lys Gln Glu Ile Phe Arg Lys Leu Asn Ser Ser Gly Gly Gly Asp Ser
            2210                2215                2220

Asp Met Ala Ala Ala Gln Pro Gly Thr Glu Ile Phe Asn Leu Pro Ala
2225                2230                2235                2240

Val Thr Thr Ser Gly Ser Val Ser Ser Arg Gly His Ser Phe Ala Asp
            2245                2250                2255

Pro Ala Ser Asn Leu Gly Leu Glu Asp Ile Ile Arg Lys Ala Leu Met
            2260                2265                2270

Gly Ser Phe Asp Asp Lys Val Glu Asp His Gly Val Val Met Ser Gln
            2275                2280                2285

Pro Met Gly Val Val Pro Gly Thr Ala Asn Thr Ser Val Val Thr Ser
            2290                2295                2300

Gly Glu Thr Arg Arg Glu Gly Asp Pro Ser Pro His Ser Gly Gly
2305                2310                2315                2320

Val Cys Lys Pro Lys Leu Ile Ser Lys Ser Asn Ser Arg Lys Ser Lys
            2325                2330                2335

Ser Pro Ile Pro Gly Gln Gly Tyr Leu Gly Thr Glu Arg Pro Ser Ser
            2340                2345                2350

Val Ser Ser Val His Ser Glu Gly Asp Tyr His Arg Gln Thr Pro Gly
            2355                2360                2365

Trp Ala Trp Glu Asp Arg Pro Ser Ser Thr Gly Ser Thr Gln Phe Pro
            2370                2375                2380

Tyr Asn Pro Leu Thr Met Arg Met Leu Ser Ser Thr Pro Pro Thr Pro
2385                2390                2395                2400

Ile Ala Cys Ala Pro Ser Ala Val Asn Gln Ala Ala Pro His Gln Gln
            2405                2410                2415

Asn Arg Ile Trp Glu Arg Glu Pro Ala Pro Leu Leu Ser Ala Gln Tyr
            2420                2425                2430

Glu Thr Leu Ser Asp Ser Asp Asp
            2435                2440

<210> SEQ ID NO 12
<211> LENGTH: 3446
<212> TYPE: PRT
<213> ORGANISM: Drosophila sp.

<400> SEQUENCE: 12

Met Ser Ala Tyr Gln Gln Arg Leu Pro Ser Asn Ala Ala Ser Ile His
1               5                   10                  15

Ser Pro His Trp Ser Tyr Arg Ala Leu Glu Gln Gln Gln Gln Tyr Ala
            20                  25                  30

Lys Gln Ala Ala His Leu Gln Gln Gln His Gln Ser His Gln Gln
        35                  40                  45

Gln Gln Gln Gln Gln Asp Gln Arg Thr Asn Leu His Leu Gln Ile
    50                  55                  60
```

```
His His His His Gln Gln Gln Gln Gln Gln Gln Gln Gln Gln
 65                  70                  75                  80

Gln Gln Gln Gln Gln Gln Gln Gln Gln Lys Gln Gln Gln His
                 85                  90                  95

His Met Gln Gln Gln Gln Gln Gln Pro Leu Ser Pro His Pro
            100                 105                 110

Pro Gly Ser Ser Ser Asn Ser Ser Ala Ala Ala Ala Ala Ala
        115                 120                 125

Ala Ala Ala Ala Ala Ala Val Asn Pro Gly Tyr Pro Pro Ser Ser
130                 135                 140

Ala Ala Ala Ala Ala Val Asn Ser Gly Tyr Pro Arg Pro Pro Gln
145                 150                 155                 160

His Arg Phe Ile Gln Asn Thr Gly Tyr Ser Ile Ala Pro Ala Pro Thr
            165                 170                 175

Tyr Arg Asp Asn Pro Tyr Ser Arg His Thr Gln Ile Gln Gln Gln Gln
            180                 185                 190

Gln Gln Gln Gln Gln Gln Gln Gln Gln Gln Gln Gln Gln Gln
        195                 200                 205

Gln Gln Gln Gln Ala Ala Ala Ser Met Pro Glu Tyr Gln Arg Ala Ala
210                 215                 220

Ala Arg Ala Ala Val Ala Ala Val Ser Ala Gly Lys Gly Asn Val Ser
225                 230                 235                 240

Gly Gln Ser Ser Asn Ser Ser Ser Ser Ser Gly Gly Gly Gly
                245                 250                 255

Gly Gly Ser Ala Gly Gly Ser Ala Pro Pro Gly Gly Gly Val Val Gln
            260                 265                 270

Val Ser Gln Ser Gly Gly Val Leu Val Met Glu Ala Met Pro His Tyr
        275                 280                 285

Ala Ser Gln Pro Asn Ser Asn Pro Ser Gln Gln Gln Gln Gln Gln
        290                 295                 300

Gln Gln Gln Gln Gly Gly Asn Pro Ser Gly Ala Gly Ala Thr Ser Gly
305                 310                 315                 320

Ala Gly Gly Gly Gly Gly Ser Gly Gly Ser Val Met Val Gly Ser
                325                 330                 335

Leu Gly Arg Ile Leu Met Pro His Pro Gln Ala Leu Gln Tyr Thr Ser
            340                 345                 350

Glu Tyr Leu Thr Asn Ala Thr Ala Val Ala Ala Ala Met Val Asn
        355                 360                 365

Gln Arg Gln His Leu Gln Leu Gln Gln Gln Gln Gln Gln His Pro
        370                 375                 380

Pro Glu Pro Phe Gly Gly Gln Gln Pro Tyr Lys Lys Gln Arg Leu Ser
385                 390                 395                 400

Glu Ala Asn Ala Asn Asn Met Asn His Leu Pro Pro His Pro Gln Gln
            405                 410                 415

Gln His Gln Gln Gln Gln Gln Gln Gln Gln His Gln Arg Ser Ser
        420                 425                 430

Pro Ala Gln Val Gln Gln Gln Gln Gln Gln Met Asn Ser Ser Arg
        435                 440                 445

Gln Ser His Asn Asp Met Cys Arg Gln Val Val Thr Thr Pro Met Gly
450                 455                 460

Met Gln Leu Lys Val Glu Thr Leu Pro Gln Gln Gln Lys Gln Gln
465                 470                 475                 480

Gln His Gln Gln Gln Gln Gln Gln Gln Gln Gly Arg Ser Gln Pro
```

```
                485                 490                 495
Val Val Ser Ser Met Ser Thr Val Ser Gln Pro Val Gly Thr Val
                500                 505                 510
Thr Val Thr Thr Ala Gly Leu Ser Ala Ser His Ser Gly Ser Ser Gly
                515                 520                 525
Asn Val Ala Ala Gly Leu Gly Thr Gly Asn Thr Gly Ser Ala Ser Thr
                530                 535                 540
Glu Ala Tyr His Pro Gln Val Glu Ala Ile Ser Pro Thr Leu Pro Ser
545                 550                 555                 560
Asp Ser Ser Ile Glu Glu Arg Gly Arg Thr Ser Ala Lys Glu Asp Leu
                565                 570                 575
Leu Met Gln Ile Gln Lys Val Asp Asn Glu Ile Lys Ser Ala Glu Thr
                580                 585                 590
Thr Met Glu Thr Leu Arg Lys Lys Glu Lys Ser Leu Met Glu Glu Ala
                595                 600                 605
Ala Leu Ala Lys Glu Gln Arg Ala Ala Lys Glu Leu Asn Asp Asn Asn
                610                 615                 620
Asn Asp Gln Glu Pro Met Val Glu Leu Ser Trp Arg Ser Gln Met Leu
625                 630                 635                 640
Ala Glu Lys Ile Tyr Ala Ala Asn Arg Lys Thr Ala Gln Ala Gln His
                645                 650                 655
Ser Met Leu Gln Asn Ala Ala Ala Asp Glu Ser Ser Pro Gly Ser Val
                660                 665                 670
Ala Gly Arg Pro Trp Leu Pro Leu Tyr Asn Gln Pro Leu Asp Val Glu
                675                 680                 685
Ala Leu Ala Met Leu Ile Arg Gln His Gln Ser Gln Ile Arg Ala Pro
                690                 695                 700
Leu Leu Leu His Ile Arg Lys Leu Lys Ala Glu Arg Trp Ala His Asn
705                 710                 715                 720
Gln Gly Leu Val Glu Lys Tyr Thr Lys Asp Gln Ala Asp Trp Gln Arg
                725                 730                 735
Arg Cys Glu Arg Met Glu Ala Ser Ala Lys Arg Lys Ala Arg Glu Ala
                740                 745                 750
Lys Asn Arg Glu Phe Phe Glu Lys Val Phe Thr Glu Leu Arg Lys Gln
                755                 760                 765
Arg Glu Asp Lys Glu Arg Phe Asn Arg Val Gly Ser Arg Ile Lys Ser
                770                 775                 780
Glu Ala Asp Leu Glu Glu Ile Met Asp Gly Leu Gln Glu Gln Ala Leu
785                 790                 795                 800
Glu Asp Lys Lys Met Arg Ser Tyr Ala Val Ile Pro Pro Leu Met His
                805                 810                 815
Asp Ala Arg Gln Arg Arg Cys Ala Tyr His Asn Glu Asn Gly Leu Ile
                820                 825                 830
Glu Asp Met Val Ala Val His Gln Gln Arg Lys Ala Leu Asn Met Trp
                835                 840                 845
Thr Ala Gly Glu Lys Glu Thr Phe Lys Glu Lys Tyr Leu Gln His Pro
850                 855                 860
Lys Asn Phe Gly Ala Ile Ala Ala Ser Leu Asp Arg Lys Ser Pro Gln
865                 870                 875                 880
Asp Cys Val Arg Tyr Tyr Tyr Leu Ser Lys Lys Thr Glu Asn Tyr Lys
                885                 890                 895
Gln Leu Leu Arg Lys Ser Arg Gln Arg Thr Arg Ser Ser Arg Asn Pro
                900                 905                 910
```

-continued

Ala Lys Ala Gln Ala Ala Gln Pro Gln Cys Ile Ile Asp Ser Met Thr
        915                 920                 925

Thr Gly Val Met Thr Arg Leu Gln Arg Glu Gln Gln Gln Lys Ser Gly
    930                 935                 940

Gly Arg Ser Ser Ala Val Ala Glu Arg Glu Arg Ala Glu Arg Ala Ala
945                 950                 955                 960

Glu Arg Glu Arg Val Ala Glu Lys Ala Ala Asp Ala Ala Lys Ala
            965                 970                 975

Ala Glu Ser Ala Ala Glu Lys Ala Ser Ala Ala Thr Lys Ala Val Glu
        980                 985                 990

Ala Thr Ala Ala Gly Glu Lys Val Ala Lys Ala Ala Ala Ala Ala
        995                 1000                1005

Ala Ala Ala Thr Thr Ala Thr Thr Ala Thr Thr Thr Thr Ser Ser
    1010                1015                1020

Ser Thr Ser Ser Ser Ser Ser Ala Ser Ser Ala Ser Thr Ala Ser
1025                1030                1035                1040

Ser Ser Thr Ala Ser Pro Ala Thr Leu Ala Gly Ile Ala Ala Asp Lys
        1045                1050                1055

Thr Asp Ala Gly Lys Thr Ala Ser Ala Ser Asp Lys Asn Ala Ala Thr
        1060                1065                1070

Ala Gly Gly Pro Thr Ala Thr Gly Thr Pro Thr Ala Ala Thr Thr Pro
        1075                1080                1085

Ala Thr Ala Thr Ala Pro Pro Glu Ile Ser Ala Gly Gly Glu Ala Lys
        1090                1095                1100

Ser Lys Asn Ala Glu Glu Glu Ala Ala Ala Thr Ala Gly Ala Ala Thr
1105                1110                1115                1120

Val Ala Thr Ala Gly Thr Pro Ala Thr Gly Ala Ser Ala Ala Ser Ala
        1125                1130                1135

Gly Glu Ala Thr Thr Ala Thr Gly Ala Thr Ala Thr Ala Ala Ala Lys
        1140                1145                1150

Gly Val Gly Lys Pro Glu Thr Ala Thr Glu Pro Ala Gly Thr Ala Ala
        1155                1160                1165

Lys Gly Ala Asp Ser Arg Pro Asp Ala Asn Asp Pro Leu Ala Lys Thr
        1170                1175                1180

Ala Ser Lys Ala Ile Asn Ala Glu Gly Tyr Asn Ala Ile Gly Gly Asn
1185                1190                1195                1200

Ser Ser Ser Ser Ser Ser Asn Ala Thr Gly Ala Ser Ala Pro Val Gln
        1205                1210                1215

Gly Val Thr Leu Asn Gly Phe Lys Pro Gly Tyr Gln Thr Val Val Met
        1220                1225                1230

Ala Asn Val Lys Ala Ser Thr Gly Gly Asp Asp Ser Gly Ala Asn Ala
        1235                1240                1245

Gly Gly Ala Ala Pro Gly Ser Leu Ala Ala Thr Asn Ala Ser Ile Ala
        1250                1255                1260

Thr Ser Gly Asp Lys Ile Val Lys Thr Thr Pro Ser Ser Arg Ala Pro
1265                1270                1275                1280

Asn Ser Thr Ser Ser Thr Ala Ala Asn Glu Ser Ser Ser Gly Ala Gly
        1285                1290                1295

Val Asn Thr Tyr Gly His Thr Ala Thr Ala Gly Asn Tyr Leu Gly
        1300                1305                1310

Gln Lys Leu Lys Ala Ala Gln Val Glu Gly Leu Gly Ala Gly Asn Glu
        1315                1320                1325

```
Leu His Ser Asp Val Ser Glu Ser Lys Arg Lys Arg Phe Glu Leu Asn
    1330            1335            1340

Ser Gly Glu Ala Gly Gly Asn Ala Thr Ser Ala Met Thr Asn Ser Ser
1345            1350            1355            1360

Thr Ser Gly Ser Met Asn Ile Ser Asn Ser His Gly Leu Lys Ala Asn
        1365            1370            1375

Ala Lys Asp Gly Ser Met Met Ala Lys Thr Ser Met Ala Ser Thr Ser
        1380            1385            1390

Ser Ala Ser Val Val Val Thr Ser Thr Pro Ser Ala Ser Ser Ser Ser
        1395            1400            1405

Leu Ser Ser Ala Ser Ser Met Leu Leu Ile Ser Ala Ala Ser Val Met
    1410            1415            1420

Ser Thr Ala Ala Gly Ala Thr Ser Ser Ser Thr Ala Thr Thr Thr Ala
1425            1430            1435            1440

Thr Ala Ser Ala Ile Ser Leu Pro Leu Leu Ala Asp Gly Ser Gly Asn
        1445            1450            1455

Ser Met Val Asn Ala Asn Glu Ile Leu Ala Leu Asp Gly Lys Asp Lys
        1460            1465            1470

Leu Ala Ser Cys Phe Val Cys Lys Ala Glu Ala Cys Pro Arg Thr Arg
    1475            1480            1485

Pro Leu Lys Lys Gly Arg Gly Gln Gln Tyr Gly Ile Pro Asp Glu Thr
    1490            1495            1500

Ile Pro Ala Gly Ala Arg Val Cys Asn Ser Cys Gln Cys Lys Ser Val
1505            1510            1515            1520

Arg Ser Arg Tyr Pro Asn Cys Pro Leu Pro Thr Cys Pro Asn Pro Lys
        1525            1530            1535

Asp Arg Ala Gln Arg Leu Arg Asn Ile Pro Ser Arg Leu Phe Glu Leu
        1540            1545            1550

Ala Pro Glu Val Arg Asp Pro Leu Met Ala Glu Phe Gln Ile Pro Pro
    1555            1560            1565

His Ala Thr Arg Cys Cys Ser Ala Cys Leu Met Arg Ile Arg Arg Lys
    1570            1575            1580

Leu Asp Pro Gln Leu Asn Leu Thr Asp Gly Ser Ser Gly Gly Ala Gly
1585            1590            1595            1600

Ser Gly Ser Gly Gly Asp Glu Thr Asp Val Ser Thr Ser Ser Cys Asp
        1605            1610            1615

Glu Arg Glu Pro Gly Gly Ser Asp Thr Ala Ser Val Glu Ser Pro Glu
        1620            1625            1630

Asn Leu Gln Arg His Lys Ser Leu Thr Met Val Lys Gln Gln Gln Gln
    1635            1640            1645

Gln Gln Gln Gln Gln Gln Gln Gln Gln Gln Gln Gln Gln Gln Gln Gln
    1650            1655            1660

Gln Gln Gln Leu Ser Gln Pro Gln Pro Pro Pro Ala Pro Gln Gln
1665            1670            1675            1680

Gln Lys Gly Ser Ser Gly Arg Gly Gly Asp Gln Gly Thr Pro Leu Ile
        1685            1690            1695

Ile Thr Pro Thr Arg Met Ser Ser Lys Ser Gly Ser Gly Gly Ala Gln
        1700            1705            1710

Thr Ala Gly Asp Asn Glu Arg Leu Leu Pro Ala Ala Gly Gln Ala
    1715            1720            1725

Pro Lys Lys Gln Lys Thr Ser Glu Glu Tyr Asp Ser Ser Ala Thr Glu
    1730            1735            1740

Thr Ala Asp Glu Glu Asn Glu Asn Ser Pro Ala Asn Arg Gln Ser Pro
```

-continued

```
                1745                1750                1755                1760
Lys Val Leu Phe His Gly His Gly His Gly His Gly Gly His Ala Asn
                    1765                1770                1775
Asn Val Ala Gly Leu Gln Pro Pro Val Ala Asn Met Gly Thr Gly Gly
                1780                1785                1790
Gly Val Gln Pro Gly Gly Ala Ala Gly Gln Gln Val Asn Gly Pro Ile
                1795                1800                1805
Ser Met Arg Arg Glu Ala Val Asn Asn Val Gln Asp Cys Val Phe Ser
            1810                1815                1820
Val Ile Glu Arg Ser Leu Lys His Lys Gly Pro Gln Pro Lys Gly Gly
1825                1830                1835                1840
Gln Gly Gln Gln Gln Gly Gln Gly Gln Gly Gln Gly Gln Gly
                    1845                1850                1855
Gln Thr Pro Gly Gln Ser Gln Ser Pro Ser Gln Gln Gln Gln Gln Gln
                1860                1865                1870
Gln Gln Gln Gln Ser Ala Asn Asn Leu Glu Arg Lys Glu Leu Thr Ile
                    1875                1880                1885
Val Arg Glu Tyr Arg Gln Asp Pro Gly Ile Leu Lys Gln Gln Gln Gln
        1890                1895                1900
Gln Gln Gln Ala Gly Gly Ala Pro Pro Thr Ser Ala Ala Gly Ser Leu
        1905                1910                1915                1920
Pro His Gly Thr Ser Val Gln Lys Leu Thr Thr Arg Pro Ala Ala Val
                    1925                1930                1935
Ala Pro Pro Pro Ala His Pro Leu Thr Pro Thr Ser Ile Gly Cys
                1940                1945                1950
Ala Gly Ser Asn Asn Gly Thr Ser Asp Ser Leu Ala Thr Leu Ser Val
                    1955                1960                1965
Val Asn Ser His Met Gly Met Val Gly Ile Gly His Pro Gly Pro Met
            1970                1975                1980
Ala His Ala Ser Ser Ala Gly Gly Ile Gly Val Asp Lys Ala Thr Ile
1985                1990                1995                2000
Thr Pro Val Val Lys Ser Ser Ser Gly Ser Ser Lys Ser Gly Gly Gly
                    2005                2010                2015
Ser Ala Ser Ser His Ser Thr Ala Thr Pro Pro Glu Thr Ile Ile Tyr
                2020                2025                2030
Asn Val Pro Val Ala His Pro Gln Arg Gly Ile Pro Pro Pro Ser Gln
                    2035                2040                2045
His Ser Val His Pro Ala His Pro Ser His Thr Gln His Pro Ala His
                2050                2055                2060
Pro Gln His Ser Ser His Gly Gln His Thr Gln Leu Gln Val Pro Glu
2065                2070                2075                2080
Pro Glu Pro Gln Thr Leu Asp Leu Ser Ile Lys Lys Pro Pro Arg Asp
                    2085                2090                2095
Gly His Ser Pro His Thr Gly Ala Gly Gly Ser Ser Ser Ser Gly Ser
                2100                2105                2110
Gly Ser Gly Gly Pro Ser Ser Ser Asp Arg His His Gly Pro Pro Pro
        2115                2120                2125
Pro Thr Met Ser Met Lys His Ile Val Arg Ser Gly Gly Met Tyr Arg
            2130                2135                2140
Gly Asp Thr Val Thr Val Pro Ser Leu Ala Ala Pro Ser Ser Tyr Leu
2145                2150                2155                2160
Tyr Pro Thr Arg Ser Val Lys Ser Ile Gly Gly Gly Gly Val Val Pro
                    2165                2170                2175
```

-continued

```
Gly Val Leu Pro Gly Val Pro Gly Ile Ala Leu Tyr Leu Gln Pro Val
            2180                2185                2190

Pro Val Pro Val Pro Ile Ser Ile Ser Gly Gln Gly Gln Leu Pro Pro
        2195                2200                2205

Lys Ala Gly Gln Pro Pro Ala Gln Pro Pro Ser Gly Arg Gly Val
    2210                2215                2220

Ala Lys Val Pro Pro Lys Leu Ser Pro Gln Gln Ala His His Leu His
2225                2230                2235                2240

Pro Ser His Gly His Ser Pro Ser Gln Gln Gln Gln Gln Gln Gln
            2245                2250                2255

Gln Gln Gln Gln Gln Gln Gln Gln Ala Ala Ala Ala Gln Gln Gln Leu
            2260                2265                2270

Leu Val Lys Ser Gly Ser Ile Ile His Gly Thr Pro Ala Asn Ser Ala
    2275                2280                2285

Gln Gln Gln Ile Ile Val His Ala Pro Ala Thr Ala Ala Ala Ala Pro
    2290                2295                2300

Ser Ser Leu Phe Ser Pro Lys Phe Asp Gly Leu Val Arg Gln Thr Thr
2305                2310                2315                2320

Pro Glu Gly Val Gly Ser Val Gly Pro Gly Gly Ala Ser Gly Ser Gly
            2325                2330                2335

Lys His Gly Ser Ile Thr Gln Gly Thr Pro Leu His Met Pro Pro His
            2340                2345                2350

His Leu Glu Ser Lys Arg Pro Tyr Glu Ser Tyr Tyr Lys Ser Ser Gln
            2355                2360                2365

Arg His Ser Pro Ala Gln Gln Pro Gly Gly Asn Gln Gln Leu Pro Pro
            2370                2375                2380

Pro Pro Gln Gln Ser Ser Pro Gln Ala Pro Pro Gln Gly Tyr Gly
2385                2390                2395                2400

Val Gly Val Ser Ser Pro Tyr Ala Arg Ser Pro Phe Ala Gly Val Val
            2405                2410                2415

Glu Gln Pro Gln Val Leu Ser Thr Arg Gln Ile Val Met His Asp Tyr
        2420                2425                2430

Ile Thr Ser Gln Gln Met Gln Gly Gln Gln Gln Gln Gln Gln Gln Gln
        2435                2440                2445

Gln Gln Gln Gln Arg Asn Met Ser Arg Gly Ser Ser Ala Ser Gly Gly
    2450                2455                2460

Gly Gly Gly Gly Gly Ser Asp Lys Glu Ser Pro Ser Pro Arg Asn Ser
2465                2470                2475                2480

Val Gly Ser Ala Ser Gly Phe Ala Tyr Gly Gly Asp Lys Glu Ser Ala
            2485                2490                2495

Pro Arg Gly Arg Pro Glu Tyr Ser Ser Arg Ala Ser Pro Ala Asp His
        2500                2505                2510

Val Asn Ser Thr Pro Ser Pro His Arg Thr Pro Pro Gln Arg Gln
    2515                2520                2525

Gly Val Ile Gln Arg His Asn Thr Gly Ser Lys Pro Pro Ser Pro Ala
    2530                2535                2540

Ala Pro Pro Pro Ser Arg Met His Met Pro Pro Tyr Gln Tyr Ala Pro
2545                2550                2555                2560

Ser Gly His Asp Ala Leu Ala Ser Phe Val Asp Val Ala Val Gln Gln
            2565                2570                2575

Pro Gln Leu Pro Val Pro Ser Gln Lys Asp Asp Lys Ser Pro Gly Pro
            2580                2585                2590
```

-continued

```
Ser Thr Ala Pro Gly Gln Val Pro Gly Ser Gly Pro Pro Leu Gly Pro
            2595                2600                2605

Ser Pro Leu Pro Pro His Ala Val Gly Val Ala Gln Pro Pro Pro
        2610                2615                2620

Pro Thr Ala His His Asp Gln Arg Tyr Arg Asp Leu Thr Leu His His
2625                2630                2635                2640

His His His Thr Leu Val Gln Gln Gln Ile Ala Gln Gln His Tyr
            2645                2650                2655

Arg Ser Leu Asn Val Ala Ala Gln Val Asp Met Gln Arg Gln Met Asp
        2660                2665                2670

Gln Ala Lys Arg Val Met Arg His Gln Gln His Gln Val Gln Gln Gln
        2675                2680                2685

Gln Gln Gln Gln Gln Gln Gln Gln His Asn His Ala Leu Glu Arg Asp
        2690                2695                2700

Arg Glu Met Gln Glu Arg Met Arg Glu Arg Asp Arg Glu Arg Glu Arg
2705                2710                2715                2720

Glu Arg Glu Arg Glu Gln Arg Glu Arg Glu Arg Glu Arg Glu
            2725                2730                2735

Arg Glu Arg Glu Arg Glu Arg Arg Glu Gln Asp Arg Ala Arg Arg Val
            2740                2745                2750

Val Ala Glu Glu Arg Glu His Asp Ser Arg Arg Met Glu Arg Met Phe
    2755                2760                2765

Ala Gly Asn Val Val Thr Gly Ser Gly Gly Ala Gly Gly Gly Gly Pro
        2770                2775                2780

Ser Pro Gly Gln Phe Leu Arg Ala Ser Val Pro Glu Thr Gly Pro Pro
2785                2790                2795                2800

Arg Ser Ile Pro Asp Arg Glu Arg Glu Ser Tyr Tyr Arg Gln Ala His
            2805                2810                2815

Gly Gly Pro Ala Pro Glu Asp Thr Pro Gly Gln Leu Ser Ala Gln Ser
            2820                2825                2830

Leu Ile Asp Ala Ile Ile Lys His Glu Ile Asn Arg Ser Asn Asp Ala
        2835                2840                2845

Thr Ala Gly Pro Gly Arg Glu Phe Pro Arg Pro Ser Phe Val His Ala
2850                2855                2860

Pro Leu Pro Pro Arg Gly Ser Gly Ser Gly Gly Gly Thr Gly Thr Arg
2865                2870                2875                2880

Ser Ser Pro Ala Asn Val Leu His Pro Met Tyr Leu Arg Asp Leu Arg
            2885                2890                2895

Gln Pro Leu Asp Gly Gly Ala Gly Ser Met Leu Thr Ala Glu Asn Asn
        2900                2905                2910

Gly Lys Pro Ser Ser Ser Gly Ser Pro Ser Val Ile Asn Ile Asp Leu
        2915                2920                2925

Asp Gln Glu Arg Ile Ser Ala Ala Ala Ala Val Ala Gln Gln Gln
        2930                2935                2940

Gln Gln Gln Gln Ala Pro Pro Ser Gln Ser Ser Gln Ser Arg Ser
2945                2950                2955                2960

Val His Gly Gln Leu Arg Thr Pro Thr Ser Gln Ser Gly Gly Ser Ala
            2965                2970                2975

Pro Ser Pro Gln Gln Ile His Thr Lys Ser Ile Thr Phe Gly Glu Leu
        2980                2985                2990

Thr Asp Ser Ile Ile Thr Ser Asp Tyr Gly Thr Asn Pro His Leu Arg
        2995                3000                3005

Pro Pro Tyr Met Ala Tyr Leu Gln Glu Thr Gln Ser Ile Leu Pro Pro
```

-continued

```
                   3010                3015                3020
Asp Arg Trp Lys Gln Asn Arg Met Gln Gln Lys Ala Glu Glu Ala
3025                3030                3035                3040
Asn Asp His Ser Gln Gln Gln Gln Gln Gln His Gln Gln His
                   3045                3050                3055
His Ala Gln Gln Gln Gln Gln Gln Gln Gln His His Ala Gln Gln
           3060                3065                3070
His His Pro Gln Met Pro Gly Thr Gly Ser Gly Ser Ala Pro Gly Gly
       3075                3080                3085
Ala Gly Gln Gly Gly Gly Ser Gly Gly Pro Gly Ser Gly Gly Gly Gly
3090                3095                3100
Ala Gly Arg Ala Ser Thr Pro Gly Glu Asp Gly Arg Asn Ile Ile Arg
3105                3110                3115                3120
Met Pro Gln Ala Val Ser Pro Arg Lys Phe Asn His Glu Met Met Leu
                   3125                3130                3135
His His Val Met Gly Thr Thr Gly Ala Gly Gly Glu Ala Gly Gln Phe
               3140                3145                3150
Phe Leu Pro Ser Arg Val Val Leu Pro Glu Gln Arg Gly Thr Pro Ser
       3155                3160                3165
Gly Gly Gly Gly Ala Pro Gly Ala Gly Gly Pro Gly Ser Gly Gly Gly
       3170                3175                3180
Ala Thr Thr Ile Glu Lys Tyr Val Lys Thr Arg Ile Ala Glu Val Met
3185                3190                3195                3200
Arg Asp Asp Ile Gly Tyr Gly Lys Asn Arg Thr Val Glu Val Arg Thr
                   3205                3210                3215
Glu Asp Glu Val Thr Ala Asp Met Val Ala His Ser His Ala Ala Val
               3220                3225                3230
His Ala Ala His Val Ala His Ala Ala His Val Ala His Ala Ala
           3235                3240                3245
Met Glu Leu Gln His Arg Ser Lys Glu Pro Pro Pro Glu Ile Ser
3250                3255                3260
Val Ser Arg Lys Thr Pro Asn Gln Tyr Glu Val Val Asp Ala Ser Gly
3265                3270                3275                3280
Arg Arg Ser Ala Gly Ser Gly Ser Val Ser Val Ser Val Ser Gly Ala
           3285                3290                3295
Asn Ser His His Ser Pro Tyr His Pro Pro Ala Ala Ala Tyr Ala Pro
               3300                3305                3310
Ser Thr Tyr Ala Phe Pro Tyr Ser Ala Leu Asn Val Pro Gly Ala Ala
       3315                3320                3325
Gly Gly Leu Pro Pro His Gln Pro Leu Gln Leu Ala His Gln Ala Val
       3330                3335                3340
Ala Pro Pro Gly Ala Phe Ala Lys Ala Lys Ala Ala His Ala Leu Ser
3345                3350                3355                3360
Glu Leu Gly Ala Val Gly Gly Gly Val Ser Leu Val Val Gly Gly Gly
               3365                3370                3375
Ser Gly Gly Ile Ala Gly Gly Pro Gly Gly Val Ser Val Gly Val Gly
           3380                3385                3390
Val Pro Gly Gly Gly Gly Pro Gly Ser Gly Gly Gly Gly Gly Gly
       3395                3400                3405
His Asn Ser Ser Ser Ser Gln Ala Ser Ala Ala Val Ala Ala Ala Val
       3410                3415                3420
Ala Ala Ala Ala Ser Glu Ser Lys Pro Leu Leu Leu Ser Lys Tyr Asp
3425                3430                3435                3440
```

```
Ala Leu Ser Asp Glu Asp
            3445

<210> SEQ ID NO 13
<211> LENGTH: 9
<212> TYPE: PRT
<213> ORGANISM: Drosophila sp.

<400> SEQUENCE: 13

Met Ala Pro Lys Lys Lys Arg Lys Val
  1               5

<210> SEQ ID NO 14
<211> LENGTH: 51
<212> TYPE: PRT
<213> ORGANISM: Drosophila sp.

<400> SEQUENCE: 14

Phe Arg His Ile Thr Glu Ile Thr Ile Leu Thr Val Gln Leu Ile Val
  1               5                  10                  15

Glu Phe Ala Lys Gly Leu Pro Ala Phe Tyr Lys Ile Pro Gln Glu Asp
             20                  25                  30

Gln Ile Thr Leu Leu Lys Ala Cys Ser Ser Glu Val Met Met Leu Arg
         35                  40                  45

Met Ala Arg
     50

<210> SEQ ID NO 15
<211> LENGTH: 51
<212> TYPE: PRT
<213> ORGANISM: Rattus sp.

<400> SEQUENCE: 15

Phe Ser Glu Phe Thr Lys Ile Ile Thr Pro Ala Ile Thr Arg Val Val
  1               5                  10                  15

Asp Phe Ala Lys Lys Leu Pro Met Phe Ser Glu Leu Pro Cys Glu Asp
             20                  25                  30

Gln Ile Ile Leu Leu Lys Gly Cys Cys Met Glu Ile Met Ser Leu Arg
         35                  40                  45

Ala Ala Val
     50

<210> SEQ ID NO 16
<211> LENGTH: 51
<212> TYPE: PRT
<213> ORGANISM: Homo sapiens

<400> SEQUENCE: 16

Trp Asp Lys Phe Ser Glu Leu Ala Thr Lys Cys Ile Ile Lys Ile Val
  1               5                  10                  15

Glu Phe Ala Lys Arg Leu Pro Gly Phe Thr Gly Leu Ser Ile Ala Asp
             20                  25                  30

Gln Ile Thr Leu Leu Lys Ala Ala Cys Leu Asp Ile Leu Met Leu Arg
         35                  40                  45

Ile Cys Thr
     50

<210> SEQ ID NO 17
<211> LENGTH: 51
<212> TYPE: PRT
```

<213> ORGANISM: Rattus sp.

<400> SEQUENCE: 17

Trp Glu Glu Phe Ser Met Ser Phe Thr Pro Ala Val Lys Glu Val Val
 1               5                  10                  15

Glu Phe Ala Lys Arg Ile Pro Gly Phe Arg Asp Leu Ser Gln His Asp
            20                  25                  30

Gln Val Asn Leu Leu Lys Ala Gly Thr Phe Glu Val Leu Met Val Arg
        35                  40                  45

Phe Ala Ser
    50

<210> SEQ ID NO 18
<211> LENGTH: 275
<212> TYPE: PRT
<213> ORGANISM: Drosophila sp.

<400> SEQUENCE: 18

Lys Glu Asp Leu Leu Met Gln Ile Gln Lys Val Asp Asn Glu Ile Lys
 1               5                  10                  15

Ser Ala Glu Thr Thr Met Glu Thr Leu Arg Lys Lys Glu Lys Ser Leu
            20                  25                  30

Met Glu Glu Ala Ala Leu Ala Lys Glu Gln Arg Ala Ala Lys Glu Leu
        35                  40                  45

Asn Asp Asn Asn Asn Asp Gln Glu Pro Met Val Glu Leu Ser Trp Arg
    50                  55                  60

Ser Gln Met Leu Ala Glu Lys Ile Tyr Ala Ala Asn Arg Lys Thr Ala
65                  70                  75                  80

Gln Ala Gln His Ser Met Leu Gln Asn Ala Ala Asp Glu Ser Ser
                85                  90                  95

Pro Gly Ser Val Ala Gly Arg Pro Trp Leu Pro Leu Tyr Asn Gln Pro
            100                 105                 110

Leu Asp Val Glu Ala Leu Ala Met Leu Ile Arg Gln His Gln Ser Gln
        115                 120                 125

Ile Arg Ala Pro Leu Leu His Ile Arg Lys Leu Lys Ala Glu Arg
    130                 135                 140

Trp Ala His Asn Gln Gly Leu Val Glu Lys Tyr Thr Lys Asp Gln Ala
145                 150                 155                 160

Asp Trp Gln Arg Arg Cys Glu Arg Met Glu Ala Ser Ala Lys Arg Lys
                165                 170                 175

Ala Arg Glu Ala Lys Asn Arg Glu Phe Phe Glu Lys Val Phe Thr Glu
            180                 185                 190

Leu Arg Lys Gln Arg Glu Asp Lys Glu Arg Phe Asn Arg Val Gly Ser
        195                 200                 205

Arg Ile Lys Ser Glu Ala Asp Leu Glu Ile Met Asp Gly Leu Gln
    210                 215                 220

Glu Gln Ala Leu Glu Asp Lys Lys Met Arg Ser Tyr Ala Val Ile Pro
225                 230                 235                 240

Pro Leu Met His Asp Ala Arg Gln Arg Cys Ala Tyr His Asn Glu
                245                 250                 255

Asn Phe Leu Ile Glu Asp Met Val Ala Val His Gln Gln Arg Lys Ala
            260                 265                 270

Leu Asn Met
    275

```
<210> SEQ ID NO 19
<211> LENGTH: 262
<212> TYPE: PRT
<213> ORGANISM: Mus sp.

<400> SEQUENCE: 19

Lys Glu Glu Leu Ile Gln Ser Met Asp Arg Val Asp Arg Glu Ile Ala
1               5                   10                  15

Lys Val Glu Gln Gln Ile Leu Lys Leu Lys Lys Lys Gln Gln Gln Leu
            20                  25                  30

Glu Glu Glu Ala Ala Lys Pro Pro Glu Pro Glu Lys Pro Val Ser Pro
        35                  40                  45

Pro Pro Val Glu Gln Lys His Arg Ser Ile Val Gln Ile Ile Tyr Asp
    50                  55                  60

Glu Asn Arg Lys Lys Ala Glu Glu Ala His Lys Ile Phe Glu Gly Leu
65                  70                  75                  80

Gly Pro Lys Val Glu Leu Pro Leu Tyr Asn Gln Pro Ser Asp Thr Lys
                85                  90                  95

Val Tyr His Glu Asn Ile Lys Thr Asn Gln Val Met Arg Lys Lys Leu
            100                 105                 110

Ile Leu Phe Phe Lys Arg Arg Asn His Ala Arg Lys Gln Arg Glu Gln
        115                 120                 125

Lys Ile Cys Gln Arg Tyr Asp Gln Leu Met Glu Ala Trp Glu Lys Lys
    130                 135                 140

Val Asp Arg Ile Glu Asn Asn Pro Arg Arg Lys Ala Lys Glu Ser Lys
145                 150                 155                 160

Thr Arg Glu Tyr Tyr Glu Lys Gln Phe Pro Glu Ile Arg Lys Gln Arg
                165                 170                 175

Glu Gln Gln Glu Arg Phe Gln Arg Val Gly Gln Arg Gly Ala Gly Leu
            180                 185                 190

Ser Ala Thr Ile Ala Arg Ser Glu His Glu Ile Ser Glu Ile Ile Asp
        195                 200                 205

Gly Leu Ser Glu Gln Glu Asn Asn Glu Lys Gln Met Arg Gln Leu Ser
    210                 215                 220

Val Ile Pro Pro Met Met Phe Asp Ala Glu Gln Arg Arg Val Lys Phe
225                 230                 235                 240

Ile Asn Met Asn Gly Leu Met Glu Asp Pro Met Lys Val Tyr Lys Asp
                245                 250                 255

Arg Gln Phe Met Asn Val
            260

<210> SEQ ID NO 20
<211> LENGTH: 263
<212> TYPE: PRT
<213> ORGANISM: Homo sapiens

<400> SEQUENCE: 20

Lys Glu Glu Leu Ile Gln Asn Met Asp Arg Val Asp Arg Glu Ile Thr
1               5                   10                  15

Met Val Glu Gln Gln Ile Ser Lys Leu Lys Lys Lys Gln Gln Gln Leu
            20                  25                  30

Glu Glu Glu Ala Ala Lys Pro Pro Glu Pro Glu Lys Pro Val Ser Pro
        35                  40                  45

Pro Pro Ile Glu Ser Lys His Arg Ser Leu Val Gln Ile Ile Tyr Asp
    50                  55                  60

Glu Asn Arg Lys Lys Ala Glu Ala Ala His Arg Ile Leu Glu Gly Leu
```

```
                65                  70                  75                  80
Gly Pro Gln Val Glu Leu Pro Leu Tyr Asn Gln Pro Ser Asp Thr Arg
                    85                  90                  95
Gln Tyr His Glu Asn Ile Lys Ile Asn Gln Ala Met Arg Lys Lys Leu
                100                 105                 110
Ile Leu Tyr Phe Lys Arg Arg Asn His Ala Arg Lys Gln Trp Lys Gln
                115                 120                 125
Lys Phe Cys Gln Arg Tyr Asp Gln Leu Met Glu Ala Leu Glu Lys Lys
            130                 135                 140
Val Glu Arg Ile Glu Asn Asn Pro Arg Arg Ala Lys Glu Ser Lys
145                 150                 155                 160
Val Arg Glu Tyr Tyr Glu Lys Gln Phe Pro Glu Ile Arg Lys Gln Arg
                165                 170                 175
Glu Leu Gln Glu Arg Met Gln Ser Arg Val Gly Gln Arg Gly Ser Gly
                180                 185                 190
Leu Ser Met Ser Ala Ala Arg Ser Glu His Glu Val Ser Glu Ile Ile
            195                 200                 205
Asp Gly Leu Ser Glu Gln Glu Asn Leu Glu Lys Gln Met Arg Gln Leu
        210                 215                 220
Ala Val Ile Pro Pro Met Leu Tyr Asp Ala Asp Gln Gln Arg Ile Lys
225                 230                 235                 240
Phe Ile Asn Met Asn Gly Leu Met Ala Asp Pro Met Lys Val Tyr Lys
                245                 250                 255
Asp Arg Gln Val Met Asn Met
            260

<210> SEQ ID NO 21
<211> LENGTH: 48
<212> TYPE: PRT
<213> ORGANISM: Drosophila sp.

<400> SEQUENCE: 21

Trp Thr Ala Gly Glu Lys Glu Thr Phe Lys Glu Lys Tyr Leu Gln His
 1               5                  10                  15
Pro Lys Asn Phe Gly Ala Ile Ala Ala Ser Leu Asp Arg Lys Ser Pro
                20                  25                  30
Gln Asp Cys Val Arg Tyr Tyr Leu Ser Lys Lys Thr Glu Asn Tyr
            35                  40                  45

<210> SEQ ID NO 22
<211> LENGTH: 48
<212> TYPE: PRT
<213> ORGANISM: Mus sp.

<400> SEQUENCE: 22

Trp Thr Asp His Glu Lys Glu Ile Phe Lys Asp Lys Phe Ile Gln His
 1               5                  10                  15
Pro Lys Asn Phe Gly Leu Ile Ala Ser Tyr Leu Glu Arg Lys Ser Val
                20                  25                  30
Pro Asp Cys Val Leu Tyr Tyr Leu Thr Lys Lys Asn Glu Asn Tyr
            35                  40                  45

<210> SEQ ID NO 23
<211> LENGTH: 48
<212> TYPE: PRT
<213> ORGANISM: Homo sapiens

<400> SEQUENCE: 23
```

-continued

```
Trp Ser Glu Gln Glu Lys Glu Thr Phe Arg Glu Lys Phe Met Gln His
  1               5                  10                  15

Pro Lys Asn Phe Gly Leu Ile Ala Ser Phe Leu Glu Arg Lys Thr Val
             20                  25                  30

Ala Glu Cys Val Leu Tyr Tyr Leu Thr Lys Lys Asn Glu Asn Tyr
         35                  40                  45
```

<210> SEQ ID NO 24
<211> LENGTH: 48
<212> TYPE: PRT
<213> ORGANISM: Caenorhabditis elegans

<400> SEQUENCE: 24

```
Trp Ser Pro Glu Glu Arg Ser Leu Phe Lys Ser Arg Gln Ala Asp His
  1               5                  10                  15

Val Lys Ile Phe His Gly Leu Thr Glu Phe Val Asp Lys Thr Ala
             20                  25                  30

Ser Asp Leu Val Leu Phe Tyr Tyr Met Asn Lys Lys Thr Glu Asp Tyr
         35                  40                  45
```

<210> SEQ ID NO 25
<211> LENGTH: 48
<212> TYPE: PRT
<213> ORGANISM: Caenorhabditis elegans

<400> SEQUENCE: 25

```
Trp Thr Pro Asp Glu Ile Tyr Gln Phe Gln Asp Ala Ile Tyr Gln Ser
  1               5                  10                  15

Glu Lys Asp Phe Asp Lys Val Ala Val Glu Leu Pro Gly Lys Ser Val
             20                  25                  30

Lys Glu Cys Val Gln Phe Tyr Tyr Thr Trp Lys Lys Asp Cys Pro Asp
         35                  40                  45
```

<210> SEQ ID NO 26
<211> LENGTH: 49
<212> TYPE: PRT
<213> ORGANISM: Xenopus sp.

<400> SEQUENCE: 26

```
Trp Thr Glu Glu Glu Cys Arg Asn Phe Glu Gln Gly Leu Lys Ala Tyr
  1               5                  10                  15

Gly Lys Asp Phe His Leu Ile Gln Ala Asn Lys Val Arg Thr Arg Ser
             20                  25                  30

Val Gly Glu Cys Val Ala Phe Tyr Tyr Met Trp Lys Lys Ser Glu Arg
         35                  40                  45

Tyr
```

<210> SEQ ID NO 27
<211> LENGTH: 48
<212> TYPE: PRT
<213> ORGANISM: Mus sp.

<400> SEQUENCE: 27

```
Trp Thr Glu Glu Glu Met Glu Val Ala Lys Lys Gly Leu Val Glu His
  1               5                  10                  15

Gly Arg Asn Trp Ala Ala Ile Ala Lys Met Val Gly Thr Lys Ser Glu
             20                  25                  30

Ala Gln Cys Lys Asn Phe Tyr Phe Asn Tyr Lys Arg Arg His Asn Leu
         35                  40                  45
```

```
<210> SEQ ID NO 28
<211> LENGTH: 48
<212> TYPE: PRT
<213> ORGANISM: Homo sapiens

<400> SEQUENCE: 28

Trp Thr Glu Glu Met Glu Thr Ala Lys Lys Gly Leu Leu Glu His
 1               5                  10                  15

Gly Arg Asn Trp Ser Ala Ile Ala Arg Met Val Gly Ser Lys Thr Val
                20                  25                  30

Ser Gln Cys Lys Asn Phe Tyr Phe Asn Tyr Lys Lys Arg Gln Asn Leu
            35                  40                  45

<210> SEQ ID NO 29
<211> LENGTH: 48
<212> TYPE: PRT
<213> ORGANISM: Homo sapiens

<400> SEQUENCE: 29

Trp Thr Val Glu Asp Lys Val Leu Phe Glu Gln Ala Phe Ser Phe His
 1               5                  10                  15

Gly Lys Thr Phe His Arg Ile Gln Gln Met Leu Pro Asp Lys Ser Ile
                20                  25                  30

Ala Ser Leu Val Lys Phe Tyr Tyr Ser Trp Lys Lys Thr Arg Thr Lys
            35                  40                  45

<210> SEQ ID NO 30
<211> LENGTH: 48
<212> TYPE: PRT
<213> ORGANISM: Caenorhabditis elegans

<400> SEQUENCE: 30

Trp Thr Asp Gln Glu Ile Thr Leu Phe Glu Asn Cys Tyr Gln Ile Phe
 1               5                  10                  15

Gly Lys Asn Phe Ser Gln Ile Arg Ser Ala Leu Cys His Arg Ser Leu
                20                  25                  30

Gln Ser Ile Val Gln Phe Tyr Tyr Glu Ser Lys Lys Arg Val Lys Tyr
            35                  40                  45

<210> SEQ ID NO 31
<211> LENGTH: 49
<212> TYPE: PRT
<213> ORGANISM: Saccharomyces sp.

<400> SEQUENCE: 31

Phe Thr Asp His Glu His Ser Leu Phe Leu Gly Tyr Leu Ile His
 1               5                  10                  15

Pro Lys Lys Phe Gly Lys Ile Ser His Tyr Met Gly Gly Leu Arg Ser
                20                  25                  30

Pro Glu Glu Cys Val Leu His Tyr Tyr Arg Thr Lys Lys Thr Val Asn
            35                  40                  45

Tyr

<210> SEQ ID NO 32
<211> LENGTH: 16
<212> TYPE: PRT
<213> ORGANISM: Drosophila sp.

<400> SEQUENCE: 32
```

Thr Arg Gln Ile Val Met His Asp Tyr Ile Thr Ser Gln Gln Met Gln
1               5                   10                  15

<210> SEQ ID NO 33
<211> LENGTH: 16
<212> TYPE: PRT
<213> ORGANISM: Homo sapiens

<400> SEQUENCE: 33

Asn Arg Gln Thr Ile Ile Asn Asp Tyr Ile Thr Ser Gln Gln Met His
1               5                   10                  15

<210> SEQ ID NO 34
<211> LENGTH: 16
<212> TYPE: PRT
<213> ORGANISM: Mus sp.

<400> SEQUENCE: 34

Thr Arg Gln Thr Ile Leu Asn Asp Tyr Ile Thr Ser Gln Gln Met Gln
1               5                   10                  15

<210> SEQ ID NO 35
<211> LENGTH: 17
<212> TYPE: PRT
<213> ORGANISM: Drosophila sp.

<400> SEQUENCE: 35

Glu Ser Lys Pro Leu Leu Leu Ser Lys Tyr Asp Ala Leu Ser Asp Glu
1               5                   10                  15
Asp

<210> SEQ ID NO 36
<211> LENGTH: 17
<212> TYPE: PRT
<213> ORGANISM: Homo sapiens

<400> SEQUENCE: 36

Glu Pro Lys Pro Leu Leu Cys Ser Gln Tyr Glu Thr Leu Ser Asp Ser
1               5                   10                  15
Glu

<210> SEQ ID NO 37
<211> LENGTH: 18
<212> TYPE: PRT
<213> ORGANISM: Mus sp.

<400> SEQUENCE: 37

Glu Pro Ala Pro Leu Leu Ser Ala Gln Tyr Glu Thr Leu Ser Asp Ser
1               5                   10                  15
Asp Asp

<210> SEQ ID NO 38
<211> LENGTH: 14
<212> TYPE: PRT
<213> ORGANISM: Drosophila sp.

<400> SEQUENCE: 38

Val Lys Ser Gly Ser Ile Ile His Gly Thr Pro Ala Asn Ser
1               5                   10

<210> SEQ ID NO 39
<211> LENGTH: 14
<212> TYPE: PRT

<213> ORGANISM: Drosophila sp.

<400> SEQUENCE: 39

Gly Lys His Gly Ser Ile Thr Gln Gly Thr Pro Leu His Met
 1               5                  10

<210> SEQ ID NO 40
<211> LENGTH: 14
<212> TYPE: PRT
<213> ORGANISM: Homo sapiens

<400> SEQUENCE: 40

Val Pro Gly Gly Ser Ile Thr Lys Gly Ile Pro Ser Thr Arg
 1               5                  10

<210> SEQ ID NO 41
<211> LENGTH: 14
<212> TYPE: PRT
<213> ORGANISM: Homo sapiens

<400> SEQUENCE: 41

Thr Tyr Arg Gly Ser Ile Thr His Gly Thr Pro Ala Asp Val
 1               5                  10

<210> SEQ ID NO 42
<211> LENGTH: 14
<212> TYPE: PRT
<213> ORGANISM: Homo sapiens

<400> SEQUENCE: 42

His Ile Arg Gly Ser Ile Thr Gln Gly Ile Pro Arg Ser Tyr
 1               5                  10

<210> SEQ ID NO 43
<211> LENGTH: 14
<212> TYPE: PRT
<213> ORGANISM: Homo sapiens

<400> SEQUENCE: 43

Leu Lys Glu Gly Ser Ile Thr Gln Gly Thr Pro Leu Lys Tyr
 1               5                  10

<210> SEQ ID NO 44
<211> LENGTH: 14
<212> TYPE: PRT
<213> ORGANISM: Homo sapiens

<400> SEQUENCE: 44

Ser Ser Gly Gly Ser Ile Ala Arg Gly Ala Pro Val Ile Val
 1               5                  10

<210> SEQ ID NO 45
<211> LENGTH: 14
<212> TYPE: PRT
<213> ORGANISM: Mus sp.

<400> SEQUENCE: 45

Thr Pro Pro Gly Ser Ile Leu Ile Ser Ser Pro Ile Lys Pro
 1               5                  10

<210> SEQ ID NO 46
<211> LENGTH: 14
<212> TYPE: PRT
<213> ORGANISM: Mus sp.

```
<400> SEQUENCE: 46

Ile Met Gly Gly Ser Ile Ser Gln Gly Thr Pro Gly Thr Tyr
 1               5                  10

<210> SEQ ID NO 47
<211> LENGTH: 14
<212> TYPE: PRT
<213> ORGANISM: Mus sp.

<400> SEQUENCE: 47

Pro Ser Val Gly Ser Ile Ser Leu Gly Leu Pro Arg Gln Gln
 1               5                  10

<210> SEQ ID NO 48
<211> LENGTH: 14
<212> TYPE: PRT
<213> ORGANISM: Mus sp.

<400> SEQUENCE: 48

Val Gln Glu Gly Ser Ile Thr Arg Gly Thr Pro Ala Ser Lys
 1               5                  10

<210> SEQ ID NO 49
<211> LENGTH: 14
<212> TYPE: PRT
<213> ORGANISM: Mus sp.

<400> SEQUENCE: 49

Ser Leu Arg Gly Ser Ile Thr Gln Gly Thr Pro Ala Leu Pro
 1               5                  10

<210> SEQ ID NO 50
<211> LENGTH: 14
<212> TYPE: PRT
<213> ORGANISM: Mus sp.

<400> SEQUENCE: 50

Val Leu Ser Gly Ser Ile Met Gln Gly Thr Pro Arg Ala Thr
 1               5                  10

<210> SEQ ID NO 51
<211> LENGTH: 14
<212> TYPE: PRT
<213> ORGANISM: Mus sp.

<400> SEQUENCE: 51

Ile Ile Glu Gly Ser Ile Ser Gln Gly Thr Pro Ile Lys Phe
 1               5                  10

<210> SEQ ID NO 52
<211> LENGTH: 14
<212> TYPE: PRT
<213> ORGANISM: Caenorhabditis elegans

<400> SEQUENCE: 52

Gln Thr Gln Gly Ser Leu Thr Ser Gly Thr Pro Phe Gln Ala
 1               5                  10
```